(12) United States Patent
Talbert et al.

(10) Patent No.: US 11,266,304 B2
(45) Date of Patent: *Mar. 8, 2022

(54) MINIMIZING IMAGE SENSOR INPUT/OUTPUT IN A PULSED HYPERSPECTRAL IMAGING SYSTEM

(71) Applicant: Cilag GmbH International, Zug (CH)

(72) Inventors: Joshua D. Talbert, Salt Lake City, UT (US); Donald M. Wichern, Ogden, UT (US)

(73) Assignee: Cilag GmbH International

( * ) Notice: Subject to any disclaimer, the term of this patent is extended or adjusted under 35 U.S.C. 154(b) by 67 days.

This patent is subject to a terminal disclaimer.

(21) Appl. No.: 16/776,246

(22) Filed: Jan. 29, 2020

(65) Prior Publication Data
US 2020/0400829 A1    Dec. 24, 2020

Related U.S. Application Data

(60) Provisional application No. 62/864,234, filed on Jun. 20, 2019.

(51) Int. Cl.
*G01S 17/89*    (2020.01)
*G06T 7/521*    (2017.01)
(Continued)

(52) U.S. Cl.
CPC .......... *A61B 1/043* (2013.01); *A61B 1/00006* (2013.01); *A61B 1/0638* (2013.01);
(Continued)

(58) Field of Classification Search
CPC ..... A61B 5/489; A61B 5/0261; A61B 5/4893; A61B 5/0071; A61B 5/4887;
(Continued)

(56) References Cited

U.S. PATENT DOCUMENTS

| 4,768,513 A | 9/1988 | Suzuki |
| 5,318,024 A | 6/1994 | Kittrell et al. |

(Continued)

FOREIGN PATENT DOCUMENTS

| CN | 111526775 A | 8/2020 |
| CN | 111565620 A | 8/2020 |

(Continued)

*Primary Examiner* — Sang H Nguyen
(74) *Attorney, Agent, or Firm* — Terrence J. Edwards; TechLaw Ventures, PLLC

(57) ABSTRACT

Pulsed hyperspectral imaging in a light deficient environment is disclosed. A system includes an emitter for emitting pulses of electromagnetic radiation and an image sensor comprising a pixel array for sensing reflected electromagnetic radiation. The system includes a plurality of bidirectional pads comprising an output state for issuing data and an input state for receiving data. The system includes a controller configured to synchronize timing of the emitter and the image sensor. The system is such that at least a portion of the pulses of electromagnetic radiation emitted by the emitter comprises electromagnetic radiation having a wavelength from about 513 nm to about 545 nm, from about 565 nm to about 585 nm, or from about 900 nm to about 1000 nm.

23 Claims, 29 Drawing Sheets

(51) Int. Cl.

| | |
|---|---|
| *G01N 21/64* | (2006.01) |
| *A61B 1/04* | (2006.01) |
| *H04N 5/235* | (2006.01) |
| *H04N 13/239* | (2018.01) |
| *H04N 9/04* | (2006.01) |
| *G06T 7/70* | (2017.01) |
| *G06T 7/00* | (2017.01) |
| *A61B 1/00* | (2006.01) |
| *A61B 1/06* | (2006.01) |
| *A61B 5/026* | (2006.01) |
| *A61B 5/20* | (2006.01) |
| *A61B 5/00* | (2006.01) |
| *G02B 5/20* | (2006.01) |
| *G06T 7/20* | (2017.01) |
| *A61B 1/07* | (2006.01) |
| *H04N 5/225* | (2006.01) |
| *G01S 7/483* | (2006.01) |

(52) U.S. Cl.
CPC .............. *A61B 5/0261* (2013.01); *A61B 5/20* (2013.01); *A61B 5/489* (2013.01); *A61B 5/4887* (2013.01); *A61B 5/4893* (2013.01); *G01N 21/6456* (2013.01); *G01S 17/89* (2013.01); *G02B 5/208* (2013.01); *G06T 7/0012* (2013.01); *G06T 7/20* (2013.01); *G06T 7/521* (2017.01); *G06T 7/70* (2017.01); *H04N 5/2354* (2013.01); *H04N 5/2356* (2013.01); *H04N 9/04521* (2018.08); *H04N 13/239* (2018.05); *A61B 1/063* (2013.01); *A61B 1/07* (2013.01); *G01S 7/483* (2013.01); *G06T 2207/10012* (2013.01); *G06T 2207/10016* (2013.01); *G06T 2207/10024* (2013.01); *G06T 2207/10028* (2013.01); *G06T 2207/10036* (2013.01); *G06T 2207/10064* (2013.01); *G06T 2207/10068* (2013.01); *G06T 2207/10152* (2013.01); *G06T 2207/20212* (2013.01); *G06T 2207/30096* (2013.01); *G06T 2207/30101* (2013.01); *G06T 2207/30104* (2013.01); *H04N 2005/2255* (2013.01)

(58) Field of Classification Search
CPC ......... A61B 5/0084; A61B 5/20; A61B 1/043; A61B 1/00009; A61B 1/07; A61B 1/063; A61B 1/045; A61B 1/0646; A61B 1/00006; A61B 1/0638; H04N 5/2256; H04N 5/379; H04N 5/2354; H04N 5/2355; H04N 5/2253; H04N 5/3532; H04N 5/2356; H04N 13/254; H04N 13/257; H04N 13/214; H04N 13/239; H04N 13/218; H04N 9/04521; H04N 2005/2255; G06T 7/70; G06T 7/20; G06T 7/521; G06T 7/0012; G06T 2207/10028; G06T 2207/10012; G06T 2207/10024; G06T 2207/30096; G06T 2207/30104; G06T 2207/10016; G06T 2207/10036; G06T 2207/10064; G06T 2207/10068; G06T 2207/20212; G06T 2207/10152; G06T 2207/30101; G02B 5/208; G01N 21/6456; G01N 2021/6439; G01S 17/89; G01S 157/483

See application file for complete search history.

(56) References Cited

U.S. PATENT DOCUMENTS

| | | |
|---|---|---|
| 5,363,387 A | 11/1994 | Sinofsky |
| 5,481,085 A | 1/1996 | Kovacevic et al. |
| 5,749,830 A | 5/1998 | Kaneko et al. |
| 6,110,106 A | 8/2000 | MacKinnon et al. |
| 6,236,879 B1 | 5/2001 | Konings |
| 6,975,898 B2 | 12/2005 | Seibel |
| 9,509,917 B2 | 11/2016 | Blanquart et al. |
| 10,517,569 B2 | 12/2019 | Weitzel et al. |
| 10,750,933 B2 | 8/2020 | Blanquart |
| 11,071,443 B2 | 7/2021 | Talbert et al. |
| 2001/0000317 A1 | 4/2001 | Yoneya et al. |
| 2001/0055462 A1 | 12/2001 | Seibel |
| 2002/0123666 A1 | 9/2002 | Matsumoto |
| 2002/0161282 A1 | 10/2002 | Fulghum |
| 2003/0100824 A1 | 5/2003 | Warren et al. |
| 2003/0191368 A1 | 10/2003 | Wang et al. |
| 2004/0010192 A1 | 1/2004 | Benaron et al. |
| 2004/0186351 A1 | 9/2004 | Imaizumi et al. |
| 2004/0234152 A1 | 11/2004 | Liege et al. |
| 2005/0020926 A1 | 1/2005 | Wiklof et al. |
| 2005/0107808 A1 | 5/2005 | Evans et al. |
| 2006/0069314 A1 | 3/2006 | Farr |
| 2006/0239723 A1 | 10/2006 | Okuda et al. |
| 2006/0276966 A1 | 12/2006 | Cotton et al. |
| 2007/0016077 A1 | 1/2007 | Nakaoka et al. |
| 2007/0046778 A1 | 3/2007 | Ishihara et al. |
| 2007/0081188 A1 | 4/2007 | Kim |
| 2007/0086495 A1 | 4/2007 | Sprague et al. |
| 2007/0242330 A1 | 10/2007 | Rosman et al. |
| 2007/0276234 A1 | 11/2007 | Shahidi |
| 2008/0058629 A1 | 3/2008 | Seibel et al. |
| 2008/0081950 A1 | 4/2008 | Koenig et al. |
| 2008/0177139 A1 | 7/2008 | Courtney et al. |
| 2008/0177140 A1 | 7/2008 | Cline et al. |
| 2008/0239070 A1 | 10/2008 | Westwick et al. |
| 2009/0306478 A1 | 12/2009 | Mizuyoshi |
| 2010/0049180 A1 | 2/2010 | Wells et al. |
| 2010/0128109 A1 | 5/2010 | Banks |
| 2010/0261958 A1 | 10/2010 | Webb et al. |
| 2010/0277087 A1 | 11/2010 | Ikeda |
| 2011/0087212 A1 | 4/2011 | Aldridge et al. |
| 2011/0196355 A1 | 8/2011 | Mitchell et al. |
| 2011/0206075 A1 | 8/2011 | Ji et al. |
| 2011/0213252 A1 | 9/2011 | Fulghum |
| 2011/0280810 A1 | 11/2011 | Hauger et al. |
| 2011/0311142 A1* | 12/2011 | Robles-Kelly ....... G06K 9/4652 382/191 |
| 2012/0010465 A1 | 1/2012 | Erikawa et al. |
| 2012/0123205 A1 | 5/2012 | Nie et al. |
| 2012/0294498 A1 | 11/2012 | Popovic |
| 2012/0307030 A1* | 12/2012 | Blanquart ............ H01L 27/1464 348/76 |
| 2013/0176395 A1 | 7/2013 | Kazakevich |
| 2013/0211246 A1 | 8/2013 | Parasher |
| 2013/0264465 A1 | 10/2013 | Dai et al. |
| 2013/0274596 A1 | 10/2013 | Azizian et al. |
| 2013/0324797 A1 | 12/2013 | Igarashi et al. |
| 2014/0073885 A1 | 3/2014 | Frangioni |
| 2014/0111623 A1 | 4/2014 | Zhao et al. |
| 2014/0160259 A1 | 6/2014 | Blanquart et al. |
| 2014/0160260 A1* | 6/2014 | Blanquart ............ H04N 13/239 348/68 |
| 2014/0160318 A1 | 6/2014 | Blanquart et al. |
| 2014/0163319 A1* | 6/2014 | Blanquart ............ A61B 1/0684 600/109 |
| 2014/0271482 A1 | 9/2014 | Low et al. |
| 2014/0275783 A1 | 9/2014 | Blanquart |
| 2014/0276000 A1 | 9/2014 | Mullaney et al. |
| 2014/0276093 A1 | 9/2014 | Zeien |
| 2014/0285645 A1* | 9/2014 | Blanquart ............ H04N 5/3765 348/68 |
| 2014/0300750 A1* | 10/2014 | Nagamune ................ G01J 3/32 348/164 |
| 2014/0336461 A1 | 11/2014 | Reiter et al. |
| 2014/0336501 A1 | 11/2014 | Masumoto |
| 2015/0044098 A1* | 2/2015 | Smart .................... G01J 3/2823 422/82.05 |
| 2015/0073209 A1 | 3/2015 | Ikeda |
| 2015/0223733 A1 | 8/2015 | Al-Alusi |
| 2015/0289937 A1 | 10/2015 | Chia et al. |
| 2015/0305604 A1 | 10/2015 | Melsky |

(56) References Cited

U.S. PATENT DOCUMENTS

| | | |
|---|---|---|
| 2015/0309284 A1 | 10/2015 | Kagawa et al. |
| 2016/0006914 A1 | 1/2016 | Neumann |
| 2016/0042513 A1 | 2/2016 | Yudovsky |
| 2016/0062103 A1* | 3/2016 | Yang ............... A61B 1/042 250/552 |
| 2016/0183775 A1 | 6/2016 | Blanquart et al. |
| 2016/0195706 A1 | 7/2016 | Fujii |
| 2016/0360074 A1 | 12/2016 | Winer et al. |
| 2017/0078548 A1 | 3/2017 | Blanquart et al. |
| 2017/0209050 A1 | 7/2017 | Fengler et al. |
| 2017/0280029 A1 | 9/2017 | Steiner |
| 2017/0280970 A1 | 10/2017 | Sartor et al. |
| 2017/0360275 A1 | 12/2017 | Yoshizaki |
| 2018/0131880 A1 | 5/2018 | Hicks et al. |
| 2018/0310828 A1 | 11/2018 | DiMaio et al. |
| 2019/0110686 A1 | 4/2019 | Kato |
| 2019/0125454 A1 | 5/2019 | Stokes et al. |
| 2019/0125458 A1 | 5/2019 | Shelton, IV et al. |
| 2019/0170873 A1 | 6/2019 | Reid |
| 2019/0191974 A1 | 6/2019 | Talbert et al. |
| 2019/0191975 A1 | 6/2019 | Talbert et al. |
| 2019/0191976 A1 | 6/2019 | Talbert et al. |
| 2019/0191977 A1 | 6/2019 | Talbert et al. |
| 2019/0191978 A1 | 6/2019 | Talbert et al. |
| 2019/0197712 A1 | 6/2019 | Talbert et al. |
| 2020/0397243 A1 | 12/2020 | Talbert et al. |
| 2020/0397244 A1 | 12/2020 | Talbert et al. |
| 2020/0397245 A1 | 12/2020 | Talbert et al. |
| 2020/0397246 A1 | 12/2020 | Talbert et al. |
| 2020/0400830 A1 | 12/2020 | Talbert et al. |

FOREIGN PATENT DOCUMENTS

| | | |
|---|---|---|
| CN | 111601536 A | 8/2020 |
| JP | 2008259595 A | 10/2008 |
| WO | 2014018951 A1 | 1/2014 |
| WO | 2014134314 A1 | 9/2014 |
| WO | WO 2015077493 A1 | 5/2015 |
| WO | 2016203572 A1 | 12/2016 |
| WO | WO 2017201093 A1 | 11/2017 |
| WO | WO 2017223206 A1 | 12/2017 |
| WO | WO 2018049215 A1 | 3/2018 |
| WO | WO 2019079010 A1 | 4/2019 |
| WO | WO 2019133736 A1 | 7/2019 |
| WO | WO 2019133737 A1 | 7/2019 |
| WO | WO 2019133739 A1 | 7/2019 |
| WO | WO 2019133741 A1 | 7/2019 |
| WO | WO 2019133750 A1 | 7/2019 |
| WO | WO 2019133753 A1 | 7/2019 |
| WO | 2020257059 A1 | 12/2020 |
| WO | 2020257060 A1 | 12/2020 |
| WO | 2020257061 A1 | 12/2020 |
| WO | 2020257062 A1 | 12/2020 |
| WO | 2020257063 A1 | 12/2020 |

* cited by examiner

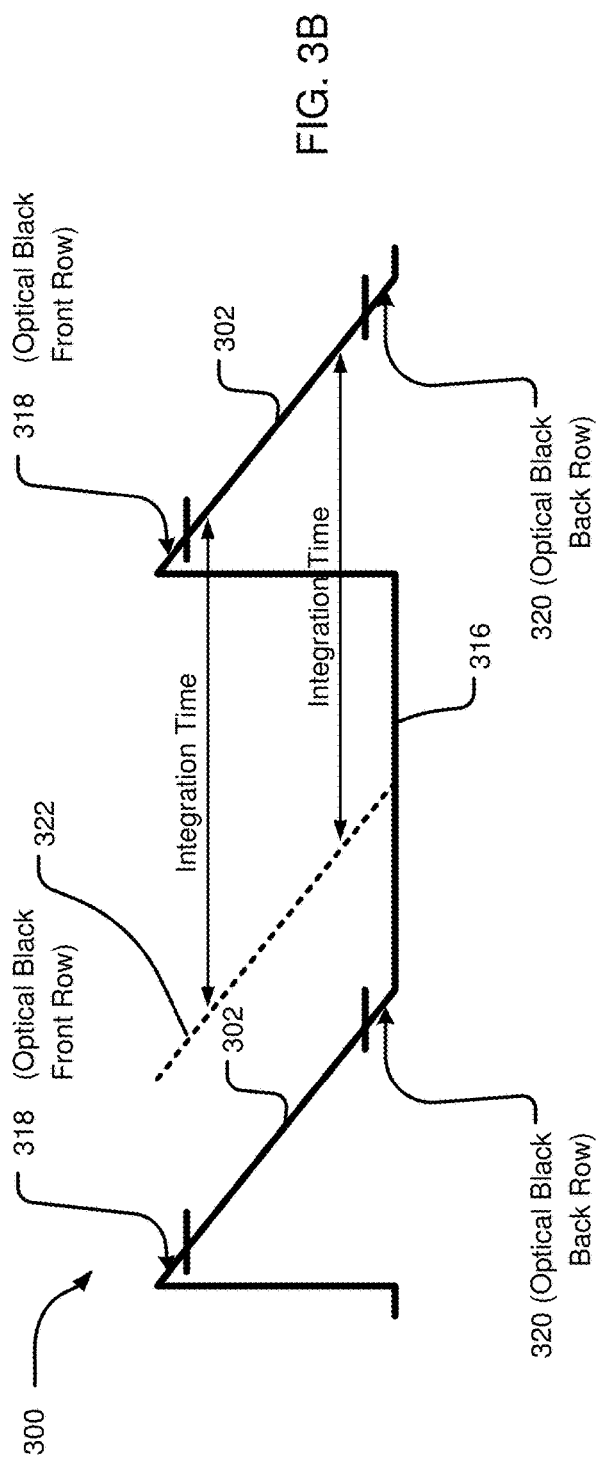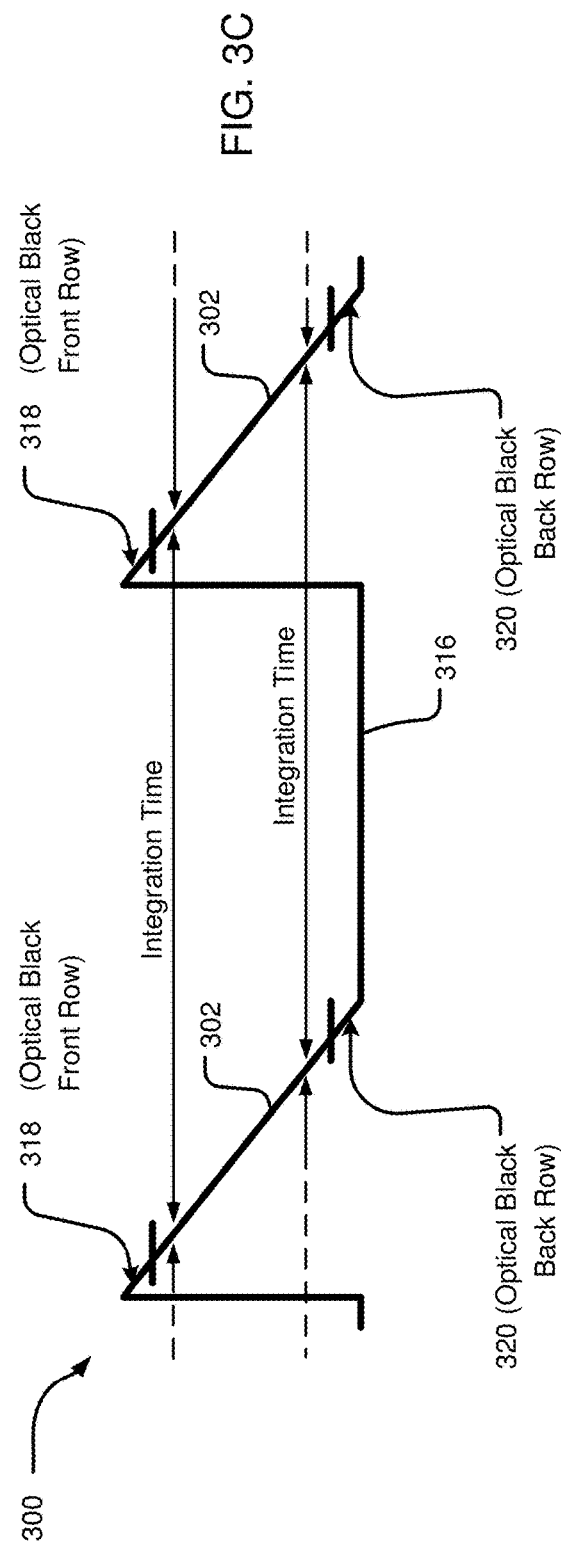

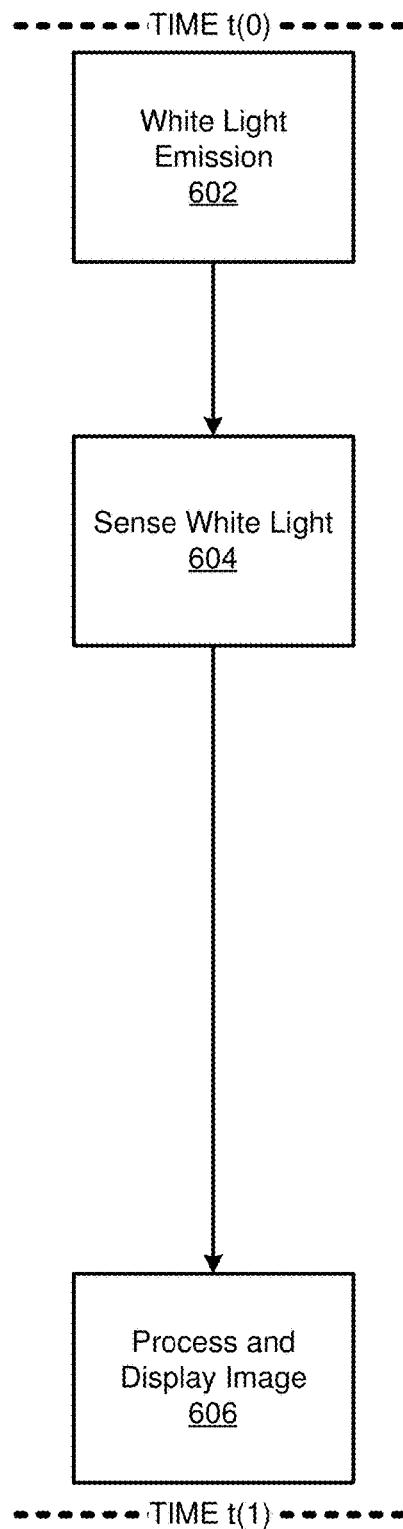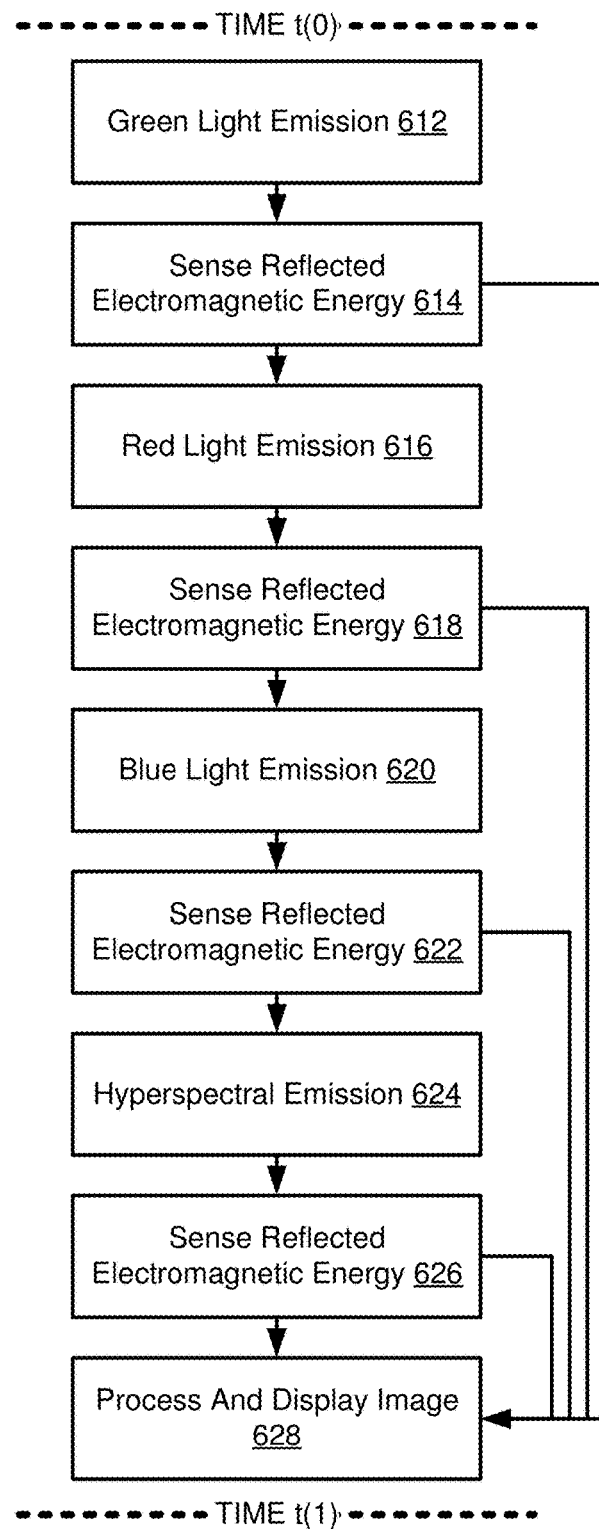
FIG. 6A
(Prior Art)
FIG. 6B

Switch cap voltage up-convertor

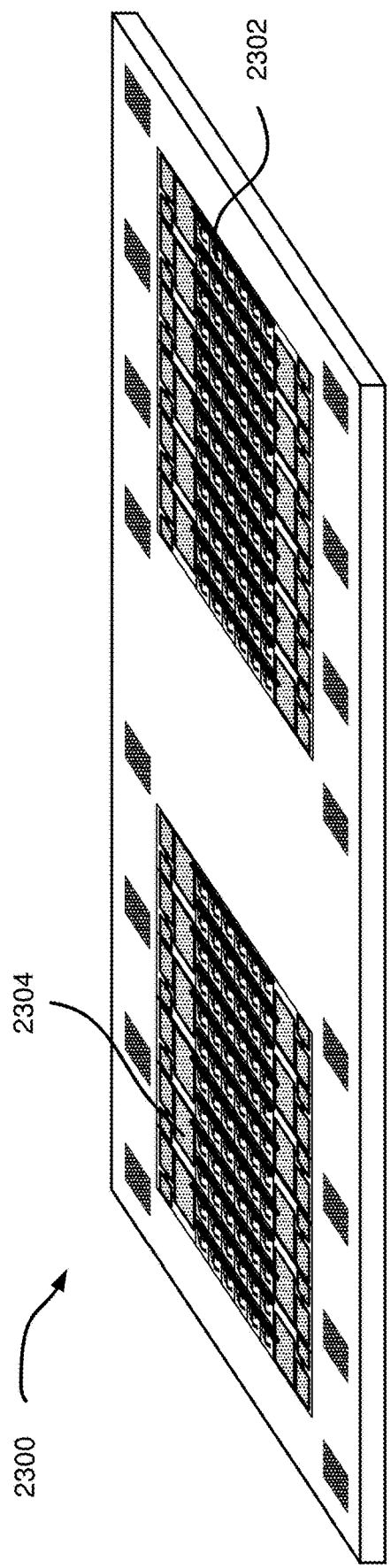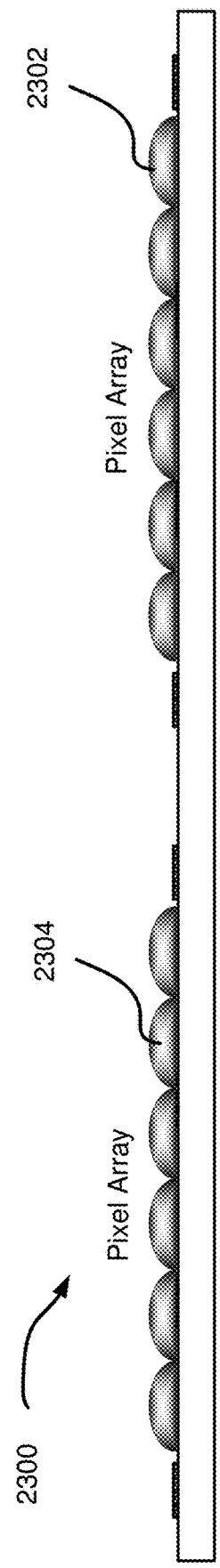
FIG. 23A
FIG. 23B
3D with double pixel array

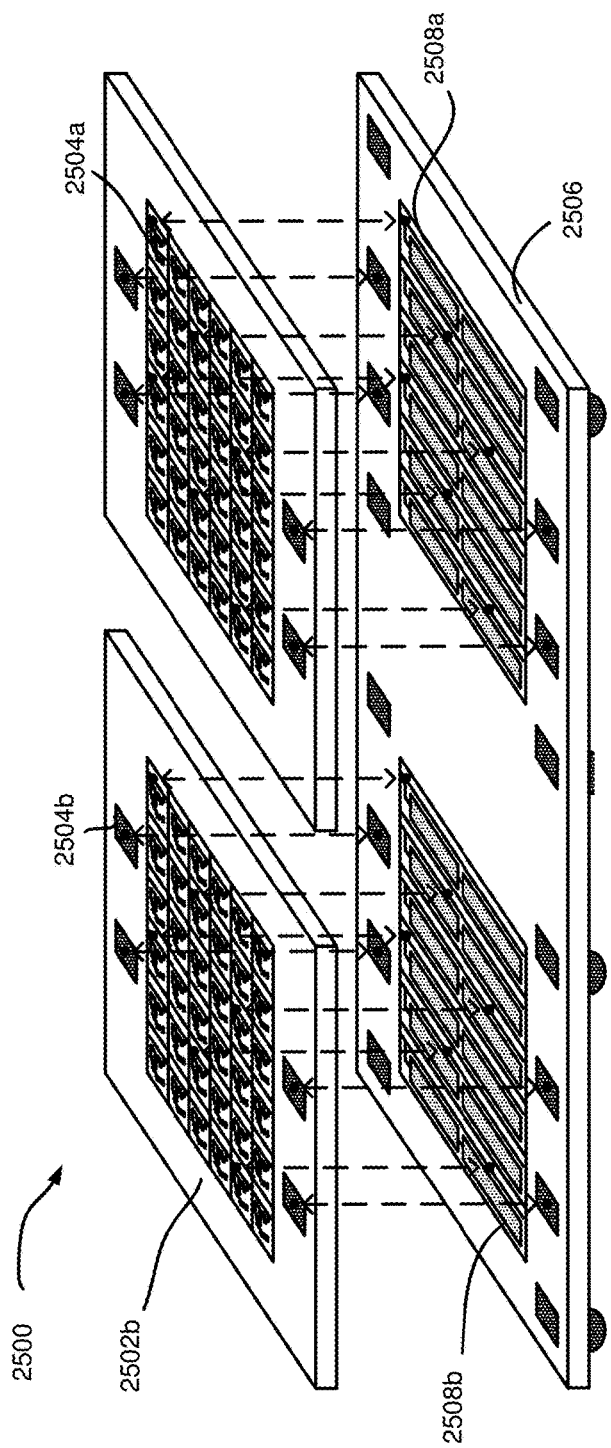
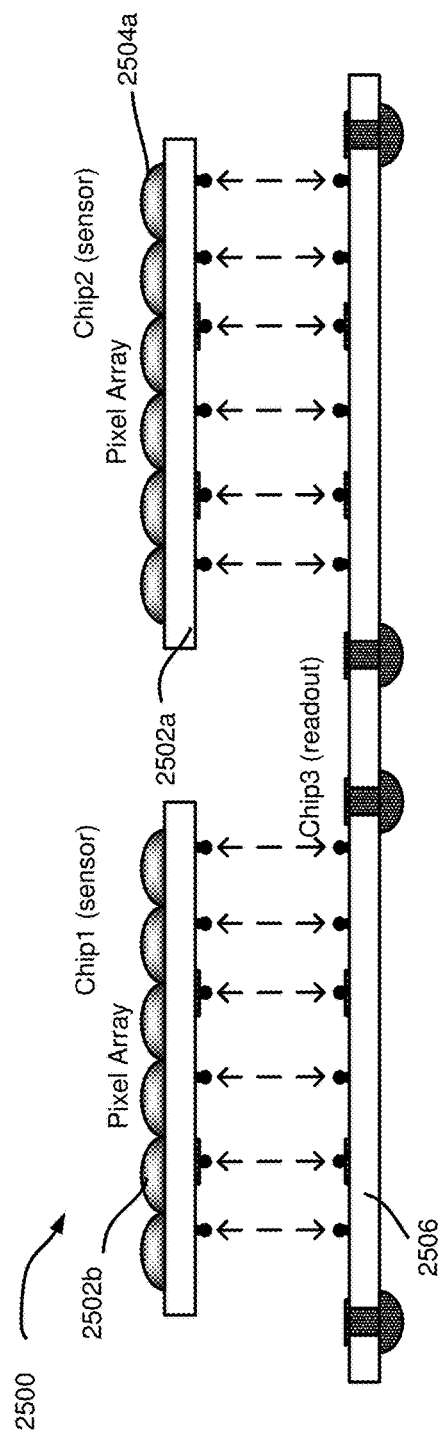
FIG. 25A
FIG. 25B

MINIMIZING IMAGE SENSOR INPUT/OUTPUT IN A PULSED HYPERSPECTRAL IMAGING SYSTEM

CROSS-REFERENCE TO RELATED APPLICATIONS

This application claims the benefit of U.S. Provisional Patent Application No. 62/864,234, filed Jun. 20, 2019, titled "MINIMIZE IMAGE SENSOR INPUT/OUTPUT IN AN ENDOSCOPIC IMAGING ENVIRONMENT FOR USE WITH HYPERSPECTRAL AND FLUORESCENCE IMAGING," which is incorporated herein by reference in its entirety, including but not limited to those portions that specifically appear hereinafter, the incorporation by reference being made with the following exception: In the event that any portion of the above-referenced provisional application is inconsistent with this application, this application supersedes the above-referenced provisional application.

TECHNICAL FIELD

This disclosure is directed to digital imaging and is particularly directed to hyperspectral imaging in a light deficient environment.

BACKGROUND

Advances in technology have provided advances in imaging capabilities for medical use. An endoscope may be used to look inside a body and examine the interior of an organ or cavity of the body. Endoscopes are used for investigating a patient's symptoms, confirming a diagnosis, or providing medical treatment. A medical endoscope may be used for viewing a variety of body systems and parts such as the gastrointestinal tract, the respiratory tract, the urinary tract, the abdominal cavity, and so forth. Endoscopes may further be used for surgical procedures such as plastic surgery procedures, procedures performed on joints or bones, procedures performed on the neurological system, procedures performed within the abdominal cavity, and so forth.

In some instances of endoscopic imaging, it may be beneficial or necessary to view a space in color. A digital color image includes at least three layers, or "color channels," that cumulatively form an image with a range of hues. Each of the color channels measures the intensity and chrominance of light for a spectral band. Commonly, a digital color image includes a color channel for red, green, and blue spectral bands of light (this may be referred to as a Red Green Blue or RGB image). Each of the red, green, and blue color channels include brightness information for the red, green, or blue spectral band of light. The brightness information for the separate red, green, and blue layers are combined to create the color image. Because a color image is made up of separate layers, a conventional digital camera image sensor includes a color filter array that permits red, green, and blue visible light wavelengths to hit selected pixel sensors. Each individual pixel sensor element is made sensitive to red, green, or blue wavelengths and will only return image data for that wavelength. The image data from the total array of pixel sensors is combined to generate the RGB image. The at least three distinct types of pixel sensors consume significant physical space such that the complete pixel array cannot fit in the small distal end of an endoscope.

Because a traditional image sensor cannot fit in the distal end of an endoscope, the image sensor is traditionally located in a handpiece unit of an endoscope that is held by an endoscope operator and is not placed within the body cavity. In such an endoscope, light is transmitted along the length of the endoscope from the handpiece unit to the distal end of the endoscope. This configuration has significant limitations. Endoscopes with this configuration are delicate and can be easily misaligned or damaged when bumped or impacted during regular use. This can significantly degrade the quality of the images and necessitate that the endoscope be frequently repaired or replaced.

The traditional endoscope with the image sensor placed in the handpiece unit is further limited to capturing only color images. However, in some implementations, it may be desirable to capture images with hyperspectral image data in addition to color image data. Color images reflect what the human eye detects when looking at an environment. However, the human eye is limited to viewing only visible light and cannot detect other wavelengths of the electromagnetic spectrum. At other wavelengths of the electromagnetic spectrum beyond the "visible light" wavelengths, additional information may be obtained about an environment. One means for obtaining image data outside the visible light spectrum is the application of hyperspectral imaging.

Hyperspectral imaging is used to identify different materials or objects and to identify different processes by providing information beyond what is visible to the human eye. Unlike a normal camera image that provides limited information to the human eye, hyperspectral imaging can identify specific compounds and biological processes based on the unique spectral signatures of the compounds and biological processes. Hyperspectral imaging is complex and can require fast computer processing capacity, sensitive detectors, and large data storage capacities.

Hyperspectral imaging traditionally requires specialized image sensors that consume significant physical space and cannot fit within the distal end of an endoscope. Further, if a hyperspectral image is overlaid on a black-and-white or color image to provide context to a practitioner, a camera (or multiples cameras) capable of generating the overlaid image may have many distinct types of pixel sensors that are sensitive to distinct ranges of electromagnetic radiation. This would include the three separate types of pixels sensors for generating an RGB color image along with additional pixel sensors for generating the hyperspectral image data at different wavelengths of the electromagnetic spectrum. This consumes significant physical space and necessitates a large pixel array to ensure the image resolution is satisfactory. In the case of endoscopic imaging, the camera or cameras would be too large to be placed at the distal end of the endoscope and may therefore be placed in an endoscope hand unit or robotic unit. This introduces the same disadvantages mentioned above and can cause the endoscope to be very delicate such that image quality is significantly degraded when the endoscope is bumped or impacted during use.

In light of the foregoing, described herein are systems, methods, and devices for improved endoscopic imaging in a light deficient environment. The systems, methods, and devices disclosed herein provide means for color and hyperspectral imaging with an endoscopic device.

BRIEF DESCRIPTION OF THE DRAWINGS

Non-limiting and non-exhaustive implementations of the disclosure are described with reference to the following figures, wherein like reference numerals refer to like parts throughout the various views unless otherwise specified.

Advantages of the disclosure will become better understood with regard to the following description and accompanying drawings where:

FIGS. 3A to 3D are illustrations of the operational cycles of a sensor used to construct an exposure frame;

FIG. 6A is a schematic diagram of a process for recording a video with full spectrum light over a period of time from t(0) to t(1);

FIG. 6B is a schematic diagram of a process for recording a video by pulsing portioned spectrum light over a period of time from t(0) to t(1);

FIGS. 23A and 23B illustrate an implementation having a plurality of pixel arrays for producing a three-dimensional image in accordance with the principles and teachings of the disclosure;

FIGS. 25A and 25B illustrate a perspective view and a side view, respectively, of an implementation of an imaging sensor having a plurality of pixel arrays for producing a three-dimensional image, wherein the plurality of pixel arrays and the image sensor are built on a plurality of substrates.

DETAILED DESCRIPTION

Figure 1:
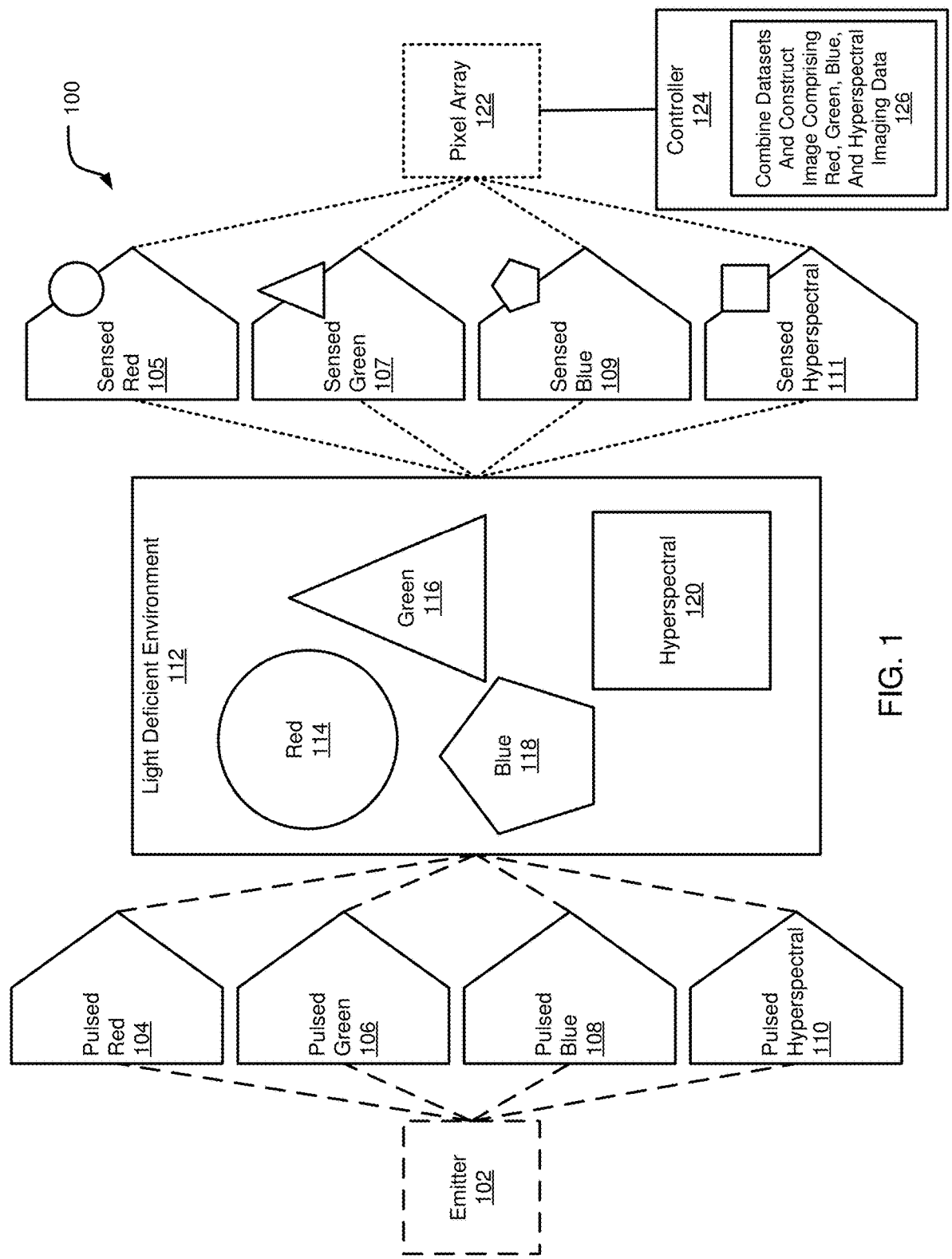
FIG. 1 is a schematic view of a system for digital imaging in a light deficient environment with a paired emitter and pixel array.

Disclosed herein are systems, methods, and devices for digital imaging that may be primarily suited to medical applications such as medical endoscopic imaging. An embodiment of the disclosure is an endoscopic system for hyperspectral and color imaging in a light deficient environment. Such methods, systems, and computer-based products disclosed herein provide imaging or diagnostic capabilities for use in medical robotics applications, such as the use of robotics for performing imaging procedures, surgical procedures, and the like.

Conventional endoscopes are designed such that the image sensor is placed at a proximal end of the device within a handpiece unit. This configuration requires that incident light travel the length of the endoscope by way of precisely coupled optical elements. The precise optical elements can easily be misaligned during regular use, and this can lead to image distortion or image loss. Embodiments of the disclosure place an image sensor within the highly space-constrained environment in the distal end of the endoscope itself. This provides greater optical simplicity when compared with implementations known in the art. However, an acceptable solution to this approach is by no means trivial and introduces its own set of engineering challenges.

There can be a noticeable loss to image quality when the overall size of an image sensor is minimized such that the image sensor can fit within the distal tip of an endoscope. The area of the pixel array of the image sensor can be reduced by reducing the number of pixels and/or the sensing area of each individual pixel. Each of these modifications impacts the resolution, sensitivity, and dynamic range of the resultant images. Traditional endoscopic imaging systems are geared toward sensing steady broadband illumination and providing color information by virtue of segmented pixel arrays such as the Bayer pattern array. In light of the deficiencies associated with segmented pixel arrays, disclosed herein are alternative systems and methods that use a monochromatic (may be referred to as "color agnostic") pixel array that does not include individual pixel filters. In the embodiments disclosed herein, the color information is provided by pulsing an emitter with different wavelengths of electromagnetic radiation. The pulsed imaging system disclosed herein can generate color images with hyperspectral imaging data overlaid thereon.

In an embodiment, the color information is determined by capturing independent exposure frames in response to pulses of different wavelengths of electromagnetic radiation. The alternative pulses may include red, green, and blue wavelengths for generating an RGB image frame consisting of a red exposure frame, a green exposure frame, and a blue exposure frame. In an alternative implementation, the alternative pulses may include luminance ("Y"), red chrominance ("Cr"), and blue chrominance "(Cb") pulses of light for generating a YCbCr image frame consisting of luminance data, red chrominance data, and blue chrominance data. The color image frame further may further data from a hyperspectral exposure frame overlaid on the RGB or YCbCr image frame. The hyperspectral pulse may include one or more pulses of electromagnetic radiation for eliciting a spectral response. In an embodiment, the hyperspectral emission includes one or more of electromagnetic radiation having a wavelength from about 513 nm to about 545 nm; from about 565 nm to about 585 nm; or from about 900 nm to about 1000 nm. Alternating the wavelengths of the pulsed electromagnetic radiation allows the full pixel array to be exploited and avoids the artifacts introduced by Bayer pattern pixel arrays.

In an embodiment, the overall size of the image sensor is further reduced by reducing the number of pads on the image sensor chip. A significant portion of total chip area is consumed by individual bond pads on the image sensor chip. Each bond pad provides power and input/output signals to and from the image sensor chip. In the systems and methods disclosed herein, the imaging sensor pad count is reduced by combining digital input and output functional into the same bidirectional pads. During image transmission, the bidirectional pads act as differential outputs. In an embodiment, during a defined portion of each exposure frame, the bidirectional pads switch direction to receive commands.

In some instances, it is desirable to generate endoscopic imaging with multiple data types or multiple images overlaid on one another. For example, it may be desirable to generate a color (RGB or YCbCr) image that further includes hyperspectral imaging data overlaid on the RGB image. An overlaid image of this nature may enable a medical practitioner or computer program to identify critical body structures based on the hyperspectral imaging data. Historically, this would require the use of multiple sensor systems including an image sensor for color imaging and one or more additional image sensors for hyperspectral imaging. In such systems, the multiple image sensors would have multiple types of pixel sensors that are each sensitive to distinct ranges of electromagnetic radiation. In systems known in the art, this includes the three separate types of pixel sensors for generating an RGB color image along with additional pixel sensors for generating the hyperspectral image data at different wavelengths of the electromagnetic spectrum. These multiple different pixel sensors consume a prohibitively large physical space and cannot be located at a distal tip of the endoscope. In systems known in the art, the camera or cameras are not placed at the distal tip of the endoscope and are instead placed in an endoscope handpiece or robotic unit. This introduces numerous disadvantages and causes the endoscope to be very delicate. The delicate endoscope may be damaged and image quality may be degraded when the endoscope is bumped or impacted during use. Considering the foregoing, disclosed herein are systems, methods, and devices for endoscopic imaging in a light deficient environment. The systems, methods, and devices disclosed herein provide means for employing multiple imaging techniques in a single imaging session while permitting one or more image sensors to be disposed in a distal tip of the endoscope.

Hyperspectral Imaging

In an embodiment, the systems, methods, and devices disclosed herein provide means for generating hyperspectral imaging data in a light deficient environment. Spectral imaging uses multiple bands across the electromagnetic spectrum. This is different from conventional cameras that only capture light across the three wavelengths based in the visible spectrum that are discernable by the human eye, including the red, green, and blue wavelengths to generate an RGB image. Spectral imaging may use any band of wavelengths in the electromagnetic spectrum, including infrared wavelengths, the visible spectrum, the ultraviolet spectrum, x-ray wavelengths, or any suitable combination of various wavelength bands.

Hyperspectral imaging was originally developed for applications in mining and geology. Unlike a normal camera image that provides limited information to the human eye, hyperspectral imaging can identify specific minerals based on the spectral signatures of the different minerals. Hyperspectral imaging can be useful even when captured in aerial images and can provide information about, for example, oil or gas leakages from pipelines or natural wells and their effects on nearby vegetation. This information is collected based on the spectral signatures of certain materials, objects, or processes that may be identified by hyperspectral imaging. Hyperspectral imaging is also useful in medical imaging applications where certain tissues, chemical processes, biological processes, and diseases can be identified based on unique spectral signatures.

In an embodiment of hyperspectral imaging, a complete spectrum or some spectral information is collected at every pixel in an image plane. A hyperspectral camera may use special hardware to capture any suitable number of wavelength bands for each pixel which may be interpreted as a complete spectrum. The goal of hyperspectral imaging varies for different applications. In one application, the goal is to obtain imaging data for the entire electromagnetic spectrum for each pixel in an image scene. In another application, the goal is to obtain imaging data for certain partitions of the electromagnetic spectrum for each pixel in an image scene. The certain partitions of the electromagnetic spectrum may be selected based on what might be identified in the image scene. These applications enable certain materials, tissues, chemical processes, biological processes, and diseases to be identified with precision when those materials or tissues might not be identifiable under the visible light wavelength bands. In some medical applications, hyperspectral imaging includes one or more specific partitions of the electromagnetic spectrum that have been selected to identify certain tissues, diseases, chemical processes, and so forth.

Some example partitions of the electromagnetic spectrum that may be pulsed for hyperspectral imaging in a medical application include electromagnetic radiation having a wavelength from about 513 nm to about 545 nm; from about 565 nm to about 585 nm; and/or from about 900 nm to about 1000 nm.

Hyperspectral imaging enables numerous advantages over conventional imaging and enables particular advantages in medical applications. Endoscopic hyperspectral imaging permits a health practitioner or computer-implemented program to identify nervous tissue, muscle tissue, vessels, cancerous cells, typical non-cancerous cells, the direction of blood flow, and more. Hyperspectral imaging enables atypical cancerous tissue to be precisely differentiated from typical healthy tissue and may therefore enable a practitioner or computer-implemented program to discern the boundary of a cancerous tumor during an operation or investigative imaging. The information obtained by hyperspectral imaging enables the precise identification of certain tissues or conditions that may lead to diagnoses that may not be possible or may be less accurate if using conventional imaging. Additionally, hyperspectral imaging may be used during medical procedures to provide image-guided surgery that enables a medical practitioner to, for example, view tissues located behind certain tissues or fluids, identify atypical cancerous cells in contrast with typical healthy cells, identify certain tissues or conditions, identify critical structures, and so forth. Hyperspectral imaging provides specialized diagnostic information about tissue physiology, morphology, and composition that cannot be generated with conventional imaging.

In an embodiment of the disclosure, an endoscopic system illuminates a source and pulses electromagnetic radiation for spectral or hyperspectral imaging. The pulsed hyperspectral imaging discussed herein includes pulsing one or more bands of the electromagnetic spectrum, and may include infrared wavelengths, the visible spectrum, the ultraviolet spectrum, x-ray wavelengths, or any suitable combination of various wavelength bands. In an embodiment, hyperspectral imaging includes pulsing electromagnetic radiation having a wavelength from about 513 nm to about 545 nm; from about 565 nm to about 585 nm; and/or from about 900 nm to about 1000 nm.

Pulsed Imaging

Some implementations of the disclosure include aspects of a combined sensor and system design that allows for high definition imaging with reduced pixel counts in a controlled illumination environment. This is accomplished with frame-by-frame pulsing of a single-color wavelength and switching or alternating each frame between a single, different color wavelength using a controlled light source in conjunction with high frame capture rates and a specially designed corresponding monochromatic sensor. Additionally, electromagnetic radiation outside the visible light spectrum may be pulsed to enable the generation of a hyperspectral image. The pixels may be color agnostic such that each pixel generates data for each pulse of electromagnetic radiation, including pulses for red, green, and blue visible light wavelengths along with other wavelengths used for hyperspectral imaging.

A system of the disclosure is an endoscopic imaging system for use in a light deficient environment. The system includes an endoscope comprising an image sensor, wherein the image sensor is configured to sense reflected electromagnetic radiation for generating a plurality of exposure frames that can be combined to generate an RGB image frame with hyperspectral data overlaid thereon. The system includes an emitter for emitting pulses of electromagnetic radiation. The system includes a controller (may alternatively be referred to as a "control circuit" in electronic communication with the image sensor and the emitter. The controller controls a duty cycle of the emitter in response to signals corresponding to a duty cycle of the emitter. The image sensor includes bidirectional pads that can send and receive information. The bidirectional pads of the image sensor operate in a frame period divided into three defined states, including a rolling readout state, a service line state, and a configuration state. The system includes an oscillator disposed in the controller and a frequency detector connected to the controller. The frequency detector controls a clock frequency of the image sensor in response to signals from the controller that correspond to the frequency of the oscillator. The system is such that clock signal data is transmitted from the bidirectional pads of the image sensor to the controller during the service line phase and the configuration phase. The system is such that exposure frames are synchronized without the use of an input clock or a data transmission clock.

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

Before the structure, systems and methods for producing an image in a light deficient environment are disclosed and described, it is to be understood that this disclosure is not limited to the particular structures, configurations, process steps, and materials disclosed herein as such structures, configurations, process steps, and materials may vary somewhat. It is also to be understood that the terminology employed herein is used for the purpose of describing particular embodiments only and is not intended to be limiting since the scope of the disclosure will be limited only by the appended claims and equivalents thereof.

In describing and claiming the subject matter of the disclosure, the following terminology will be used in accordance with the definitions set out below.

It must be noted that, as used in this specification and the appended claims, the singular forms "a," "an," and "the" include plural referents unless the context clearly dictates otherwise.

As used herein, the terms "comprising," "including," "containing," "characterized by," and grammatical equivalents thereof are inclusive or open-ended terms that do not exclude additional, unrecited elements or method steps.

As used herein, the phrase "consisting of" and grammatical equivalents thereof exclude any element or step not specified in the claim.

As used herein, the phrase "consisting essentially of" and grammatical equivalents thereof limit the scope of a claim to the specified materials or steps and those that do not materially affect the basic and novel characteristic or characteristics of the claimed disclosure.

As used herein, the term "proximal" shall refer broadly to the concept of a portion nearest an origin.

As used herein, the term "distal" shall generally refer to the opposite of proximal, and thus to the concept of a portion farther from an origin, or a furthest portion, depending upon the context.

As used herein, color sensors or multi spectrum sensors are those sensors known to have a color filter array (CFA) thereon to filter the incoming electromagnetic radiation into its separate components. In the visual range of the electromagnetic spectrum, such a CFA may be built on a Bayer pattern or modification thereon to separate green, red and blue spectrum components of the light.

As used herein, monochromatic sensor refers to an unfiltered imaging sensor. Since the pixels are color agnostic, the effective spatial resolution is appreciably higher than for their color (typically Bayer-pattern filtered) counterparts in conventional single-sensor cameras. Monochromatic sensors may also have higher quantum efficiency because fewer incident photons are wasted between individual pixels.

As used herein, an emitter is a device that is capable of generating and emitting electromagnetic pulses. Various embodiments of emitters may be configured to emit pulses and have very specific frequencies or ranges of frequencies from within the entire electromagnetic spectrum. Pulses may comprise wavelengths from the visible and non-visible ranges. An emitter may be cycled on and off to produce a pulse or may produce a pulse with a shutter mechanism. An emitter may have variable power output levels or may be controlled with a secondary device such as an aperture or filter. An emitter may emit broad spectrum or full spectrum electromagnetic radiation that may produce pulses through color filtering or shuttering. An emitter may comprise a plurality of electromagnetic sources that act individually or in concert.

It should be noted that as used herein the term "light" is both a particle and a wavelength and is intended to denote electromagnetic radiation that is detectable by a pixel array 122 and may include wavelengths from the visible and non-visible spectrums of electromagnetic radiation. The term "partition" is used herein to mean a pre-determined range of wavelengths of the electromagnetic spectrum that is less than the entire spectrum, or in other words, wavelengths that make up some portion of the electromagnetic spectrum. As used herein, an emitter is a light source that may be controllable as to the portion of the electromagnetic spectrum that is emitted or that may operate as to the physics of its components, the intensity of the emissions, or the duration of the emission, or all the above. An emitter may emit light in any dithered, diffused, or collimated emission and may be controlled digitally or through analog methods or systems. As used herein, an electromagnetic emitter is a source of a burst of electromagnetic energy and includes light sources, such as lasers, LEDs, incandescent light, or any light source that can be digitally controlled.

Referring now to the figures, FIG. 1 illustrates a schematic diagram of a system 100 for sequential pulsed imaging in a light deficient environment. The system 100 can be deployed to generate an RGB image with hyperspectral data overlaid on the RGB image. The system 100 includes an emitter 102 and a pixel array 122. The emitter 102 pulses a partition of electromagnetic radiation in the light deficient environment 112 and the pixel array 122 senses instances of reflected electromagnetic radiation. The emitter 102 and the pixel array 122 work in sequence such that one or more pulses of a partition of electromagnetic radiation results in an exposure frame comprising image data sensed by the pixel array 122.

A pixel array 122 of an image sensor may be paired with the emitter 102 electronically, such that the emitter 102 and the pixel array 122 are synced during operation for both receiving the emissions and for the adjustments made within the system. The emitter 102 may be tuned to emit electromagnetic radiation in the form of a laser, which may be pulsed to illuminate a light deficient environment 112. The emitter 102 may pulse at an interval that corresponds to the operation and functionality of the pixel array 122. The emitter 102 may pulse light in a plurality of electromagnetic partitions such that the pixel array receives electromagnetic energy and produces a dataset that corresponds in time with each specific electromagnetic partition. For example, FIG. 1 illustrates an implementation wherein the emitter 102 emits four different partitions of electromagnetic radiation, including red 104, green 106, blue 108 wavelengths, and a hyperspectral 110 emission. The hyperspectral 110 emission may include a band of wavelengths in the electromagnetic spectrum that elicit a spectral response. The hyperspectral 110 emission may include multiple separate emissions that are separate and independent from one another.

In an alternative embodiment not illustrated in FIG. 1, the pulsed emissions of light include a luminance ("Y") emission, a red chrominance ("Cr") emission, and a blue chrominance ("Cb") emission in place of the pulsed red 104, pulsed green 106, and pulsed blue 108 emissions. In an embodiment, the controller or the emitter 102 modules the pulses of electromagnetic radiation to provide luminance and/or chrominance information according to color transformation coefficients that convert light energy from red, green, and blue light energy spaces to luminance, red chrominance, and blue chrominance light energy space. The pulsed emissions of light may further include modulated blue chrominance ("λY+Cb") pulses and/or modulated red chrominance ("δY+Cr") pulses.

The light deficient environment 112 includes structures, tissues, and other elements that reflect a combination of red 114, green 116, and/or blue 118 light. A structure that is perceived as being red 114 will reflect back pulsed red 104 light. The reflection off the red structure results in sensed red 105 by the pixel array 122 following the pulsed red 104 emission. The data sensed by the pixel array 122 results in a red exposure frame. A structure that is perceived as being green 116 will reflect back pulsed green 106 light. The reflection off the green structure results in sensed green 107 by the pixel array 122 following the pulsed green 106 emission. The data sensed by the pixel array 122 results in a green exposure frame. A structure that is perceived as being blue 118 will reflect back pulsed blue 108 light. The reflection off the blue structure results in sensed blue 109 by the pixel array 122 following the pulsed blue 108 emission. The data sensed by the pixel array 122 results in a blue exposure frame.

When a structure is a combination of colors, the structure will reflect back a combination of the pulsed red 104, pulsed green 106, and/or pulsed blue 108 emissions. For example, a structure that is perceived as being purple will reflect back light from the pulsed red 104 and pulsed blue 108 emissions. The resulting data sensed by the pixel array 122 will indicate that light was reflected in the same region following the pulsed red 104 and pulsed blue 108 emissions. When the resultant red exposure frame and blue exposure frames are combined to form the RGB image frame, the RGB image frame will indicate that the structure is purple.

In an embodiment where the light deficient environment 112 includes a fluorescent reagent or dye or includes one or more fluorescent structures, tissues, or other elements, the pulsing scheme may include the emission of a certain fluorescence excitation wavelength. The certain fluorescence excitation wavelength may be selected to fluoresce a known fluorescent reagent, dye, or other structure. The fluorescent structure will be sensitive to the fluorescence excitation wavelength and will emit a fluorescence relaxation wavelength. The fluorescence relaxation wavelength will be sensed by the pixel array 122 following the emission of the fluorescence excitation wavelength. The data sensed by the pixel array 122 results in a fluorescence exposure frame. The fluorescence exposure frame may be combined with multiple other exposure frames to form an image frame. The data in the fluorescence exposure frame may be overlaid on an RGB image frame that includes data from a red exposure frame, a green exposure frame, and a blue exposure frame.

In an embodiment where the light deficient environment 112 includes structures, tissues, or other materials that emit a spectral response to certain partitions of the electromagnetic spectrum, the pulsing scheme may include the emission of a hyperspectral partition of electromagnetic radiation for the purpose of eliciting the spectral response from the structures, tissues, or other materials present in the light deficient environment 112. The spectral response includes the emission or reflection of certain wavelengths of electromagnetic radiation. The spectral response can be sensed by the pixel array 122 and result in a hyperspectral exposure frame. The hyperspectral exposure frame may be combined with multiple other exposure frames to form an image frame. The data in the hyperspectral exposure frame may be overlaid on an RGB image frame that includes data from a red exposure frame, a green exposure frame, and a blue exposure frame.

In an embodiment, the pulsing scheme includes the emission of a laser mapping or tool tracking pattern. The reflected electromagnetic radiation sensed by the pixel array 122 following the emission of the laser mapping or tool tracking pattern results in a laser mapping exposure frame. The data in the laser mapping exposure frame may be provided to a corresponding system to identify, for example, distances between tools present in the light deficient environment 112, a three-dimensional surface topology of a scene in the light deficient environment 112, distances, dimensions, or positions of structures or objects within the scene, and so forth. This data may be overlaid on an RGB image frame or otherwise provided to a user of the system.

The emitter 102 may be a laser emitter that is capable of emitting pulsed red 104 light for generating sensed red 105 data for identifying red 114 elements within the light deficient environment 112. The emitter 102 is further capable of emitting pulsed green 106 light for generating sensed green 107 data for identifying green 116 elements within the light deficient environment. The emitter 102 is further capable of emitting pulsed blue 108 light for generating sensed blue 109 data for identifying blue 118 elements within the light deficient environment. The emitter 102 is further capable of emitting a hyperspectral 110 emission for identifying elements sensitive to hyperspectral 120 radiation. The emitter 102 is capable of emitting the pulsed red 104, pulsed green 106, pulsed blue 108, and pulsed hyperspectral 110 emissions in any desired sequence.

The pixel array 122 senses reflected electromagnetic radiation. Each of the sensed red 105, the sensed green 107, the sensed blue 109, and the sensed hyperspectral 111 data can be referred to as an "exposure frame." The sensed hyperspectral 111 may result in multiple separate exposure frames that are separate and independent from one another.

For example, the sensed hyperspectral 111 may result in a first hyperspectral exposure frame at a first partition of electromagnetic radiation, a second hyperspectral exposure frame at a second partition of electromagnetic radiation, and so forth. Each exposure frame is assigned a specific color or wavelength partition, wherein the assignment is based on the timing of the pulsed color or wavelength partition from the emitter 102. The exposure frame in combination with the assigned specific color or wavelength partition may be referred to as a dataset. Even though the pixels 122 are not color-dedicated, they can be assigned a color for any given dataset based on a priori information about the emitter.

For example, during operation, after pulsed red 104 light is pulsed in the light deficient environment 112, the pixel array 122 senses reflected electromagnetic radiation. The reflected electromagnetic radiation results in an exposure frame, and the exposure frame is catalogued as sensed red 105 data because it corresponds in time with the pulsed red 104 light. The exposure frame in combination with an indication that it corresponds in time with the pulsed red 104 light is the "dataset." This is repeated for each partition of electromagnetic radiation emitted by the emitter 102. The data created by the pixel array 122 includes the sensed red 105 exposure frame identifying red 114 components in the light deficient environment and corresponding in time with the pulsed red 104 light. The data further includes the sensed green 107 exposure frame identifying green 116 components in the light deficient environment and corresponding in time with the pulsed green 106 light. The data further includes the sensed blue 109 exposure frame identifying blue 118 components in the light deficient environment and corresponding in time with the pulsed blue 108 light. The data further includes the sensed hyperspectral 111 exposure frame identifying the elements sensitive to hyperspectral 120 radiation and corresponding in time with the hyperspectral 110 emission.

In one embodiment, three datasets representing RED, GREEN and BLUE electromagnetic pulses are combined to form a single image frame. Thus, the information in a red exposure frame, a green exposure frame, and a blue exposure frame are combined to form a single RGB image frame. One or more additional datasets representing other wavelength partitions may be overlaid on the single RGB image frame. The one or more additional datasets may represent, for example, laser mapping data, fluorescence imaging data, and/or hyperspectral imaging data.

It will be appreciated that the disclosure is not limited to any particular color combination or any particular electromagnetic partition, and that any color combination or any electromagnetic partition may be used in place of RED, GREEN and BLUE, such as Cyan, Magenta and Yellow; Ultraviolet; infrared; any combination of the foregoing, or any other color combination, including all visible and non-visible wavelengths, without departing from the scope of the disclosure. In the figure, the light deficient environment 112 to be imaged includes red 114, green 116, and blue 118 portions, and further includes elements sensitive to hyperspectral 120 radiation that can be sensed and mapped into a three-dimensional rendering. As illustrated in the figure, the reflected light from the electromagnetic pulses only contains the data for the portion of the object having the specific color that corresponds to the pulsed color partition. Those separate color (or color interval) datasets can then be used to reconstruct the image by combining the datasets at 126. The information in each of the multiple exposure frames (i.e., the multiple datasets) may be combined by a controller 124, a control circuit, a camera controller, the image sensor, an image signal processing pipeline, or some other computing resource that is configurable to process the multiple exposure frames and combine the datasets at 126. As discussed herein, the controller 124 may include the structures and functions of a control circuit, a camera controller, and/or an image signal processing pipeline. The datasets may be combined to generate the single image frame within the endoscope unit itself or offsite by some other processing resource.

Figure 2:
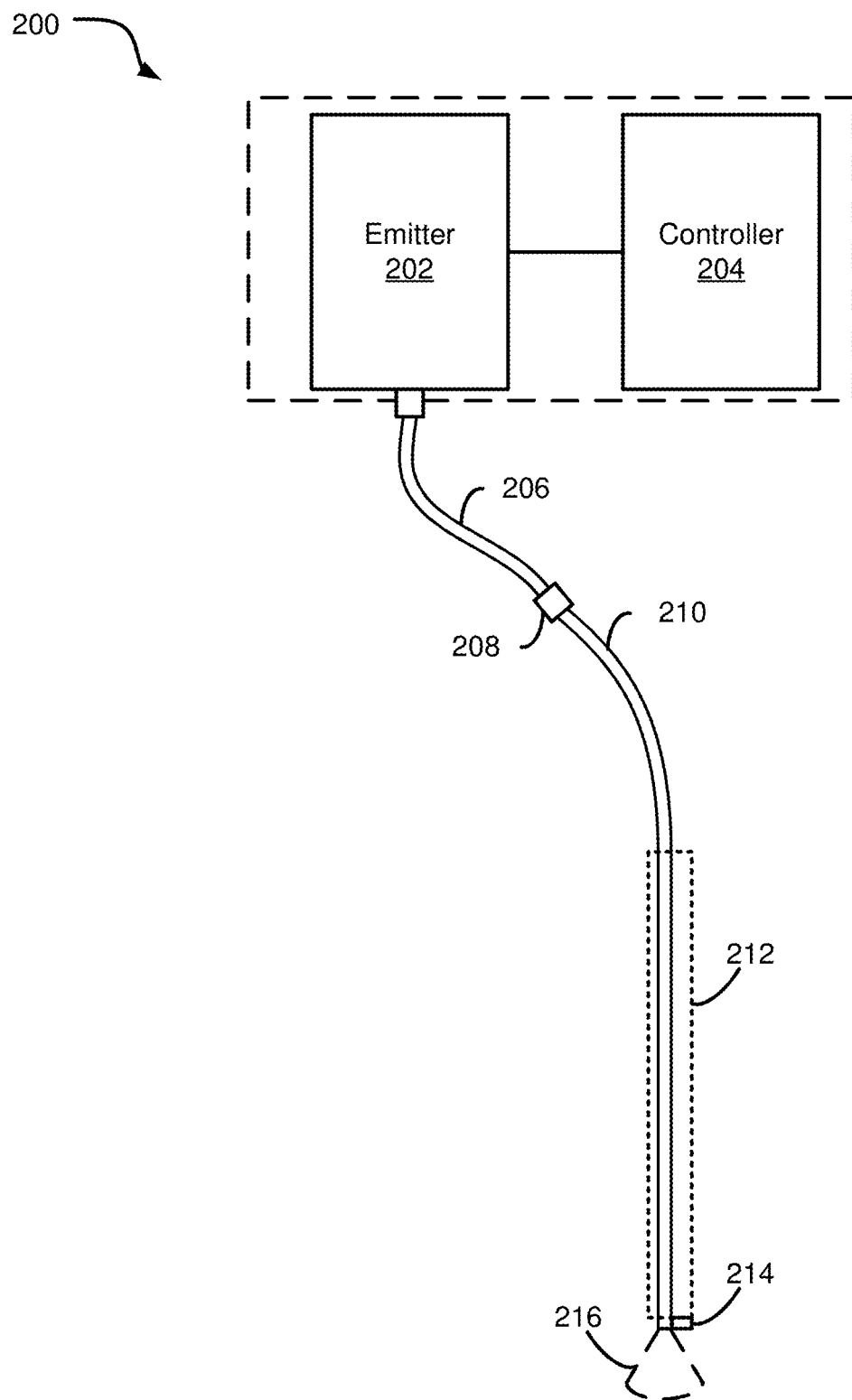
FIG. 2 is a system for providing illumination to a light deficient environment for endoscopic imaging.

FIG. 2 is a system 200 for providing illumination to a light deficient environment, such as for endoscopic imaging. The system 200 may be used in combination with any of the systems, methods, or devices disclosed herein. The system 200 includes an emitter 202, a controller 204, a jumper waveguide 206, a waveguide connector 208, a lumen waveguide 210, a lumen 212, and an image sensor 214 with accompanying optical components (such as a lens). The emitter 202 (may be generically referred to as a "light source") generates light that travels through the jumper waveguide 206 and the lumen waveguide 210 to illuminate a scene at a distal end of the lumen 212. The emitter 202 may be used to emit any wavelength of electromagnetic energy including visible wavelengths, infrared, ultraviolet, hyperspectral, fluorescence excitation, laser mapping pulsing schemes, or other wavelengths. The lumen 212 may be inserted into a patient's body for imaging, such as during a procedure or examination. The light is output as illustrated by dashed lines 216. A scene illuminated by the light may be captured using the image sensor 214 and displayed for a doctor or some other medical personnel. The controller 204 may provide control signals to the emitter 202 to control when illumination is provided to a scene. In one embodiment, the emitter 202 and controller 204 are located within a camera controller (CCU) or external console to which an endoscope is connected. If the image sensor 214 includes a CMOS sensor, light may be periodically provided to the scene in a series of illumination pulses between readout periods of the image sensor 214 during what is known as a blanking period. Thus, the light may be pulsed in a controlled manner to avoid overlapping into readout periods of the image pixels in a pixel array of the image sensor 214.

In one embodiment, the lumen waveguide 210 includes one or more optical fibers. The optical fibers may be made of a low-cost material, such as plastic to allow for disposal of the lumen waveguide 210 and/or other portions of an endoscope. In one embodiment, the lumen waveguide 210 is a single glass fiber having a diameter of 500 microns. The jumper waveguide 206 may be permanently attached to the emitter 202. For example, a jumper waveguide 206 may receive light from an emitter within the emitter 202 and provide that light to the lumen waveguide 210 at the location of the connector 208. In one embodiment, the jumper waveguide 106 includes one or more glass fibers. The jumper waveguide may include any other type of waveguide for guiding light to the lumen waveguide 210. The connector 208 may selectively couple the jumper waveguide 206 to the lumen waveguide 210 and allow light within the jumper waveguide 206 to pass to the lumen waveguide 210. In one embodiment, the lumen waveguide 210 is directly coupled to a light source without any intervening jumper waveguide 206.

The image sensor 214 includes a pixel array. In an embodiment, the image sensor 214 includes two or more pixel arrays for generating a three-dimensional image. The image sensor 214 may constitute two more image sensors that each have an independent pixel array and can operate independent of one another. The pixel array of the image sensor 214 includes active pixels and optical black ("OB") or optically blind pixels. The active pixels may be clear "color agnostic" pixels that are capable of sensing imaging data for any wavelength of electromagnetic radiation. The optical black pixels are read during a blanking period of the pixel array when the pixel array is "reset" or calibrated. In an embodiment, light is pulsed during the blanking period of the pixel array when the optical black pixels are being read. After the optical black pixels have been read, the active pixels are read during a readout period of the pixel array. The active pixels may be charged by the electromagnetic radiation that is pulsed during the blanking period such that the active pixels are ready to be read by the image sensor during the readout period of the pixel array.

Figure 2A:
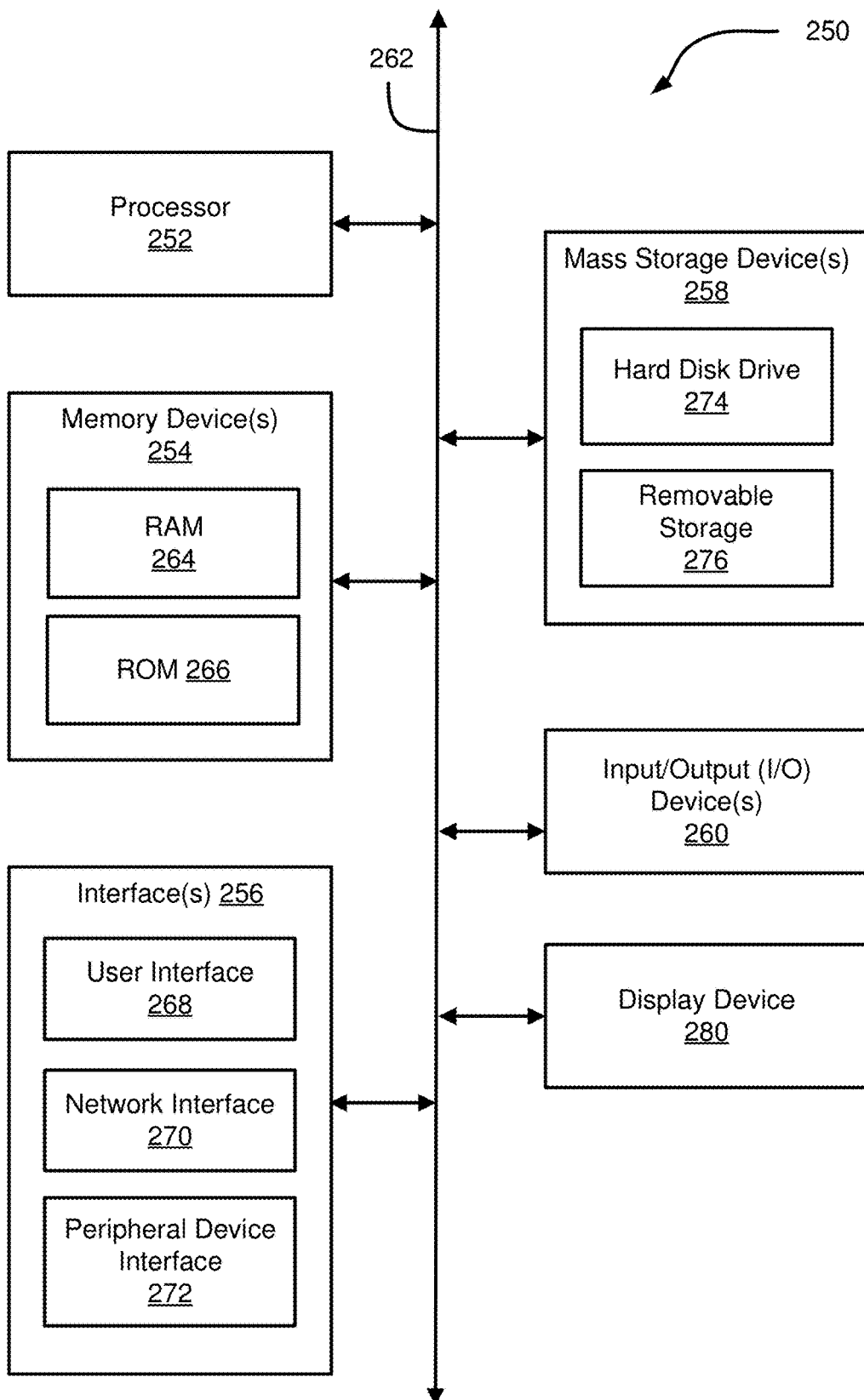
FIG. 2A is a schematic diagram of complementary system hardware.

FIG. 2A is a schematic diagram of complementary system hardware such as a special purpose or general-purpose computer. Implementations within the scope of the present disclosure may also include physical and other non-transitory computer readable media for carrying or storing computer executable instructions and/or data structures. Such computer readable media can be any available media that can be accessed by a general purpose or special purpose computer system. Computer readable media that stores computer executable instructions are computer storage media (devices). Computer readable media that carry computer executable instructions are transmission media. Thus, by way of example, and not limitation, implementations of the disclosure can comprise at least two distinctly different kinds of computer readable media: computer storage media (devices) and transmission media.

Computer storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium which can be used to store desired program code means in the form of computer executable instructions or data structures and which can be accessed by a general purpose or special purpose computer.

A "network" is defined as one or more data links that enable the transport of electronic data between computer systems and/or modules and/or other electronic devices. In an implementation, a sensor and camera controller may be networked to communicate with each other, and other components, connected over the network to which they are connected. When information is transferred or provided over a network or another communications connection (either hardwired, wireless, or a combination of hardwired or wireless) to a computer, the computer properly views the connection as a transmission medium. Transmissions media can include a network and/or data links, which can be used to carry desired program code means in the form of computer executable instructions or data structures and which can be accessed by a general purpose or special purpose computer. Combinations of the above should also be included within the scope of computer readable media.

Further, upon reaching various computer system components, program code means in the form of computer executable instructions or data structures that can be transferred automatically from transmission media to computer storage media (devices) (or vice versa). For example, computer executable instructions or data structures received over a network or data link can be buffered in RAM within a network interface module (e.g., a "NIC"), and then eventually transferred to computer system RAM and/or to less volatile computer storage media (devices) at a computer system. RAM can also include solid state drives (SSDs or PCIx based real time memory tiered storage, such as FusionIO). Thus, it should be understood that computer storage media (devices) can be included in computer system components that also (or even primarily) utilize transmission media.

Computer executable instructions comprise, for example, instructions and data which, when executed by one or more processors, cause a general-purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the disclosure may be practiced in network computing environments with many types of computer system configurations, including, personal computers, desktop computers, laptop computers, message processors, controllers, camera controllers, handheld devices, hand pieces, multi-processor systems, microprocessor-based or programmable consumer electronics, network PCs, minicomputers, mainframe computers, mobile telephones, PDAs, tablets, pagers, routers, switches, various storage devices, and the like. It should be noted that any of the above-mentioned computing devices may be provided by or located within a brick and mortar location. The disclosure may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Further, where appropriate, functions described herein can be performed in one or more of: hardware, software, firmware, digital components, or analog components. For example, one or more application specific integrated circuits (ASICs) or field programmable gate arrays (FPGAs) can be programmed to carry out one or more of the systems and procedures described herein. Certain terms are used throughout the following description and Claims to refer to particular system components. As one skilled in the art will appreciate, components may be referred to by different names. This document does not intend to distinguish between components that differ in name, but not function.

FIG. 2A is a block diagram illustrating an example computing device 250. Computing device 250 may be used to perform various procedures, such as those discussed herein. Computing device 250 can function as a server, a client, or any other computing entity. Computing device 250 can perform various monitoring functions as discussed herein, and can execute one or more application programs, such as the application programs described herein. Computing device 250 can be any of a wide variety of computing devices, such as a desktop computer, a notebook computer, a server computer, a handheld computer, camera controller, tablet computer and the like.

Computing device 250 includes one or more processor(s) 252, one or more memory device(s) 254, one or more interface(s) 256, one or more mass storage device(s) 258, one or more Input/Output (I/O) device(s) 260, and a display device 280 all of which are coupled to a bus 262. Processor(s) 252 include one or more processors or controllers that execute instructions stored in memory device(s) 254 and/or mass storage device(s) 258. Processor(s) 252 may also include various types of computer readable media, such as cache memory.

Memory device(s) 254 include various computer readable media, such as volatile memory (e.g., random access memory (RAM) 264) and/or nonvolatile memory (e.g., read-only memory (ROM) 266). Memory device(s) 254 may also include rewritable ROM, such as Flash memory.

Mass storage device(s) 258 include various computer readable media, such as magnetic tapes, magnetic disks, optical disks, solid-state memory (e.g., Flash memory), and so forth. As shown in FIG. 2, a particular mass storage device is a hard disk drive 274. Various drives may also be included in mass storage device(s) 258 to enable reading from and/or writing to the various computer readable media. Mass storage device(s) 258 include removable media 276 and/or non-removable media.

I/O device(s) 260 include various devices that allow data and/or other information to be input to or retrieved from computing device 250. Example I/O device(s) 260 include digital imaging devices, electromagnetic sensors and emitters, cursor control devices, keyboards, keypads, microphones, monitors or other display devices, speakers, printers, network interface cards, modems, lenses, CCDs or other image capture devices, and the like.

Display device 280 includes any type of device capable of displaying information to one or more users of computing device 250. Examples of display device 280 include a monitor, display terminal, video projection device, and the like.

Interface(s) 256 include various interfaces that allow computing device 250 to interact with other systems, devices, or computing environments. Example interface(s) 256 may include any number of different network interfaces 270, such as interfaces to local area networks (LANs), wide area networks (WANs), wireless networks, and the Internet. Other interface(s) include user interface 268 and peripheral device interface 272. The interface(s) 256 may also include one or more user interface elements 268. The interface(s) 256 may also include one or more peripheral interfaces such as interfaces for printers, pointing devices (mice, track pad, etc.), keyboards, and the like.

Bus 262 allows processor(s) 252, memory device(s) 254, interface(s) 256, mass storage device(s) 258, and I/O device(s) 260 to communicate with one another, as well as other devices or components coupled to bus 262. Bus 262 represents one or more of several types of bus structures, such as a system bus, PCI bus, IEEE 1394 bus, USB bus, and so forth.

For purposes of illustration, programs and other executable program components are shown herein as discrete blocks, although it is understood that such programs and components may reside at various times in different storage components of computing device 250 and are executed by processor(s) 252. Alternatively, the systems and procedures described herein can be implemented in hardware, or a combination of hardware, software, and/or firmware. For example, one or more application specific integrated circuits (ASICs) or field programmable gate arrays (FPGAs) can be programmed to carry out one or more of the systems and procedures described herein.

Figure 3A:
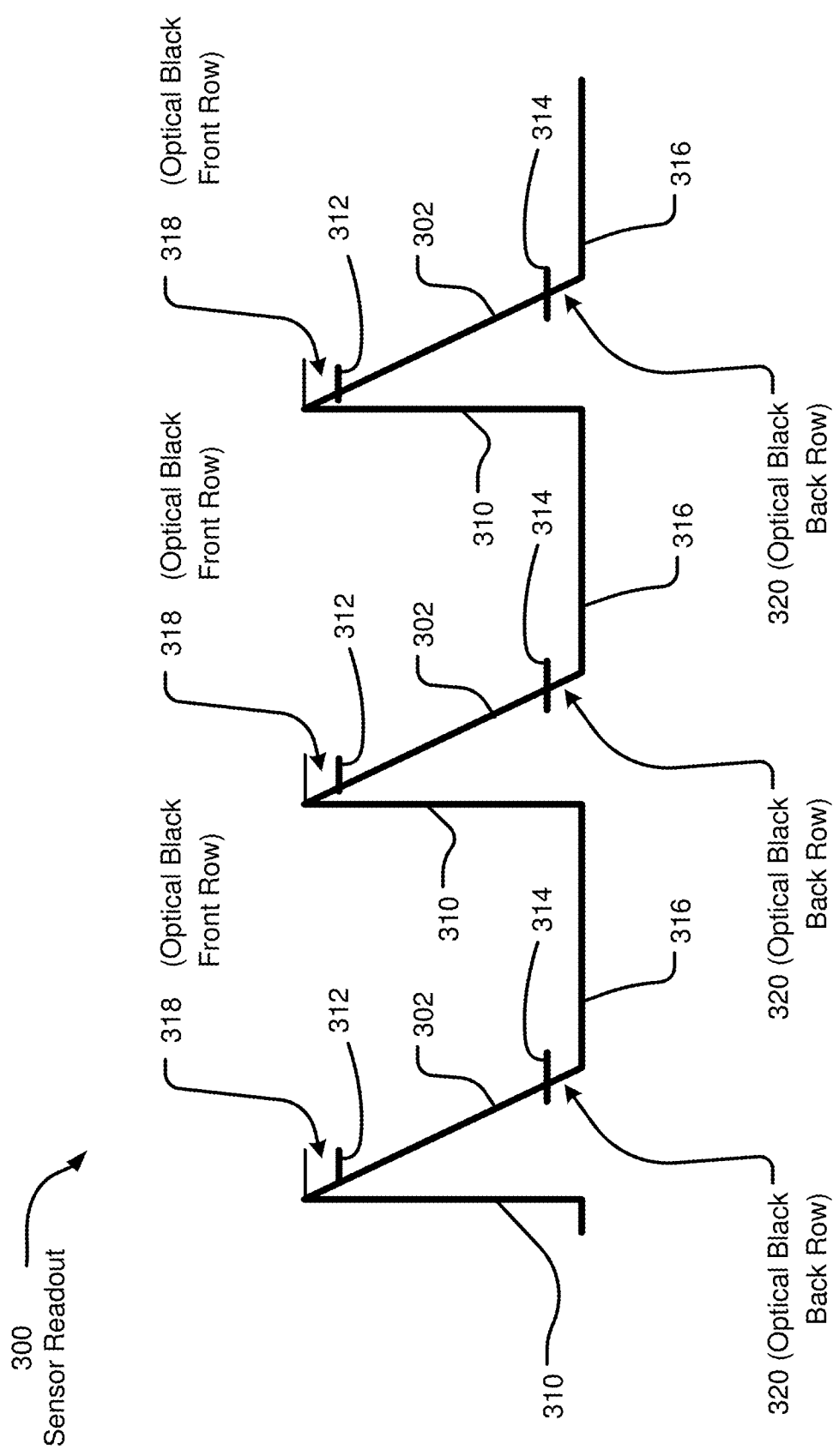

FIG. 3A illustrates the operational cycles of a sensor used in rolling readout mode or during the sensor readout 300. The frame readout may start at and may be represented by vertical line 310. The read-out period is represented by the diagonal or slanted line 302. The sensor may be read out on a row by row basis, the top of the downwards slanted edge being the sensor top row 312 and the bottom of the downwards slanted edge being the sensor bottom row 314. The time between the last row readout and the next readout cycle may be called the blanking period 316. It should be noted that some of the sensor pixel rows might be covered with a light shield (e.g., a metal coating or any other substantially black layer of another material type). These covered pixel rows may be referred to as optical black rows 318 and 320. Optical black rows 318 and 320 may be used as input for correction algorithms. As shown in FIG. 3A, these optical black rows 318 and 320 may be located on the top of the pixel array or at the bottom of the pixel array or at the top and the bottom of the pixel array.

FIG. 3B illustrates a process of controlling the amount of electromagnetic radiation, e.g., light, that is exposed to a pixel, thereby integrated or accumulated by the pixel. It will be appreciated that photons are elementary particles of electromagnetic radiation. Photons are integrated, absorbed, or accumulated by each pixel and converted into an electrical charge or current. An electronic shutter or rolling shutter (shown by dashed line 322) may be used to start the integration time by resetting the pixel. The light will then integrate until the next readout phase. The position of the electronic shutter 322 can be moved between two readout cycles 302 to control the pixel saturation for a given amount of light. It should be noted that this technique allows for a constant integration time between two different lines but introduces a delay when moving from top to bottom rows.

FIG. 3C illustrates the case where the electronic shutter 322 has been removed. In this configuration, the integration of the incoming light may start during readout 302 and may end at the next readout cycle 302, which also defines the start of the next integration.

Figure 3D:
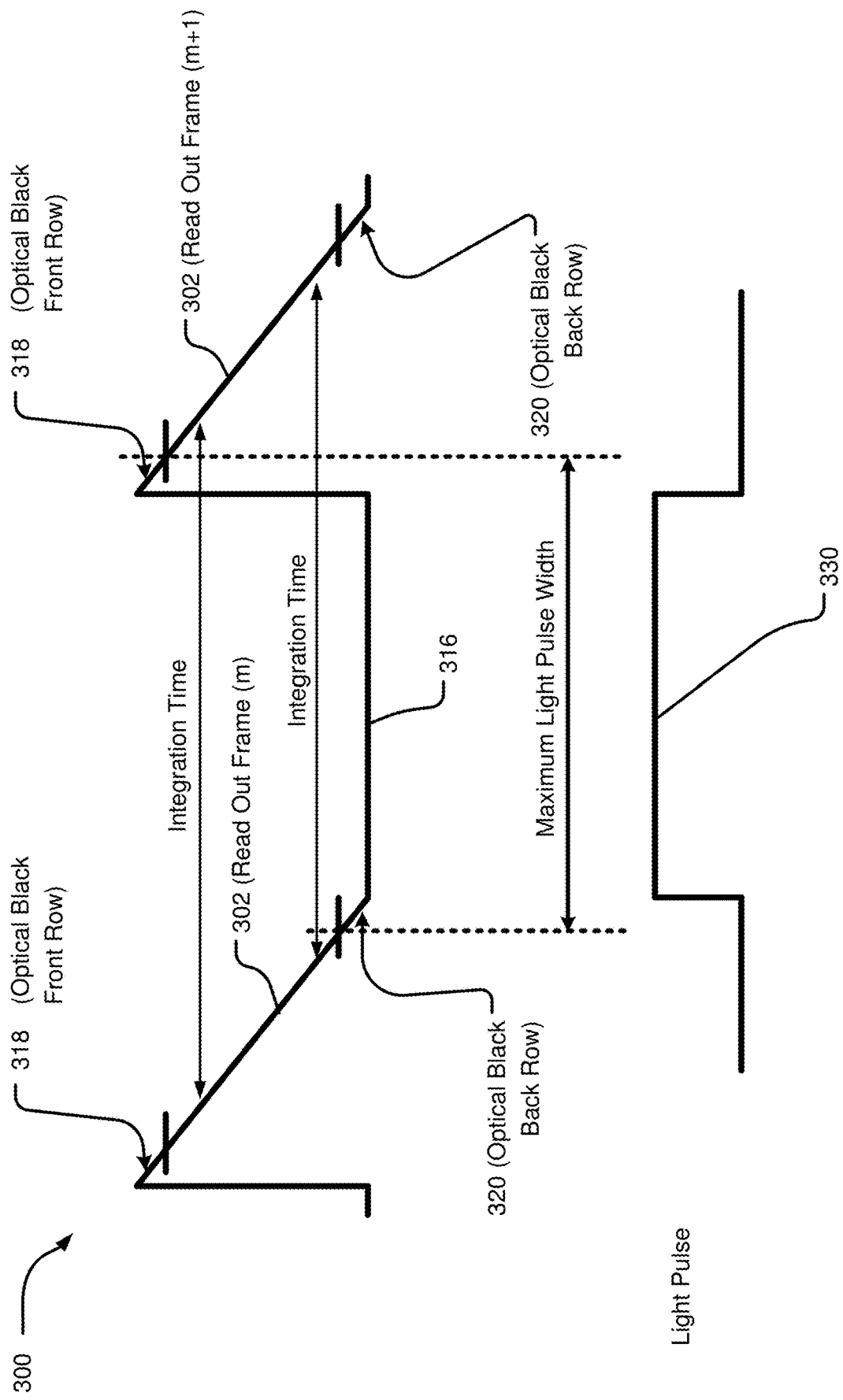

FIG. 3D shows a configuration without an electronic shutter 322, but with a controlled and pulsed light 210 during the blanking period 316. This ensures that all rows see the same light issued from the same light pulse 210. In other words, each row will start its integration in a dark environment, which may be at the optical black back row 320 of read out frame (m) for a maximum light pulse width, and will then receive a light strobe and will end its integration in a dark environment, which may be at the optical black front row 318 of the next succeeding read out frame (m+1) for a maximum light pulse width. In the FIG. 3D example, the image generated from the light pulse will be solely available during frame (m+1) readout without any interference with frames (m) and (m+2). It should be noted that the condition to have a light pulse to be read out only in one frame and not interfere with neighboring frames is to have the given light pulse firing during the blanking period 316. Because the optical black rows 318, 320 are insensitive to light, the optical black back rows 320 time of frame (m) and the optical black front rows 318 time of frame (m+1) can be added to the blanking period 316 to determine the maximum range of the firing time of the light pulse 210.

As illustrated in the FIG. 3A, a sensor may be cycled many times to receive data for each pulsed color or wavelength (e.g., Red, Green, Blue, or other wavelength on the electromagnetic spectrum). Each cycle may be timed. In an embodiment, the cycles may be timed to operate within an interval of 16.67 ms. In another embodiment, the cycles may be timed to operate within an interval of 8.3 ms. It will be appreciated that other timing intervals are contemplated by the disclosure and are intended to fall within the scope of this disclosure.

Figure 4A:
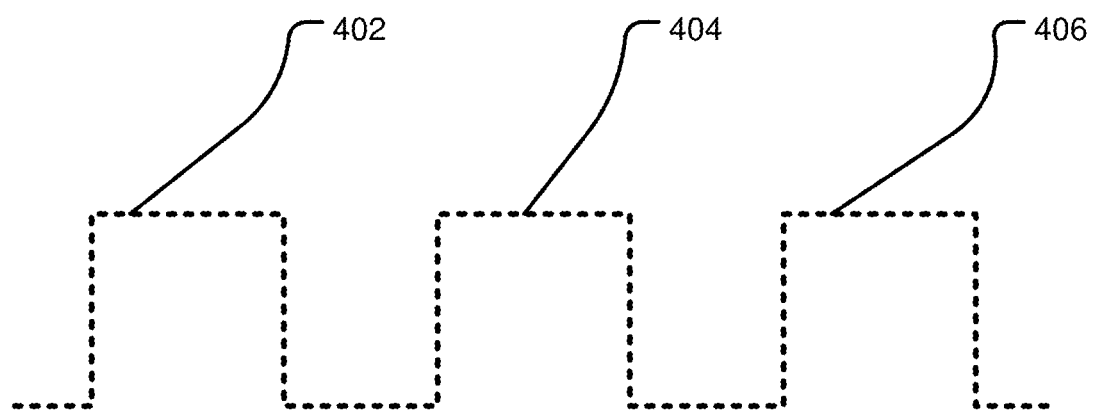
FIG. 4A is a graphical representation of the operation of an embodiment of an electromagnetic emitter.

FIG. 4A graphically illustrates the operation of an embodiment of an electromagnetic emitter. An emitter may be timed to correspond with the cycles of a sensor, such that electromagnetic radiation is emitted within the sensor operation cycle and/or during a portion of the sensor operation cycle. FIG. 4A illustrates Pulse 1 at 402, Pulse 2 at 404, and Pulse 3 at 406. In an embodiment, the emitter may pulse during the readout period 302 of the sensor operation cycle. In an embodiment, the emitter may pulse during the blanking portion 316 of the sensor operation cycle. In an embodiment, the emitter may pulse for a duration that is during portions of two or more sensor operational cycles. In an embodiment, the emitter may begin a pulse during the blanking portion 316, or during the optical black portion 320 of the readout period 302, and end the pulse during the readout period 302, or during the optical black portion 318 of the readout period 302 of the next succeeding cycle. It will be understood that any combination of the above is intended to fall within the scope of this disclosure as long as the pulse of the emitter and the cycle of the sensor correspond.

Figure 4B:
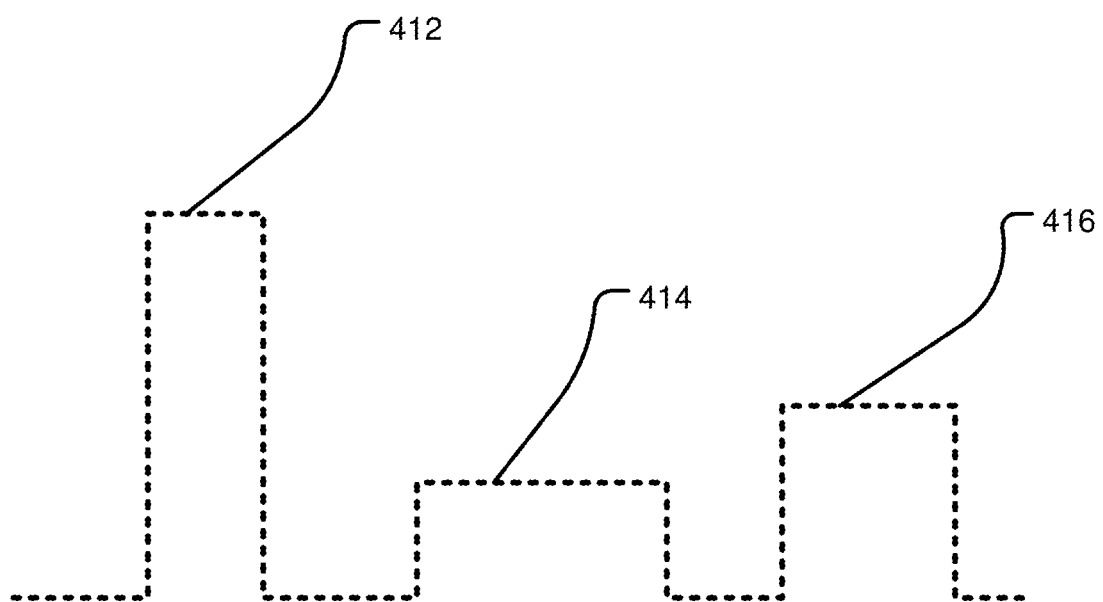
FIG. 4B is a graphical representation of varying the duration and magnitude of the emitted electromagnetic pulse to provide exposure control.

FIG. 4B graphically represents varying the duration and magnitude of the emitted electromagnetic pulse (e.g., Pulse 1 at 412, Pulse 2 at 414, and Pulse 3 at 416) to control exposure. An emitter having a fixed output magnitude may be pulsed during any of the cycles noted above in relation to FIGS. 3D and 4A for an interval to provide the needed electromagnetic energy to the pixel array. An emitter having a fixed output magnitude may be pulsed at a longer interval of time, thereby providing more electromagnetic energy to the pixels or the emitter may be pulsed at a shorter interval of time, thereby providing less electromagnetic energy. Whether a longer or shorter interval time is needed depends upon the operational conditions.

In contrast to adjusting the interval of time the emitter pulses a fixed output magnitude, the magnitude of the emission itself may be increased to provide more electromagnetic energy to the pixels. Similarly, decreasing the magnitude of the pulse provides less electromagnetic energy to the pixels. It should be noted that an embodiment of the system may have the ability to adjust both magnitude and duration concurrently, if desired. Additionally, the sensor may be adjusted to increase its sensitivity and duration as desired for optimal image quality. FIG. 4B illustrates varying the magnitude and duration of the pulses. In the illustration, Pulse 1 at 412 has a higher magnitude or intensity than either Pulse 2 at 414 or Pulse 3 at 416. Additionally, Pulse 1 at 412 has a shorter duration than Pulse 2 at 414 or Pulse 3 at 416, such that the electromagnetic energy provided by the pulse is illustrated by the area under the pulse shown in the illustration. In the illustration, Pulse 2 at 414 has a relatively low magnitude or intensity and a longer duration when compared to either Pulse 1 at 412 or Pulse 3 at 416. Finally, in the illustration, Pulse 3 at 416 has an intermediate magnitude or intensity and duration, when compared to Pulse 1 at 412 and Pulse 2 at 414.

Figure 5:
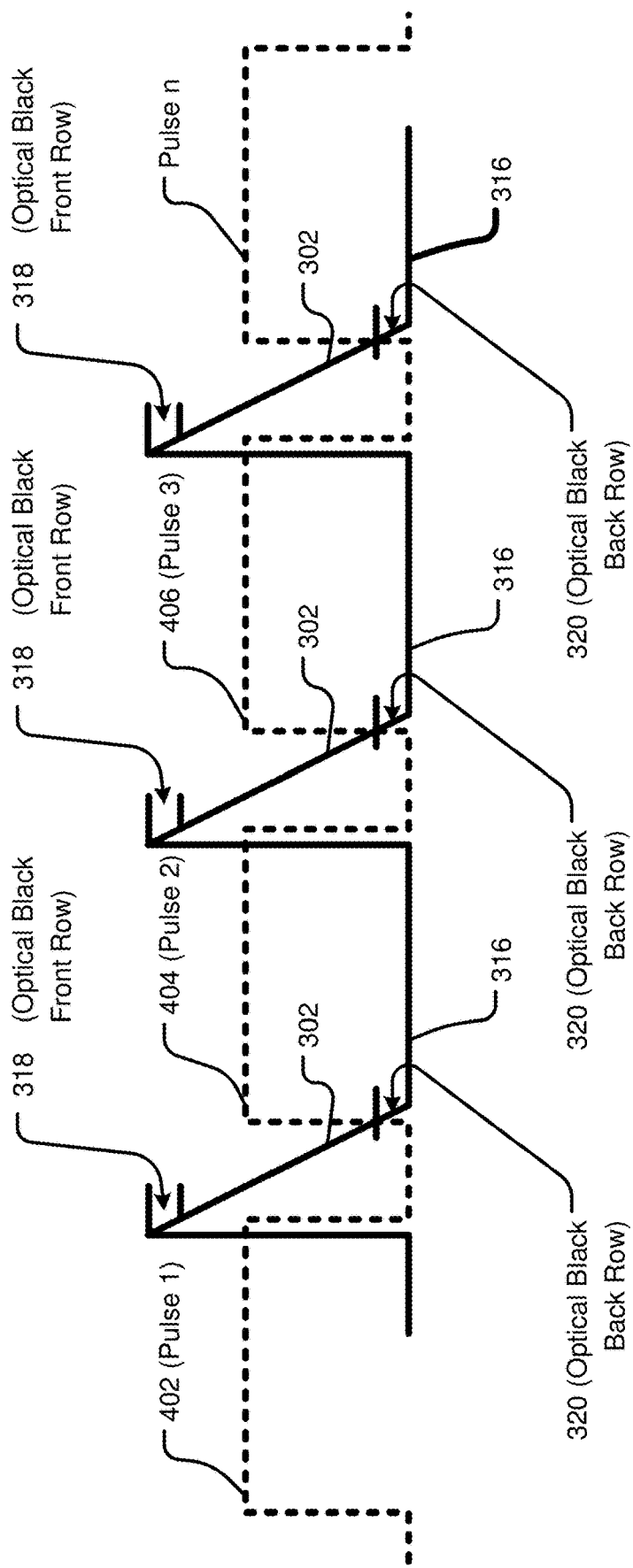
FIG. 5 is a graphical representation of an embodiment of the disclosure combining the operational cycles of a sensor, the electromagnetic emitter, and the emitted electromagnetic pulses of FIGS. 3A-4B, which demonstrate the imaging system during operation.

FIG. 5 is a graphical representation of an embodiment of the disclosure combining the operational cycles, the electromagnetic emitter, and the emitted electromagnetic pulses of FIGS. 3A-3D and 4A to demonstrate the imaging system during operation in accordance with the principles and teachings of the disclosure. As can be seen in the figure, the electromagnetic emitter pulses the emissions primarily during the blanking period 316 of the image sensor such that the pixels will be charged and ready to read during the readout period 302 of the image sensor cycle. The dashed lines in FIG. 5 represent the pulses of electromagnetic radiation (from FIG. 4A). The pulses of electromagnetic radiation are primarily emitted during the blanking period 316 of the image sensor but may overlap with the readout period 302 of the image sensor.

An exposure frame includes the data read by the pixel array of the image sensor during a readout period 302. The exposure frame may be combined with an indication of what type of pulse was emitted by the emitter prior to the readout period 302. The combination of the exposure frame and the indication of the pulse type may be referred to as a dataset. Multiple exposure frames may be combined to generate a black-and-white or RGB color image. Additionally, hyperspectral, fluorescence, and/or laser mapping imaging data may be overlaid on a black-and-white or RGB image.

In an embodiment, an RGB image frame is generated based on three exposure frames, including a red exposure frame generated by the image sensor subsequent to a red emission, a green exposure frame generated by the image sensor subsequent to a green emission, and a blue exposure frame generated by the image sensor subsequent to a blue emission. Hyperspectral imaging data may be overlaid on the RGB image frame. The hyperspectral imaging data may be drawn from one or more hyperspectral exposure frames. A hyperspectral exposure frame includes data generated by the image sensor during the readout period 302 subsequent to a hyperspectral emission of electromagnetic radiation. The hyperspectral emission includes any suitable emission in the electromagnetic spectrum and may include multiple emissions of light that span up to the entire electromagnetic spectrum. In an embodiment, the hyperspectral emission includes an emission of electromagnetic radiation having a wavelength from about 513 nm to about 545 nm; from about 565 nm to about 585 nm; and/or from about 900 nm to about 1000 nm. The hyperspectral exposure frame may include multiple hyperspectral exposure frames that are each generated by the image sensor subsequent to a different type of hyperspectral emission. In an embodiment, the hyperspectral exposure frame includes multiple hyperspectral exposure frames, including a first hyperspectral exposure frame generated by the image sensor subsequent to an emission of electromagnetic radiation with a wavelength from about 513 nm to about 545, a second hyperspectral exposure frame generated by the image sensor subsequent to an emission of electromagnetic radiation with a wavelength from about 565 nm to about 585 nm, and a third hyperspectral exposure frame generated by the image sensor subsequent to an emission of electromagnetic radiation with a wavelength from about 900 nm to about 1000. The hyperspectral exposure frame may include further additional hyperspectral exposure frames that are generated by the image sensor subsequent to other hyperspectral emissions of light as needed based on the imaging application.

A hyperspectral exposure frame may be generated by the image sensor subsequent to an emission of multiple different partitions of electromagnetic radiation. For example, a single hyperspectral exposure frame may be sensed by the pixel array after an emission of electromagnetic radiation with a wavelength from about 513 nm to about 545; from about 565 nm to about 585 nm; and from about 900 nm to about 1000 nm. The emission of electromagnetic radiation may include a single pulse with each of the multiple wavelengths being emitted simultaneously, multiple sub-pulses wherein each sub-pulse is a different wavelength of electromagnetic radiation, or some combination of the above. The emission of electromagnetic radiation with the one or more pulses may occur during a blanking period 316 that occurs prior to the readout period 302 in which the exposure frame is sensed by the pixel array.

In an embodiment, an exposure frame is the data sensed by the pixel array during the readout period 302 that occurs subsequent to a blanking period 316. The emission of electromagnetic radiation is emitted during the blanking period 316. In an embodiment, a portion of the emission of electromagnetic radiation overlaps the readout period 316. The blanking period 316 occurs when optical black pixels of the pixel array are being read and the readout period 302 occurs when active pixels of the pixel array are being read. The blanking period 316 may overlap the readout period 302.

FIGS. 6A and 6B illustrate processes for recording an image frame. Multiple image frames may be strung together to generate a video stream. A single image frame may include data from multiple exposure frames, wherein an exposure frame is the data sensed by a pixel array subsequent to an emission of electromagnetic radiation. FIG. 6A illustrates a traditional process that is typically implemented with a color image sensor having a color filter array (CFA) for filtering out certain wavelengths of light per pixel. FIG. 6B is a process that is disclosed herein and can be implemented with a monochromatic "color agnostic" image sensor that is receptive to all wavelengths of electromagnetic radiation.

The process illustrated in FIG. 6A occurs from time t(0) to time t(1). The process begins with a white light emission 602 and sensing white light 604. The image is processed and displayed at 606 based on the sensing at 604.

The process illustrated in FIG. 6B occurs from time t(0) to time t(1). The process begins with an emission of green light 612 and sensing reflected electromagnetic radiation 614 subsequent to the emission of green light 612. The process continues with an emission of red light 616 and sensing reflected electromagnetic radiation 618 subsequent to the emission of red light 616. The process continues with an emission of blue light 620 and sensing reflected electromagnetic radiation 622 subsequent to the emission of blue light 620. The process continues with one or more emissions of a hyperspectral 624 emission and sensing reflected electromagnetic energy 626 subsequent to each of the one or more emissions of the hyperspectral 624 emission.

The process illustrated in FIG. 6B provides a higher resolution image and provides a means for generating an RGB image that further includes hyperspectral imaging data. When partitioned spectrums of light are used, (as in FIG. 6B) a sensor can be made sensitive to all wavelengths of electromagnetic energy. In the process illustrated in FIG. 6B, the monochromatic pixel array is instructed that it is sensing electromagnetic energy from a predetermined partition of the full spectrum of electromagnetic energy in each cycle. Therefore, to form an image the sensor need only be cycled with a plurality of differing partitions from within the full spectrum of light. The final image is assembled based on the multiple cycles. Because the image from each color partition frame cycle has a higher resolution (compared with a CFA pixel array), the resultant image created when the partitioned light frames are combined also has a higher resolution. In other words, because each and every pixel within the array (instead of, at most, every second pixel in a sensor with a CFA) is sensing the magnitudes of energy for a given pulse and a given scene, just fractions of time apart, a higher resolution image is created for each scene.

As can be seen graphically in the embodiments illustrated in FIGS. 6A and 6B between times t(0) and t(1), the sensor for the partitioned spectrum system in FIG. 6B has cycled at least four times for every one of the full spectrum system in FIG. 6A. In an embodiment, a display device (LCD panel) operates at 50-60 frames per second. In such an embodiment, the partitioned light system in FIG. 6B may operate at 200-240 frames per second to maintain the continuity and smoothness of the displayed video. In other embodiments, there may be different capture and display frame rates. Furthermore, the average capture rate could be any multiple of the display rate.

In an embodiment, it may be desired that not all partitions be represented equally within the system frame rate. In other words, not all light sources have to be pulsed with the same regularity so as to emphasize and de-emphasize aspects of the recorded scene as desired by the users. It should also be understood that non-visible and visible partitions of the electromagnetic spectrum may be pulsed together within a system with their respective data value being stitched into the video output as desired for display to a user.

An embodiment may comprise a pulse cycle pattern as follows:
  i. Green pulse;
  ii. Red pulse;
  iii. Blue pulse;
  iv. Green pulse;
  v. Red pulse;
  vi. Blue pulse;
  vii. Hyperspectral pulse;
  viii. (Repeat)

An embodiment may comprise a pulse cycle pattern as follows:
  i. Luminance pulse;
  ii. Red chrominance pulse;
  iii. Luminance pulse;
  iv. Blue Chrominance pulse;
  v. Hyperspectral pulse;
  vi. (Repeat)

An embodiment may comprise a pulse cycle pattern as follows:
  i. Luminance pulse;
  ii. Red chrominance pulse;
  iii. Luminance pulse;
  iv. Blue Chrominance pulse;
  v. Luminance pulse;
  vi. Red chrominance pulse;
  vii. Luminance pulse;
  viii. Blue Chrominance pulse;
  ix. Hyperspectral pulse;
  x. (Repeat)

As can be seen in the example, a hyperspectral partition may be pulsed at a rate differing from the rates of the other partition pulses. This may be done to emphasize a certain aspect of the scene, with the hyperspectral data simply being overlaid with the other data in the video output to make the desired emphasis. It should be noted that the addition of a hyperspectral partition on top of the RED, GREEN, and BLUE partitions does not necessarily require the serialized system to operate at four times the rate of a full spectrum non-serial system because every partition does not have to be represented equally in the pulse pattern. As seen in the embodiment, the addition of a hyperspectral partition pulse that is represented less in a pulse pattern results in an increase of less than 20% of the cycling speed of the sensor to accommodate the irregular partition sampling.

In various embodiments, the pulse cycle pattern may further include any of the following wavelengths in any suitable order. Such wavelengths may be particularly suited for exciting a fluorescent reagent to generate fluorescence imaging data by sensing the relaxation emission of the fluorescent reagent based on a fluorescent reagent relaxation emission:
  i. 770±20 nm;
  ii. 770±10 nm;
  iii. 770±5 nm;
  iv. 790±20 nm;
  v. 790±10 nm;
  vi. 790±5 nm;
  vii. 795±20 nm;
  viii. 795±10 nm;
  ix. 795±5 nm;
  x. 815±20 nm;
  xi. 815±10 nm;
  xii. 815±5 nm;
  xiii. 770 nm to 790 nm; and/or
  xiv. 795 nm to 815 nm.

In various embodiments, the pulse cycle may further include any of the following wavelengths in any suitable order. Such wavelengths may be particularly suited for generating hyperspectral imaging data:
  i. 513 nm to 545 nm;
  ii. 565 nm to 585 nm;
  iii. 1500 nm to 2100 nm;
  iv. 513±5 nm;
  v. 513±10 nm;
  vi. 513±20 nm;
  vii. 513±30 nm;
  viii. 513±35 nm;
  ix. 545±5 nm;
  x. 545±10 nm;
  xi. 545±20 nm;
  xii. 545±30 nm;
  xiii. 545±35 nm;
  xiv. 565±5 nm;
  xv. 565±10 nm;
  xvi. 565±20 nm;
  xvii. 565±30 nm;
  xviii. 565±35 nm;
  xix. 585±5 nm;
  xx. 585±10 nm;
  xxi. 585±20 nm;
  xxii. 585±30 nm;
  xxiii. 585±35 nm;
  xxiv. 900±5 nm;
  xxv. 900±10 nm;
  xxvi. 900±20 nm;
  xxvii. 900±30 nm;
  xxviii. 900±35 nm;
  xxix. 1000±5 nm;
  xxx. 1000±10 nm;
  xxxi. 1000±20 nm;
  xxxii. 1000±30 nm; or
  xxxiii. 1000±35 nm.

The partition cycles may be divided so as to accommodate or approximate various imaging and video standards. In an embodiment, the partition cycles comprise pulses of electromagnetic energy in the Red, Green, and Blue spectrum as follows as illustrated best in FIGS. 7A-7D. The timing relationship between the emission of pulses of electromagnetic radiation by the emitter, and the readout of the pixel array is further illustrated in FIGS. 7A-7D.

Figure 7A:
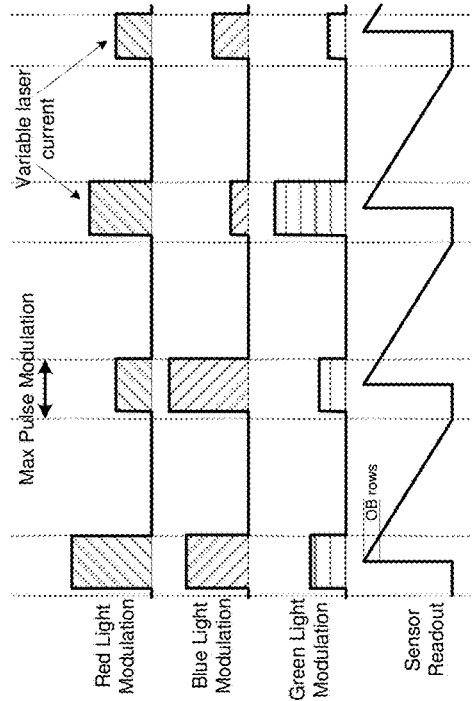
FIGS. 7A-7E illustrate schematic views of the processes over an interval of time for recording a frame of video for both full spectrum light and partitioned spectrum light.

In FIG. 7A, the different light intensities have been achieved by modulating the light pulse width or duration within the working range shown by the vertical grey dashed lines. FIG. 7A illustrates the general timing relationships within a four-frame cycle, between pulsed mixtures of three wavelengths and the readout cycle of the pixel array of the image sensor. In an embodiment, there are three monochromatic pulsed light sources under the control of the controller. Periodic sequences of monochromatic red, monochromatic green, and monochromatic blue exposure frames are captured, e.g. with an R-G-B-G pulsing pattern and assembled into an sRGB image frame by the image signal processor chain.

Figure 7C:
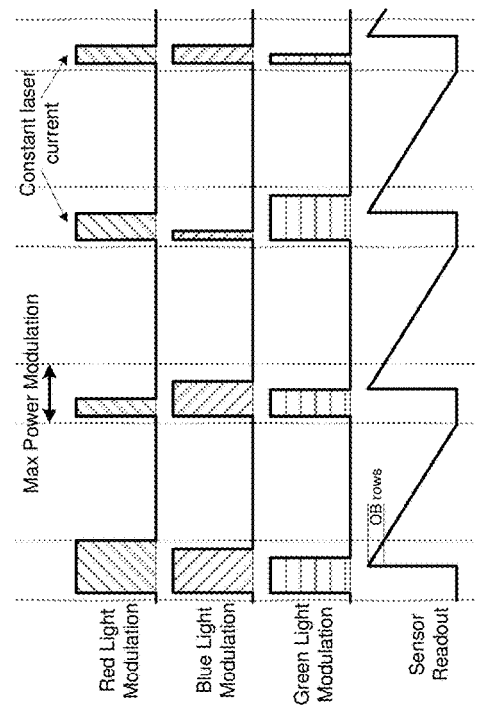
Figure 7B:
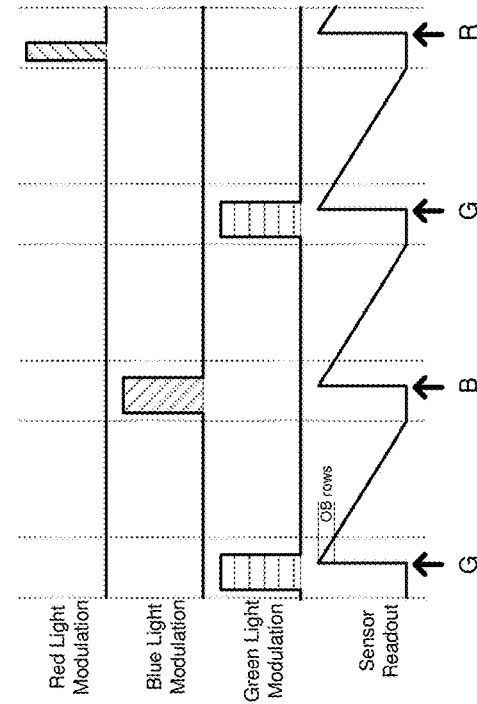

In FIG. 7B, the different light intensities have been achieved by modulating the light power or the power of the electromagnetic emitter, which may be a laser or LED emitter, but keeping the pulse width or duration constant.

FIG. 7C shows the case where both the light power and the light pulse width are being modulated, leading to greater flexibility. The partition cycles may use Cyan Magenta Yellow (CMY), infrared, ultraviolet, hyperspectral, and fluorescence using a non-visible pulse source mixed with visible pulse sources and any other color space required to produce an image or approximate a desired video standard that is currently known or yet to be developed. It should also be understood that a system may be able to switch between the color spaces on the fly to provide the desired image output quality.

Figure 7D:
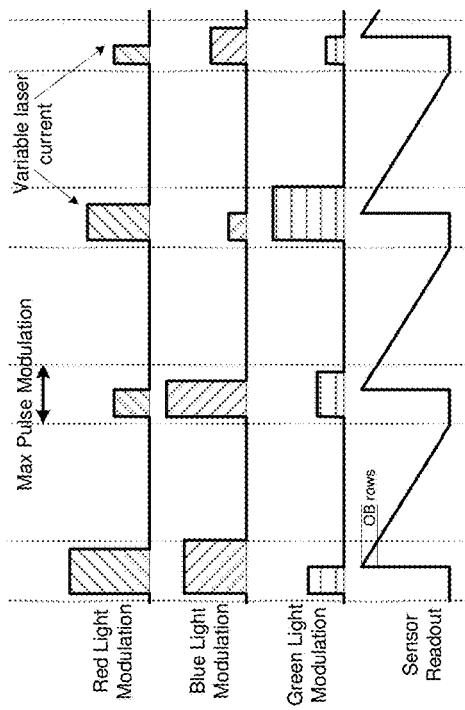

In an embodiment using color spaces Green-Blue-Green-Red (as seen in FIG. 7D) it may be desirous to pulse the luminance components more often than the chrominance components because users are generally more sensitive to light magnitude differences than to light color differences. This principle can be exploited using a monochromatic image sensor as illustrated in FIG. 7D. In FIG. 7D, green, which contains the most luminance information, may be pulsed more often or with more intensity in a (G-B-G-R-G-B-G-R . . . ) scheme to obtain the luminance data. Such a configuration would create a video stream that has perceptively more detail, without creating and transmitting unperceivable data.

In an embodiment, all three sources of light are pulsed in unison with light energies that are modulated to provide pure luminance information in the same exposure frame. The light energies may be modulated according to color transformation coefficients that convert from RGB color space to YCbCr color space. It should be appreciated that the color transformation may be implemented according to any suitable standard such as the ITU-R BT.709 HD standard, the ITU-R BT.601 standard, the ITU-R BT.2020 standard, or any other suitable standard or formula. The conversion may be performed according to the ITU-R BT.709 HD standard as follows:

$$\begin{bmatrix} Y \\ Cb \\ Cr \end{bmatrix} = \begin{bmatrix} R \\ G \\ B \end{bmatrix} \begin{bmatrix} 0.183 & 0.614 & 0.062 \\ -0.101 & -0.339 & 0.439 \\ 0.439 & -0.399 & -0.040 \end{bmatrix}$$

In addition to the modulation of luminance information, a full color image further requires the red chrominance and blue chrominance components. However, the algorithm applied for the luminance component cannot be directly applied for chrominance componence because the algorithm is signed as reflected in the fact that some of the RGB coefficients are negative. In an embodiment, a degree of luminance is added so that all of the final pulse energies are a positive value. As long as the color fusion process in the image signal processor is aware of the composition of the chrominance exposure frames, they can be decoded by subtracting the appropriate amount of luminance from a neighboring frame. The pulse energy proportions are given by:

$$Y = 0.183 \cdot R + 0.614 \cdot G + 0.062 \cdot B$$

$$Cb = \lambda \cdot Y - 0.101 \cdot R - 0.339 \cdot G + 0.439 \cdot B$$

$$Cr = \delta \cdot Y + 0.439 \cdot R - 0.399 \cdot G - 0.040 \cdot B$$

where $$\lambda \geq \frac{0.339}{0.614} = 0.552$$

$$\delta \geq \frac{0.399}{0.614} = 0.650$$

If the λ factor is equal to 0.552, the red and green components are cancelled. In the case, the blue chrominance information can be provided with pure blue light. Similarly, if the δ factor is equal to 0.650, the blue and green components are cancelled, and the red chrominance information can be provided with pure red light. This embodiment is a convenient approximation for digital frame reconstruction.

In an embodiment where white balance is performed in the illumination domain, then the modulation is imposed in addition to the white balance modulation.

Figure 7E:
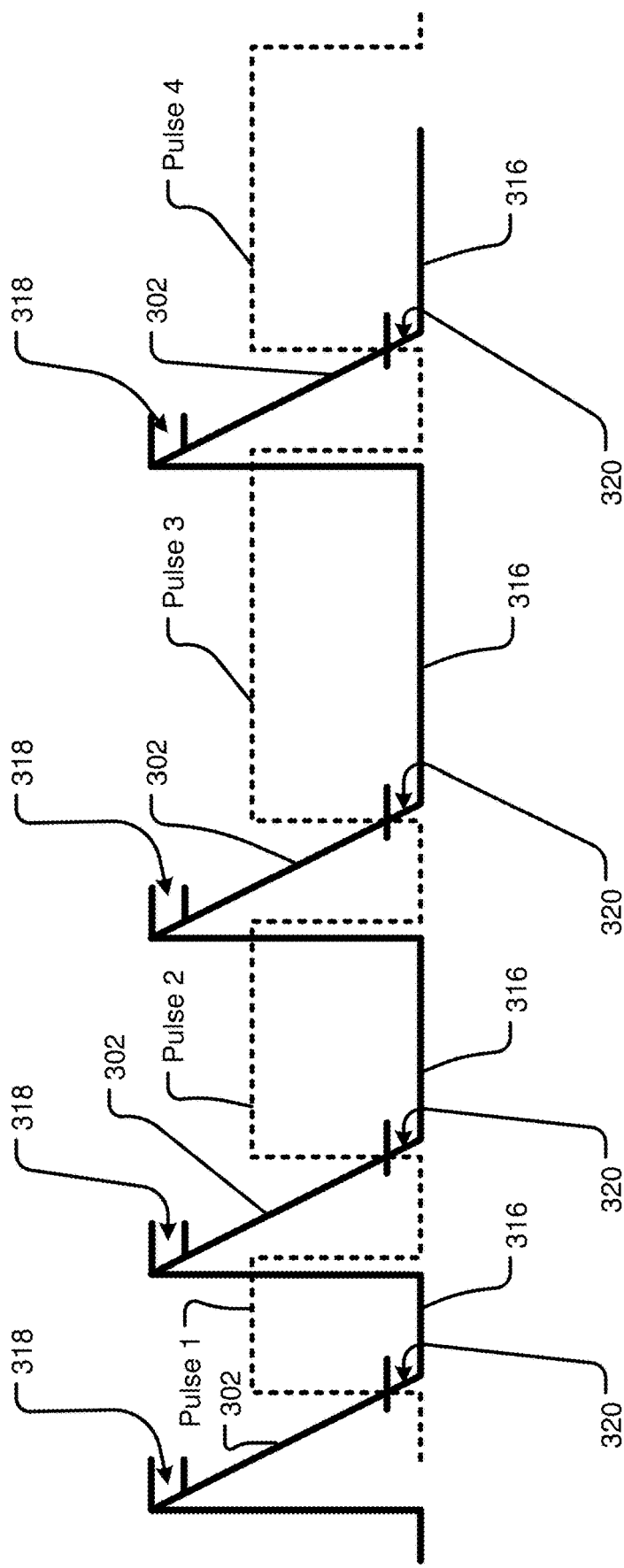

In an embodiment, duplicating the pulse of a weaker partition may be used to produce an output that has been adjusted for the weaker pulse. For example, blue laser light is considered weak relative to the sensitivity of silicon-based pixels and is difficult to produce in comparison to the red or green light, and therefore may be pulsed more often during a frame cycle to compensate for the weakness of the light. These additional pulses may be done serially over time or by using multiple lasers that simultaneously pulse to produce the desired compensation effect. It should be noted that by pulsing during a blanking period (time during which the sensor is not reading out the pixel array), the sensor is insensitive to differences/mismatches between lasers of the same kind and simply accumulates the light for the desired output. In another embodiment, the maximum light pulse range may be different from frame to frame. This is shown in FIG. 7E, where the light pulses are different from frame to frame. The sensor may be built to be able to program different blanking periods with a repeating pattern of two or three or four or n frames.

In FIG. 7E, four different light pulses are illustrated, and Pulse 1 may repeat for example after Pulse 4 and may have a pattern of four frames with different blanking periods. This technique can be used to place the most powerful partition on the smallest blanking period and therefore allow the weakest partition to have wider pulse on one of the next frames without the need of increasing the readout speed. The reconstructed frame can still have a regular pattern from frame to frame as it is constituted of many pulsed frames.

Figure 8:
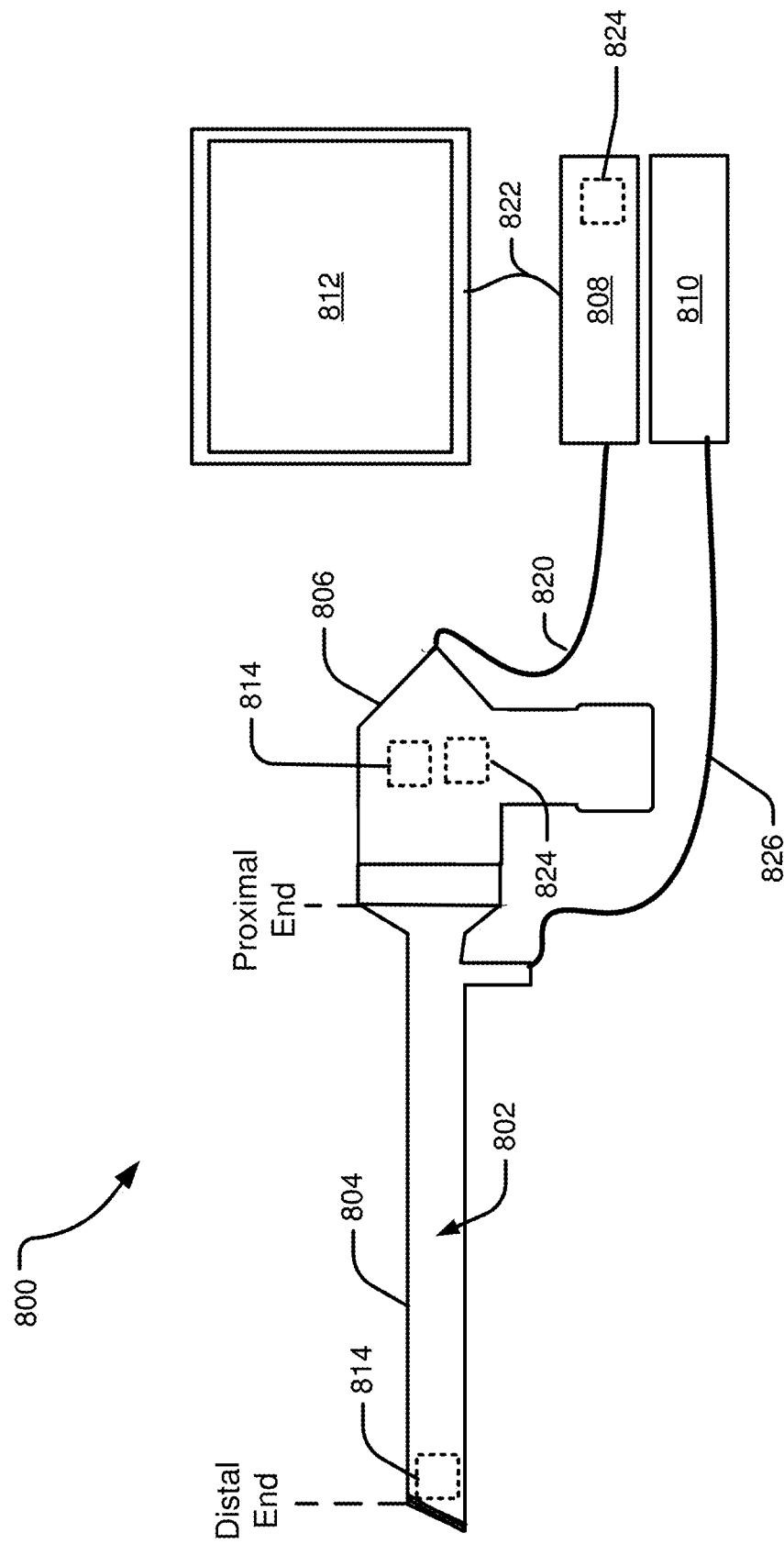
FIG. 8 illustrates an embodiment of a digital imaging system including an endoscopic device.

FIG. 8 illustrates a digital imaging system 800 that utilizes minimal pad interconnects to reduce the size of the image sensor for use with an endoscopic device within a light deficient environment. The digital imaging system 800 illustrated in FIG. 8 includes an endoscopic device 802 for use in a light deficient environment. The endoscopic device 802 includes an endoscope 804, an endoscope housing 806, a controller 808, an electronic communication 820, a light source 810, a light cable 826, a display 812, and an imaging device 814. The electronic communication 820 may include an electronic cable or other form of wired or wireless communication. The light cable 826 may be a fiber optic cable in some embodiments. The imaging device 814 may be an image sensor such as a CMOS image sensor with a pixel array.

In the example illustrated in FIG. 8, to facilitate discussion, the endoscopic device 804, endoscope housing 806, controller 808, light source 810, display 812, and imaging device 814 are shown individually with respect to one another. However, it should be appreciated and understood that this is not to be interpreted as limiting, and any one or more of these components can be integrated and/or connected in any suitable manner. It will be appreciated that the image sensor senses reflected electromagnetic radiation with the pixel array. The pixel array generates an exposure frame comprising image data in response to a pulse of electromagnetic radiation. A processor 824 may detect image textures and edges within the image frame and may further enhance textures and edges within the image frame. The processor 824, whether in the housing 806 or at the controller 808, may also retrieve from memory properties pertaining to the pixel technology and the applied sensor gain to assess an expectation for the magnitude of noise within an image frame created by the image sensor and using the noise expectation to control the edge enhancement application. A stream of image frames may be created by sequentially combining a plurality of image frames, wherein each image frame comprises data from multiple exposure frames.

It will be appreciated that traditional rod-lens endoscopes, used for laparoscopy, arthroscopy, urology, gynecology and ENT (ear-nose-throat) procedures, are expensive to manufacture owing to their complex optical composition. The incident image information is transported in the optical domain all the way along the length of the endoscope. Typically, these conventional endoscopes are optically coupled to a handpiece unit that includes the image sensor. This type of conventional endoscope is delicate and prone to damage during handling, use, and sterilization. The necessary repair and sterilization processes add further expense to each procedure for which they are utilized.

The endoscope 802 may be improved by placing the image sensing device at the distal end of the endoscope. In such an embodiment, the optical transport assembly may be replaced by a simple plastic lens stack. Such an endoscope may be so inexpensive that it may make more financial sense to manufacture them for single use only, to be subsequently disposed of or recycled, because this negates the repair and sterilization processes.

However, when the image sensor is located at the distal end of the endoscope 802, the image sensor must be very small. The distal end of the endoscope 802 is space constrained in the x and y dimensions. One method of decreasing the size of the image sensor is to reduce the number of bond pads within the image sensor chip. Each bond pad occupies significant physical space on an image sensor chip. Each bond pad is used to provide power or input/output signals to and from the image sensor chip. Therefore, in striving for minimal area, it is desirable to reduce the number of bond pads. This disclosure describes systems and methods for reducing pad count by combining digital input and output functionality into the same bidirectional pads. During image transmission, these bidirectional pads act as differential outputs. In an embodiment, during a defined portion of each exposure frame, the bidirectional pads switch direction to receive commands. In such an embodiment, the camera control electronics are synchronized such that the commands are issued to the image sensor bidirectional pads at a certain time when the bidirectional pads are configured to receive commands.

Further to this, in the context of an endoscope system, the simplicity and manufacturability can be enhanced by customizing the image sensor to receive commands and information from the endoscope handpiece. The information may be incorporated into the output data issued by the image sensor. This reduces the overall conductor count from endoscope to camera system. Such information sources may include user instigated button events or measurements of the angle of rotation of the endoscope with respect to the handpiece. Angular measurements are necessitated by certain embodiments of endoscopes having their image sensors placed at the distal end.

CMOS image sensors typically incorporate two different power supplies, necessitating three pads: VDD1, VDD2 & GND. The higher of the two voltages is used predominantly for the purpose of biasing the pixel array. Occasionally, the higher of the two voltages is also used to power the input and output circuits. The lower of the two voltages is typically used to power the peripheral analog circuitry and the digital portion of the image sensor, where applicable.

In an embodiment, the pad count is reduced by using only a single external power supply. This may be accomplished by using, for example, internal DC (direct current) to DC converters or regulators to provide for multiple internal supplies. Further, the pad count may be reduced by supplying only a single power level. The second power level may then be derived on-chip. This embodiment may be effective in removing a power circuit, such as a regulator, from the camera system.

Figure 9:
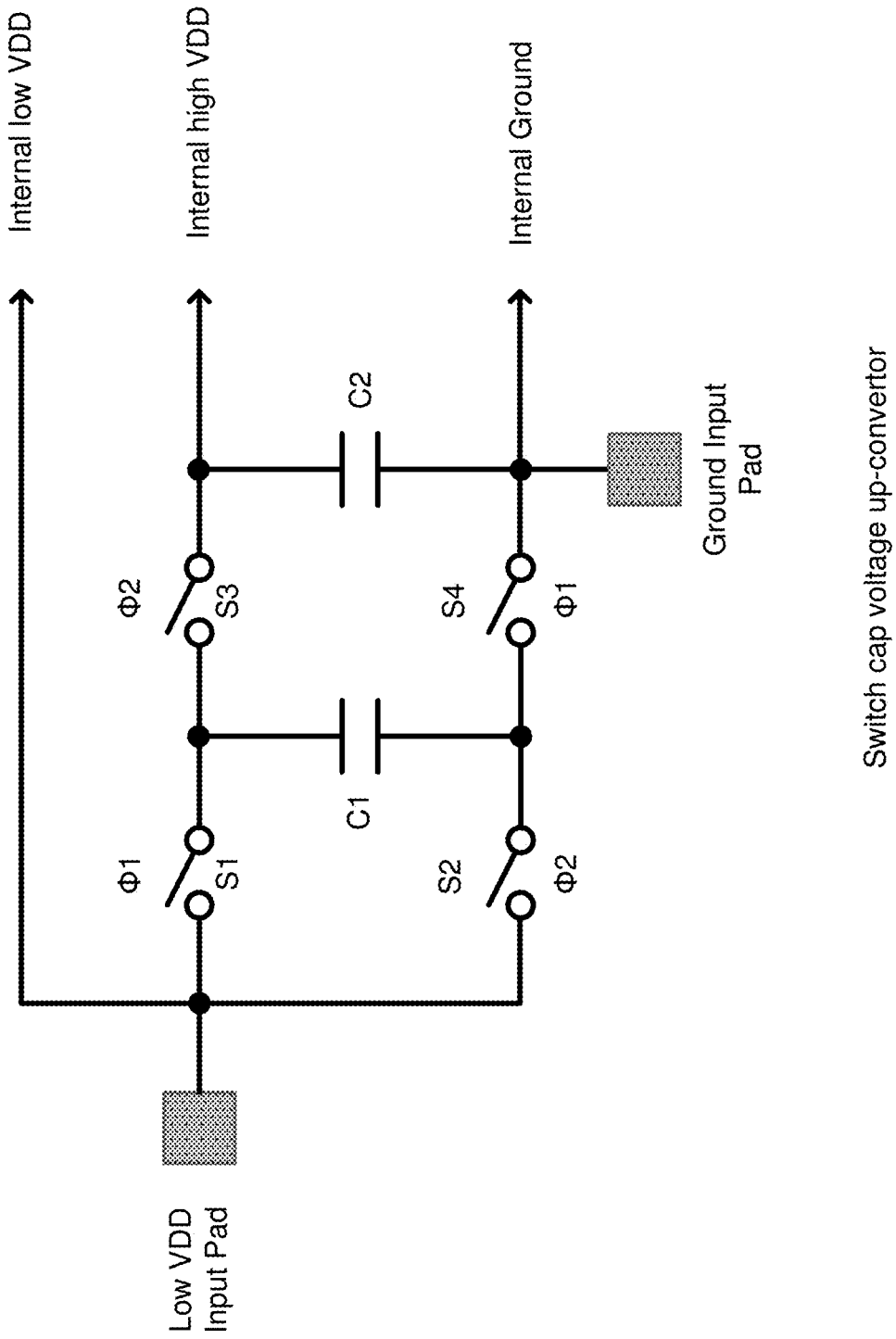
FIG. 9 is a circuit diagram illustrating an embodiment of a circuit for performing an internal up-conversion from a supplied low voltage to a higher voltage.

FIG. 9 illustrates a circuit diagram for an embodiment of a circuit for performing an internal up-conversion. The internal up-conversion converts a supplied low voltage to a higher voltage. The circuit includes a switch-cap DC-DC up-convertor. The flying cap C1 and the decoupling cap C2 are internal. The low power voltage (low VDD) supplies the up convertor and the relevant internal circuitry. It will be appreciated that an oscillator (not illustrated in FIG. 9) delivers the correct switching pattern to S1, S2, S3, and S4. This oscillator may be powered from the low voltage. When the oscillator is powered from the low voltage, proper level shifting needs to happen to achieve the correct switching voltage levels. The generated power supply may be tuned by carefully choosing the oscillator frequency, the internal resistance of the switch and the ratio between the flying cap C1 and the decoupling cap C2.

Figure 10A:
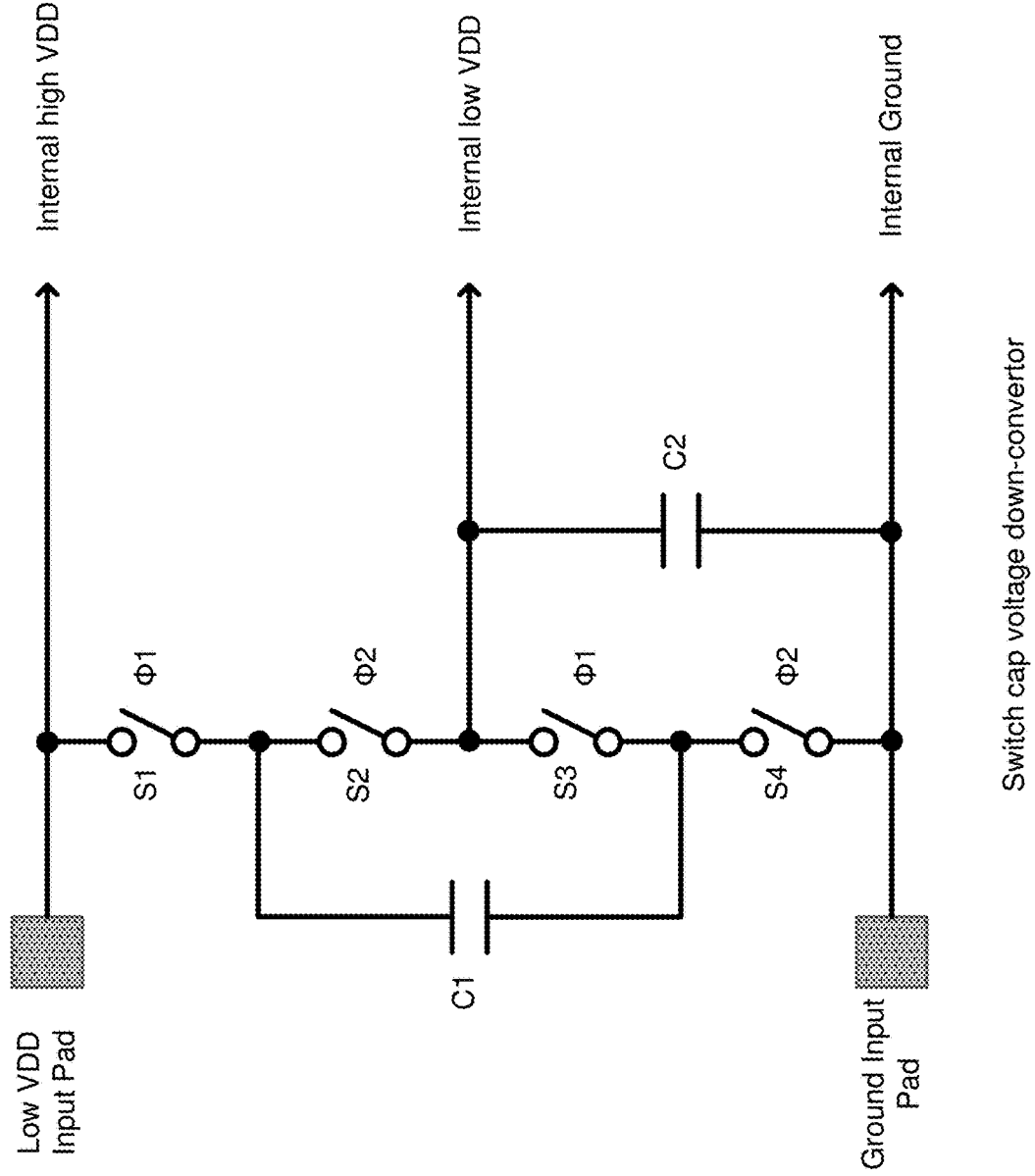
FIG. 10A is a circuit diagram illustrating an embodiment of a circuit for performing down-regulation when the supplied voltage is received from a high voltage supply (high VDD) and the circuit is based on a switch-cap DC-DC down converter.
Figure 10B:
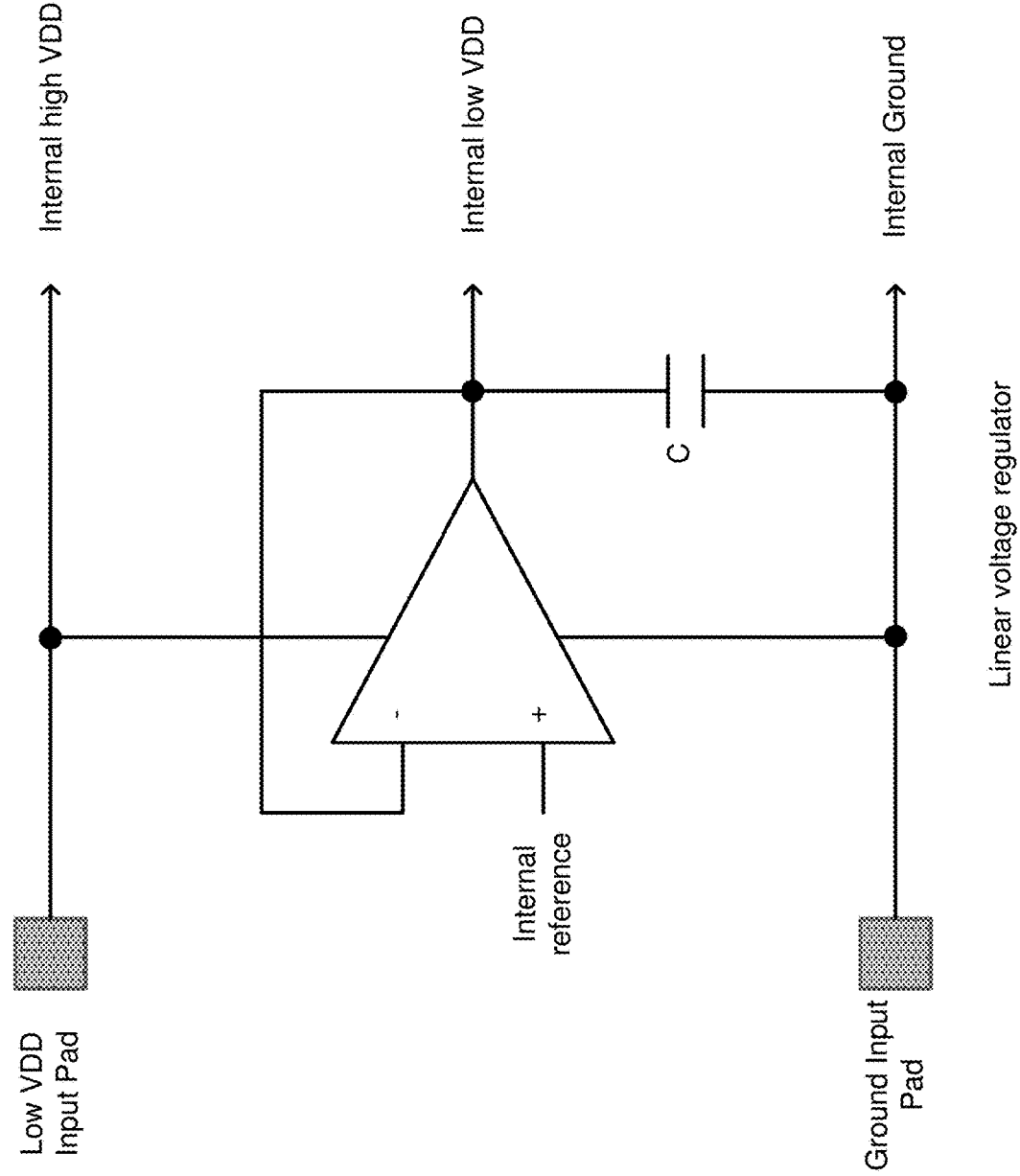
FIG. 10B is a circuit diagram illustrating an embodiment of a circuit for performing down-regulation when the supplied voltage is received from a high voltage supply (high VDD) and the circuit includes a Low Drop Out (LDO) regulator based on a linear circuit.

FIGS. 10A and 10B illustrate circuit diagrams for embodiments of circuits for performing down-regulation when the supplied voltage is received from a high voltage supply (high VDD). FIG. 10A illustrates a circuit diagram for a circuit that is based on a switch-cap DC-DC down converter. FIG. 10B illustrates a circuit diagram for a circuit that comprises a Low Drop Out (LDO) regulator based upon a linear circuit.

In FIG. 10B, the internal reference may come from a simple resistive divider or from a band gap reference generator. The LDO is less susceptible to pick up noise because there are no switching elements. However, the LDO is often less efficient that a switch-cap.

It should be noted that in general, up-conversion (as illustrated in FIG. 9) may be used more readily than down-regulators (as illustrated in FIGS. 10A and 10B). This is because the sensor high voltage is usually less critical in terms of noise and requires less current consumption. Therefore, the specifications for an up-converter are less demanding.

Figure 11:
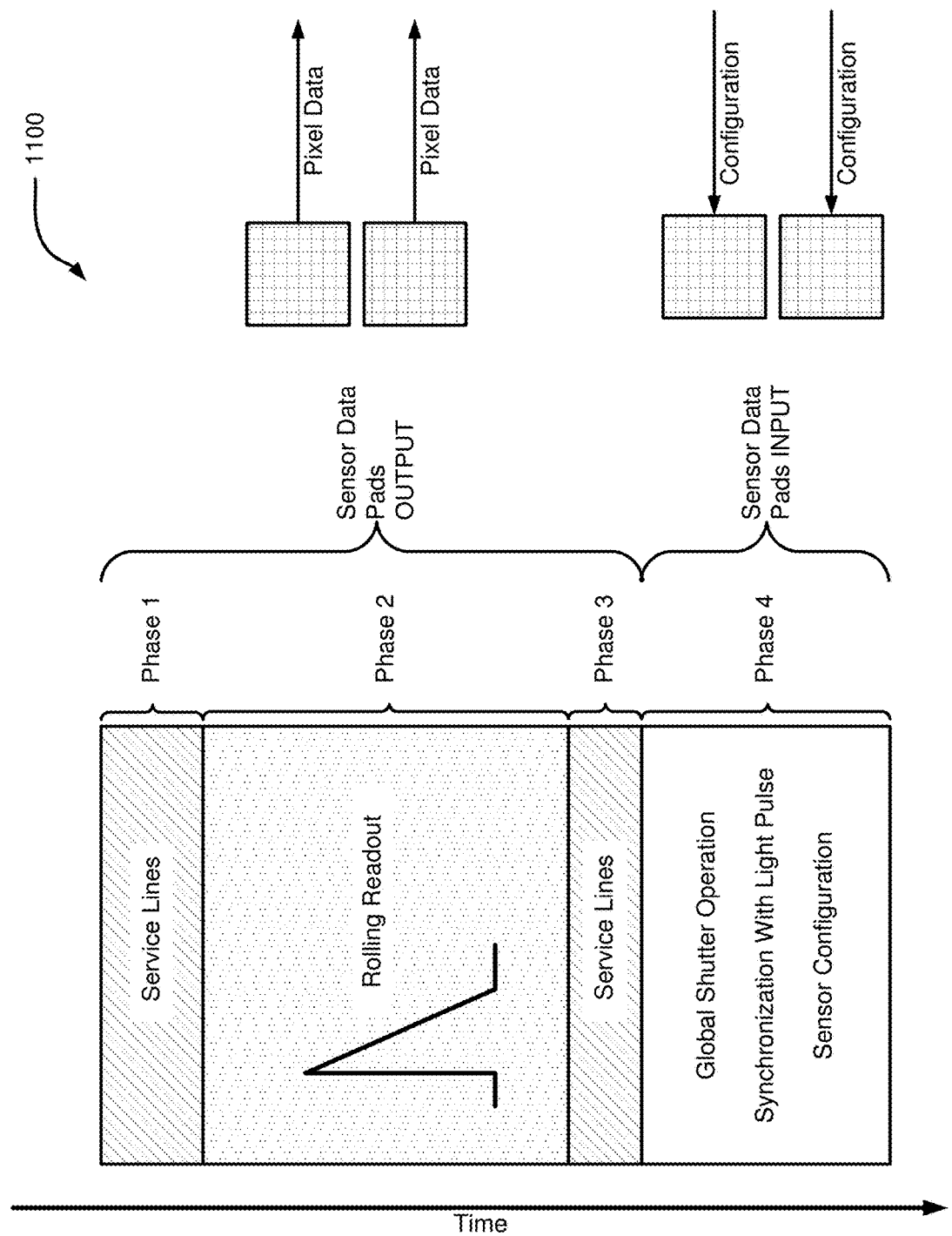
FIG. 11 is a schematic diagram of an embodiment of a regular operation sequence for an image sensor wherein bidirectional pads of the image sensor are configured to issue and receive information during different phases.

FIG. 11 is a schematic diagram of an embodiment of a regular operation sequence 1100 for an image sensor as discussed herein. The image sensor may include bidirectional pads configurable for issuing and receiving information. In an embodiment, one iteration of the regular operation sequence 1100 results in one exposure frame generated by the image sensor. In an alternative embodiment, one iteration of the regular operation sequence 1100 results in multiple exposure frames generated by the image sensor. The regular operation sequence 1100 may be implemented for the purpose of endoscopic imaging in the presence of controlled, pulsed illumination. Each frame period may comprise four distinct phases, which may be optimized for monochrome light pulsing and multiple pixel illuminations.

An embodiment of the regular operation sequence 1100 is implemented by an image sensor comprising bidirectional pads. The bidirectional pads are deployed for input and output operations. The bidirectional pads automatically switch between the output and input states at defined times. When the bidirectional pads are acting as outputs, image data and other types of data are issued from the image sensor. When the bidirectional pads are in the input state, they may receive slow control commands. To facilitate this, the period for capturing an exposure frame is divided into three defined phases. The defined phases include the rolling-readout phase wherein the bidirectional pads are in the output state and issue image data. The defined phases include the service-lines phase wherein the bidirectional pads are in the output state and issue other types of non-image data. The defined phases include the configuration phase wherein the bidirectional pads are converted to the input state and receive information. The camera system needs to know whether the bidirectional pads are in the input state or the output state at all times. During the rolling-readout phase and the service-line phase, the camera system may not issue slow-control commands.

The example regular operation sequence 1100 illustrated in FIG. 11 includes four phases, including phase 1, phase 2, phase 3, and phase 4. During phases 1 and 3, data is issued from the image sensor through sensor data pads. These "service line" periods may be used for internal and external monitoring and for encoding certain types of non-pixel data within the line. This data can be used to synchronize the image sensor chip with the camera system and can further be used for data locking. In an embodiment, imaging data from the pixel array is not output during the service line periods.

During phase 2, the sensor rolling readout is issued from the image sensor through the sensor data pads. Phase 2 includes the synchronization and readout of physical pixels in the pixel array of the image sensor during a "rolling readout" period. The rolling readout includes imaging data sensed by the pixel array and results in one or more exposure frames being generated by the image sensor.

During phase 4, image sensor configurations are received by the image sensor through the sensor data pads. Phase 4 may be referred to as the configuration phase. During phase 4, the data lines are reversed to accept incoming configuration commands rather than issue exiting pixel data or non-pixel data. During phase 4, the sensor pads may receive information about user inputs such as the desired angular position of the endoscope. The angle information may be relayed using various methods and structures to the image signal processing (ISP) chain within the camera system.

In an embodiment, low speed analog and digital signals are rerouted to the image sensor rather than being sent directly to the camera system. This reduces the endoscope conductor count. The signals may be digitally converted within the image sensor before being encoded alongside the image data in lieu of pixel data within special service lines. This strategy eliminates the need for extra wires in the endoscope cable and extra active components within the endoscope handpiece or lumen. Further, the data may be issued at the frame rate for the image sensor. This allows for increased (i.e., faster) system response. The camera system is then configured to decode the hidden information and act accordingly.

Figure 12:
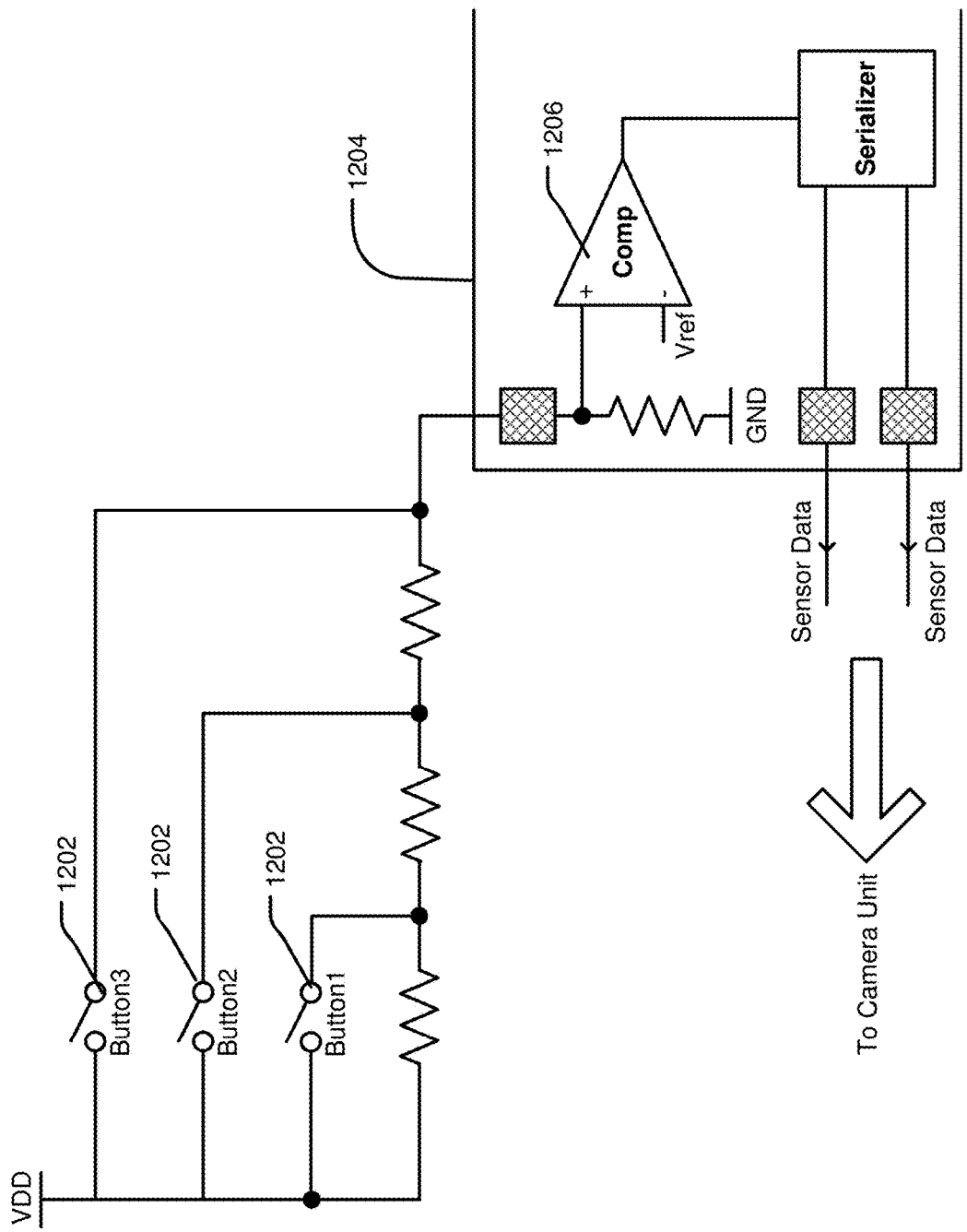
FIG. 12 is a circuit diagram illustrating an embodiment of a circuit that includes connections between endoscope buttons and the image sensor based upon a resistance network.

FIG. 12 is a circuit diagram illustrating an embodiment of a circuit that includes connections between the endoscope buttons 1202 and the image sensor 1204 based upon a resistance network. In this approach, a series of on-chip comparators 1206 may convert the analog signal into a digital word ready to be issued as output data.

Figure 13:
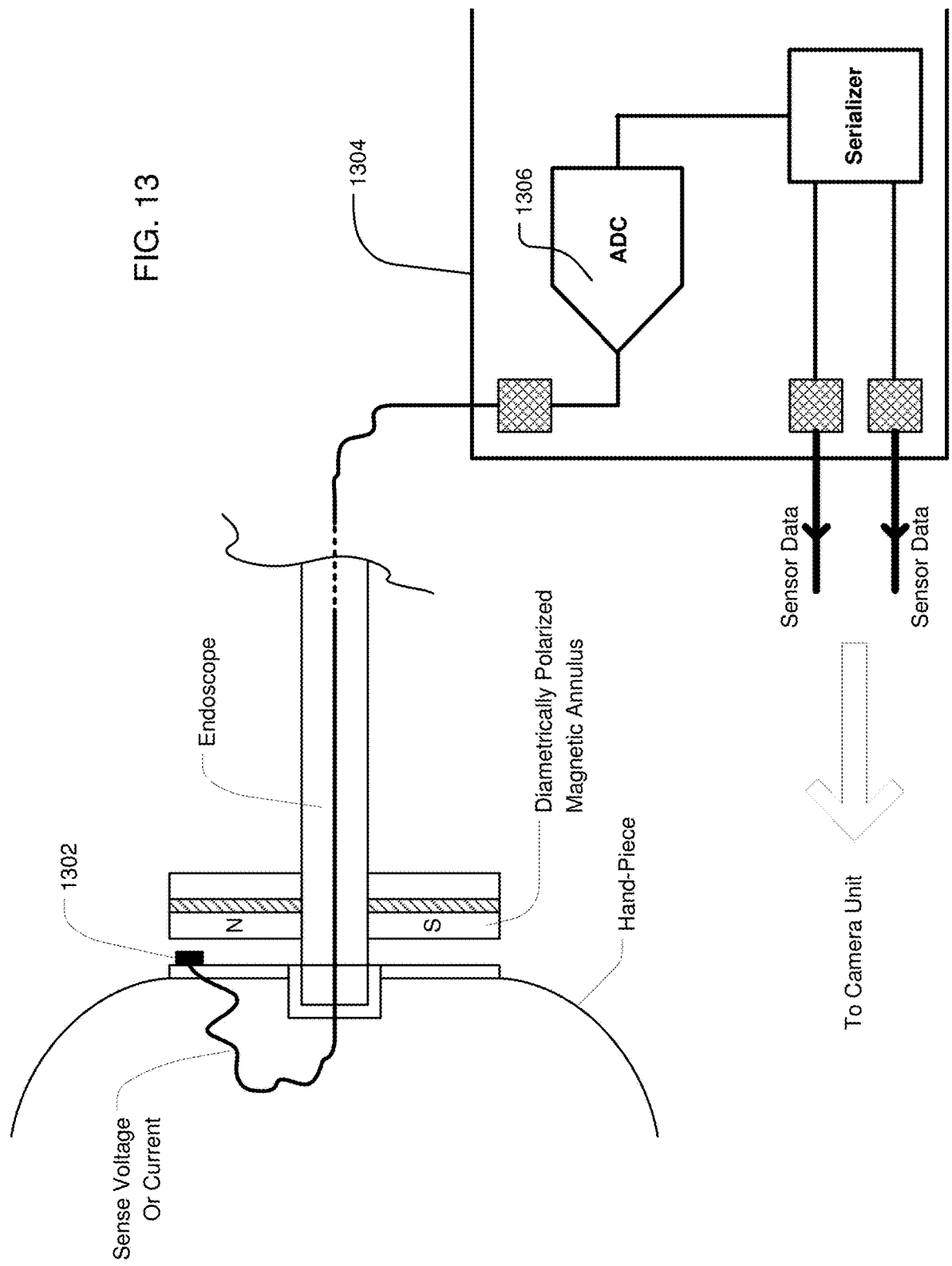
FIG. 13 is a circuit diagram illustrating an embodiment of a circuit in which an angular position Hall Effect sensor delivers an analog voltage directly to an image sensor.

FIG. 13 is a circuit diagram illustrating an embodiment of a circuit in which an angular position Hall Effect sensor 1302 delivers an analog voltage directly to the image sensor 1304. In this case, the analog voltage may be converted by an on-chip analog-digital converter (ADC) 1306 and inserted within the exposure frame.

Figure 14:
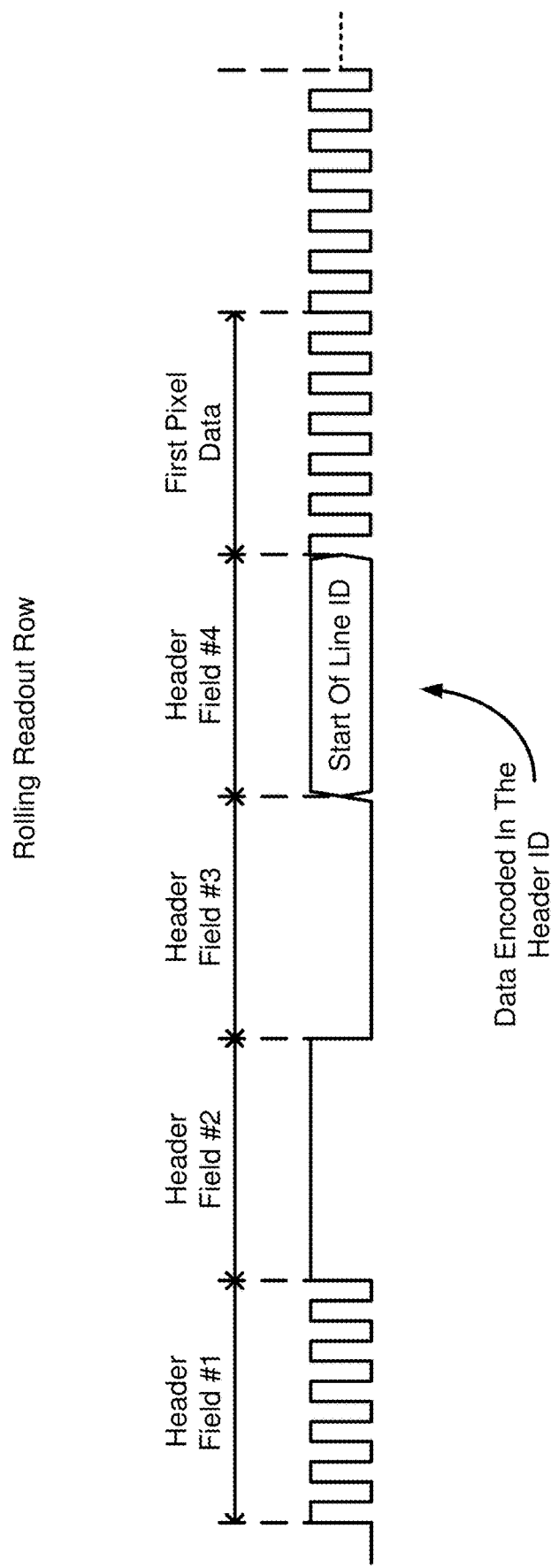
FIG. 14 illustrates an encoding example for digital data words within exposure frame data.
Figure 15:
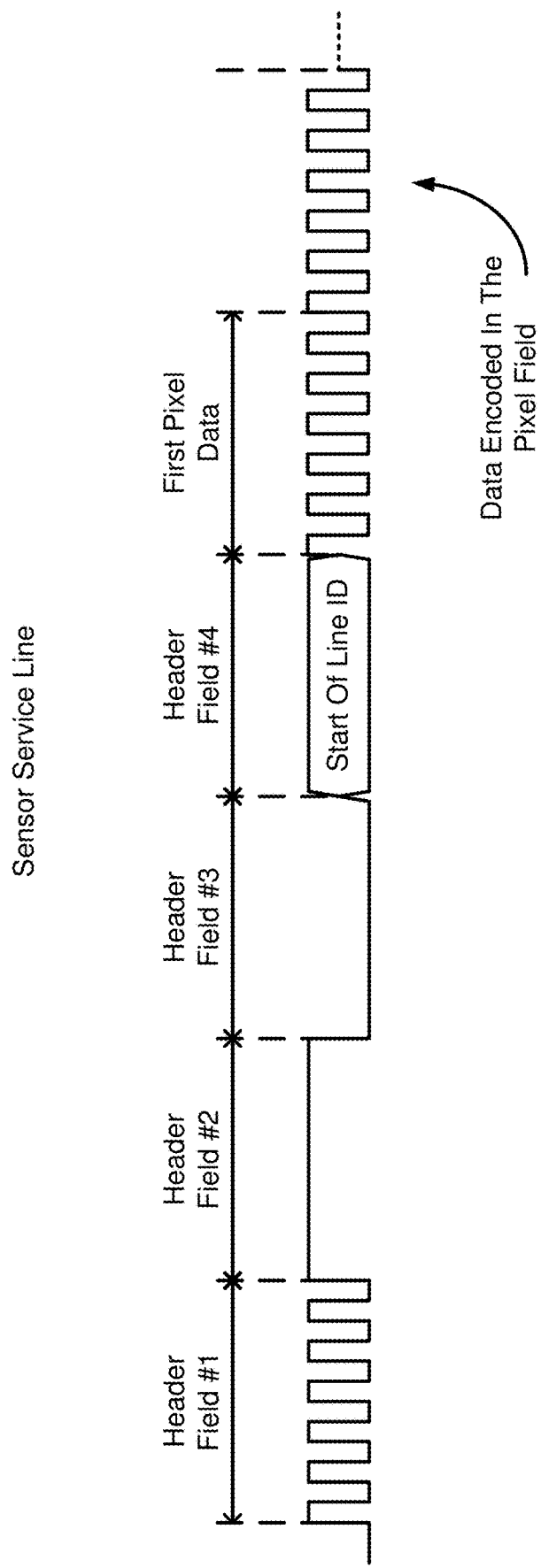
FIG. 15 illustrates an encoding example for digital data words within exposure frame data.

FIGS. 14 and 15 illustrate two possible encoding examples for digital data words within the exposure frame data. FIG. 14 illustrates a rolling readout row and FIG. 15 illustrates a sensor service line.

In FIG. 14, data words are encoded in the header ID at the start of the line ID as illustrated. The data words may be inserted in the row header. In FIG. 15, data words are encoded in the pixel field. The data words may replace pixel data within service rows of the pixel array. It should be noted that there are multiple other configurations for encoding digital data words within the image data generated by the image sensor and all such configurations are intended to fall within the scope of this disclosure.

Figure 16:
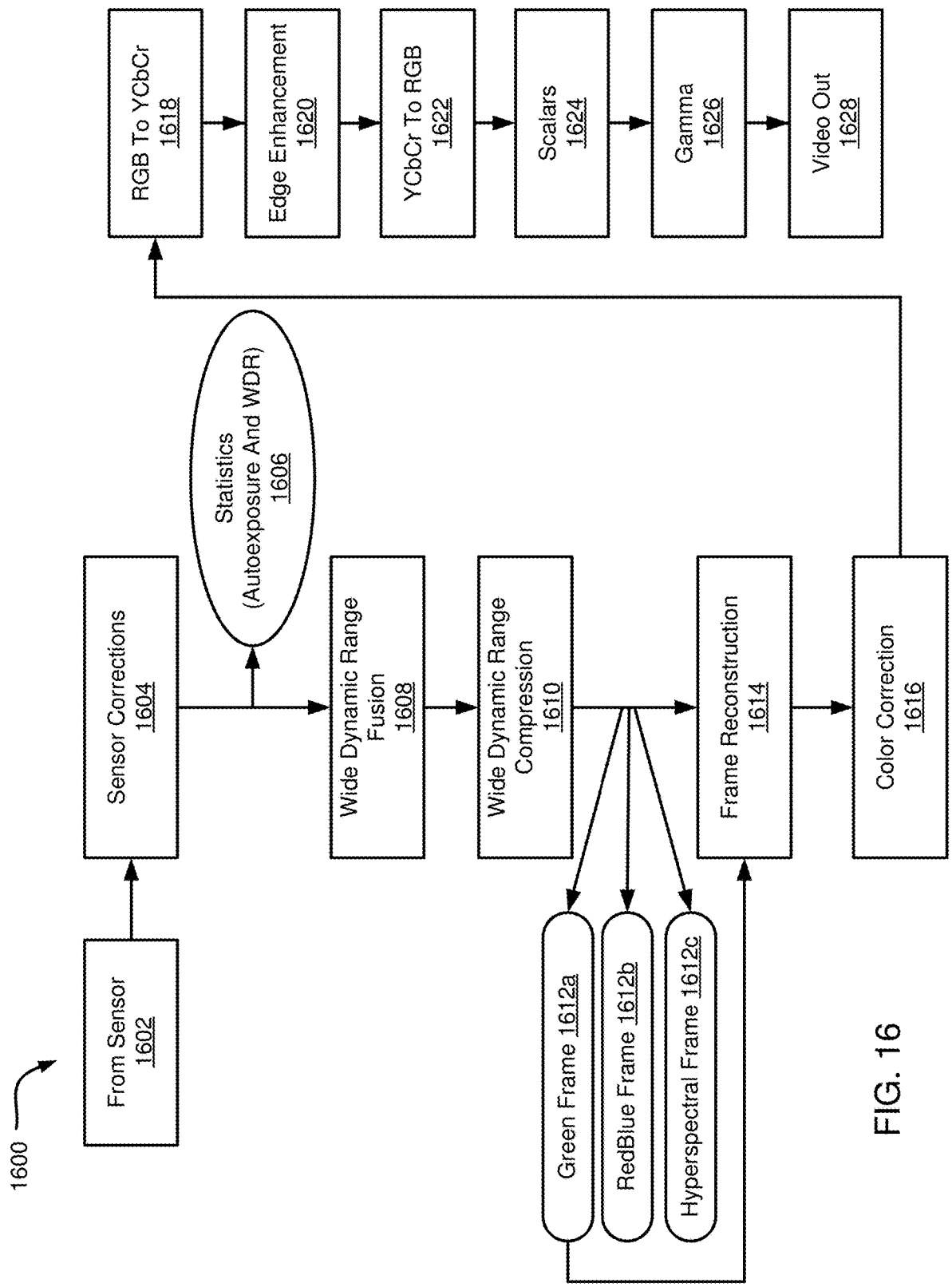
FIG. 16 is a schematic diagram of a process flow for applying correction algorithms and frame reconstruction to a plurality of exposure frames for generating an RGB image frame with hyperspectral data overlaid thereon.

FIG. 16 is a schematic diagram of a process flow 1600 to be implemented by a controller and/or monochrome image signal processor (ISP) for generating a video stream having RGB images with hyperspectral data overlaid thereon. In the process flow 1600, before applying gamma 1626 to place the image data in the standard sRGB color space, additional operations including edge enhancement 1620 and other adjustments are performed in an alternative color space such as the YCbCr or HSL color spaces. In the example process flow 1600, the RGB image data is converted to YCbCr to apply edge enhancement 1620 in the luminance plane and conduct filtering of the chrominance planes, and then the YCbCr image is converted back to linear RGB color space.

The process flow 1600 results in images with increased dynamic range. The image signal processor (ISP) chain may be assembled for the purpose of generating sRGB image sequences from raw sensor data, yielded in the presence of the G-R-G-B-Hyperspectral light pulsing scheme. In the process flow 1600, the first stage is concerned with making corrections to account for any non-idealities in the sensor technology for which it is most appropriate to work in the raw data domain. At the next stage, multiple frames (for example, a green frame 1612a, a red-blue frame 1612b, and a hyperspectral frame 1612c) are buffered because each final frame derives data from multiple raw frames. The frame reconstruction at 1614 proceeds by sampling data from a current frame and buffered frames (see 1612a, 1612b, and/or 1612c). The reconstruction process results in full color frames in linear RGB color space that include hyperspectral image data.

In an embodiment, the process flow 1600 is applied to checkerboard readings from a pixel array (see FIGS. 8-14). The checkerboard readings may be sensed in response to an R-G-B-G-Hyperspectral or Y-Cb-Y-Cr-Hyperspectral pulsing scheme. The process flow 1600 includes receiving data from an image sensor at 1602. Sensor correction calculations are performed at 1604. These sensor correction calculations can be used to determine statistics at 1606 such as autoexposure settings and wide dynamic range settings. The process flow 1600 continues and wide dynamic range fusion is processed at 1608. Wide dynamic range compression is processed at 1610. The wide dynamic range compression from 1610 can be fed to generate a green frame 1612a, a red-blue frame 1612, and/or a hyperspectral 1612c. The process flow 1600 continues and frame reconstruction is processed at 1614 and then color correction is processed at 1616. The process flow 1600 continues and an RGB (red-green-blue) image is converted to a YCbCr image at 1618. Edge enhancement is processed at 1620 and then the YCbCr image is converted back to an RGB image at 1622. Scalars are processed at 1624 and gamma is processed at 1626. The video is then exported at 1628.

In an embodiment, the wide dynamic range fusion at 1608 is executed after dark frame subtraction such that the mean black offset has been adjusted to zero and the data may be signed. In an embodiment, it is desirable to have the fixed pattern noise removed. The aim of the wide dynamic range fusion 1608 process may be to combine the data from two or more separate exposure frames into a single image frame prior to color fusion. This may be accomplished by separating the two components of the checkerboard pattern into two separate buffers and filling in the gaps by interpolation. There may be only one general kernel required because every empty pixel sees the same local environment except for pixels near the edges of the image. A suitable convolution kernel for filling in the checkerboard pattern by simple linear interpolation is:

$$\begin{pmatrix} 0 & \frac{1}{4} & 0 \\ \frac{1}{4} & 0 & \frac{1}{4} \\ 0 & \frac{1}{4} & 0 \end{pmatrix}$$

Following interpolation there may be two samples for each pixel location. A gain may be applied to the short exposure sample, which may be equal to the exposure-time ratio, $T_L/T_S$. This requires the addition of one extra bit for each factor-two of ratio. The fusion itself involves making a weighted sum of the two samples:

$$x_f = \gamma \cdot \left(\frac{T_L}{T_S}\right) \cdot x_S + (1-\gamma) x_L$$

Where $x_S$ and $x_L$ may be the (signed) short and long exposure signals respectively. The $\gamma$ factor may be a function of the long exposure signal, $x_L$, and may be set according to two thresholds, $\tau_1$ and $\tau_2$. Below $x_L=17$, $\gamma=0.0$, above $\gamma=\tau_2$, $\gamma=1.0$. Between the thresholds, various functional forms may be employed and linear and cubic example behaviors of $\gamma$ between $\tau_1$ and $\tau_2$, may be drawn. The value of $\tau_2$ may be set to the maximum possible value of $x_L$, e.g., or something just below it. The purpose of the lower threshold, $\tau_1$, may be to limit the influence of read noise from the short sample which has the gain factor $T_L/T_S$ applied to it. It can be set to a conservatively high constant, to accommodate the maximum ratio E, but it may be more beneficial to have it vary linearly with $T_L/T_S$;

$$\tau_1 = \left(\frac{T_L}{T_S}\right) \cdot \eta$$

The provision of two or more exposure frames within the same image frame within a pulsed illumination endoscopy system may also be exploited for the purpose of reducing the number of captured exposure frames per final full-color image from, from three to two. This suppresses possible color motion artifacts that may be associated with an endoscopic imaging system.

An inherent property of the monochrome wide dynamic range array may be that the pixels that have the long integration time may be integrate a superset of the light seen by the short integration time pixels. For regular wide dynamic operation in the luminance exposure frames, that may be desirable. For the chrominance exposure frames, it means that the pulsing may be controlled in conjunction with the exposure periods so as to e.g. provide $\lambda Y+Cb$ from the start of the long exposure and switch to $\delta Y+Cr$ at the point that the short pixels may be turned on (both pixel types have their charges transferred at the same time). $\lambda$ and $\delta$ may be two tunable factors that may be used to bring all pulse energies to positive values.

During color correction 1616 in the ISP, the two flavors of pixel may be separated into two buffers. The empty pixels are filled in using linear interpolation. At this point, one buffer would contain a full image of $\delta Y+Cr$ data and the other contains $\delta Y+Cr+\lambda Y+Cb$ imaging data. The $\delta Y+Cr$ buffer would be subtracted from the second buffer to give $\lambda Y+Cb$. Then the appropriate proportion of luminance data from the luminance exposure frames would be subtracted out for each.

Figure 17:
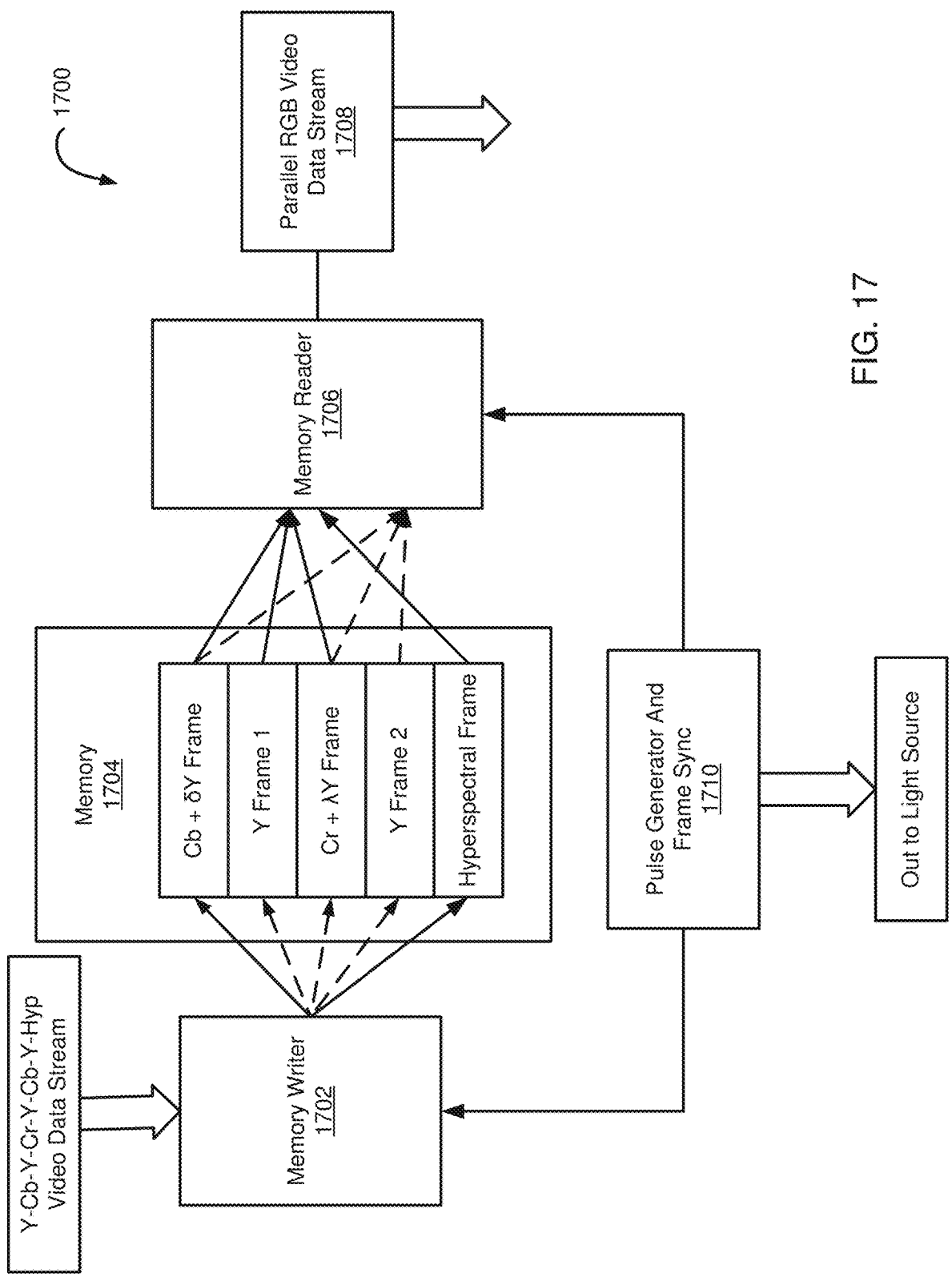
FIG. 17 is a schematic diagram of color fusion hardware.

FIG. 17 is an example of color fusion hardware 1700. The color fusion hardware 1700 is deployed for generating an image frame according to a pulsed lighting scheme as discussed herein. The color fusion process is more straightforward than de-mosaic, which is necessitated by image sensors with a color filter array, because there is no spatial interpolation. The color fusion process performed by the color fusion hardware 1700 does not require buffering of exposure frames to have all necessary information available for each pixel.

The memory writer 1702 receives a video data stream. In an embodiment, the video data stream includes Y-Cb-Y-Cr-Y-Cb-Y-Hyperspectral exposure frames. In an alternative embodiment, the video data stream includes R-G-B-G-Hyperspectral exposure frames. The video data stream may include YCbCr or RGB exposure frames in combination with one or more of hyperspectral exposure frames, fluorescence exposure frames, and/or laser mapping or tool tracking exposure frames.

The memory writer 1702 writes the video data stream to memory 1704. The video data stream may be parsed into, for example, a $Cb+\delta Y$ exposure frame, one or more luminance exposure frames, a $Cr+\lambda Y$ exposure frame, a hyperspectral exposure frame, a fluorescence exposure frame, and/or a laser mapping exposure frame. Alternatively, the video data stream may be parsed into, for example, a red exposure frame, one or more green exposure frames, a blue exposure frame, a hyperspectral exposure frame, a fluorescence exposure frame, and/or a laser mapping exposure frame. The different exposure frames are read by the memory reader 1706 and a parallel RGB video data stream is generated at 1708. The pulse generator and frame sync 1710 sends information to the memory writer 1704 and the memory reader 1706 to aid in fusing the multiple exposure frames. Information is output to the light source by the pulse generator and frame sync 1710.

Figure 18:
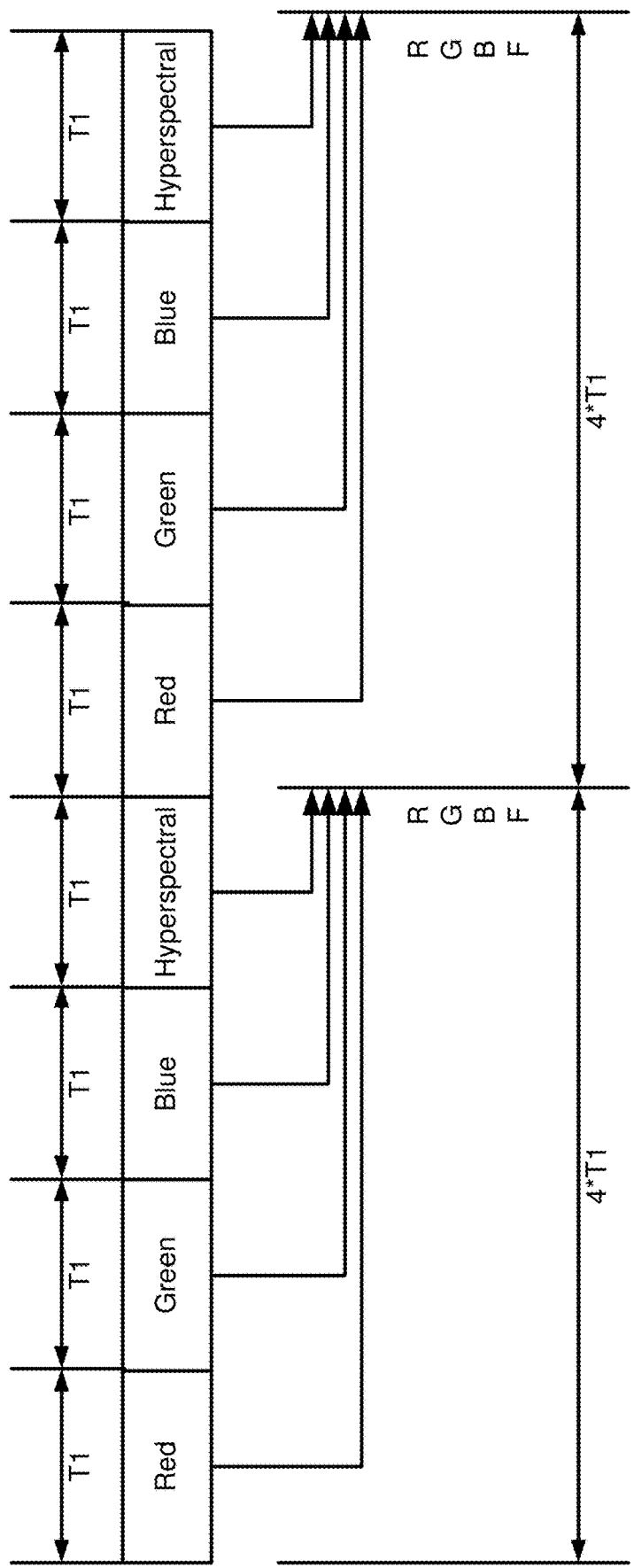
FIG. 18 is a schematic diagram of a pattern reconstruction process for generating an RGB image with hyperspectral data overlaid thereon by pulsing partitioned spectrums of light.

FIG. 18 is a schematic diagram of a pattern reconstruction process. The example pattern illustrated in FIG. 18 includes Red, Green, Blue, and Hyperspectral pulses of light that each last a duration of T1. In various embodiments, the pulses of light may be of the same duration or of differing durations. The Red, Green, Blue, and Hyperspectral exposure frames are combined to generate an RGB image with hyperspectral data overlaid thereon. A single image frame comprising a red exposure frame, a green exposure frame, a blue exposure frame, and a hyperspectral exposure frame requires a time period of 4*T1 to be generated. The time durations shown in FIG. 18 are illustrative only and may vary for different implementations. In other embodiments, different pulsing schemes may be employed. For example, embodiments may be based on the timing of each color component or frame (T1) and the reconstructed frame having a period twice that of the incoming color frame (2×T1). Different frames within the sequence may have different frame periods and the average capture rate could be any multiple of the final frame rate.

In an embodiment, the dynamic range of the system is increased by varying the pixel sensitivities of pixels within the pixel array of the image sensor. Some pixels may sense reflected electromagnetic radiation at a first sensitivity level, other pixels may sense reflected electromagnetic radiation at a second sensitivity level, and so forth. The different pixel sensitivities may be combined to increase the dynamic range provided by the pixel configuration of the image sensor. In an embodiment, adjacent pixels are set at different sensitivities such that each cycle includes data produced by pixels that are more and less sensitive with respect to each other. The dynamic range is increased when a plurality of sensitivities are recorded in a single cycle of the pixel array. In an embodiment, wide dynamic range can be achieved by having multiple global TX, each TX firing only on a different set of pixels. For example, in global mode, a global TX1 signal is firing a set 1 of pixels, a global TX2 signal is firing a set 2 of pixel, a global TXn signal is firing a set n of pixels, and so forth.

Figure 19A:
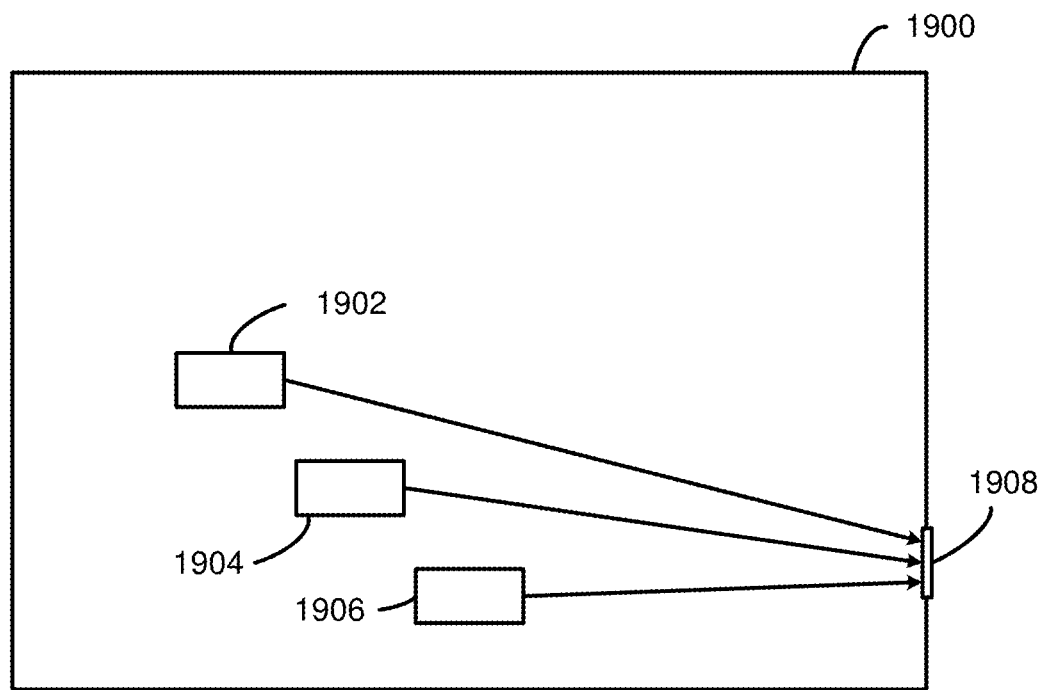
FIGS. 19A-19C illustrate a light source having a plurality of emitters.
Figure 19B:
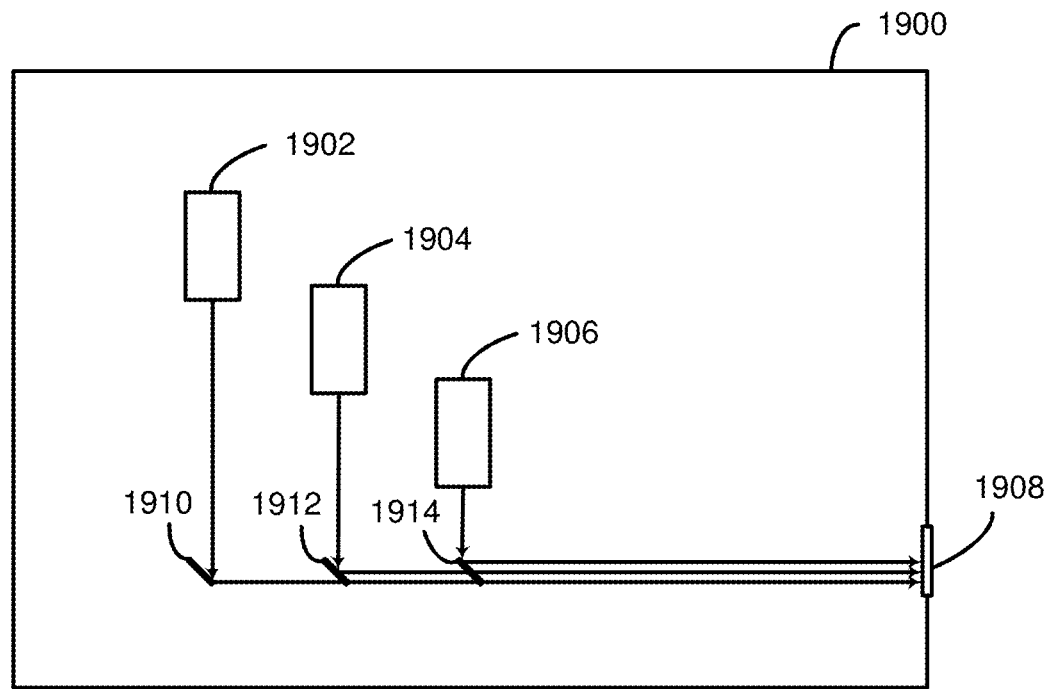
Figure 19C:
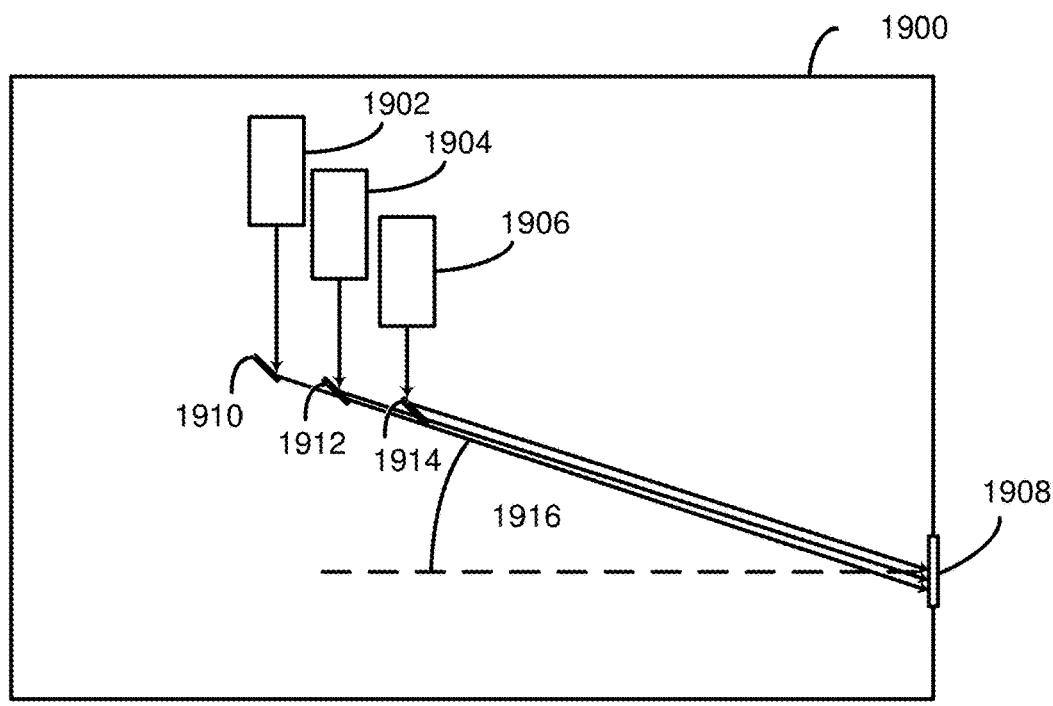

FIGS. 19A-19C each illustrate a light source 1900 having a plurality of emitters. The emitters include a first emitter 1902, a second emitter 1904, and a third emitter 1906. Additional emitters may be included, as discussed further below. The emitters 1902, 1904, and 1906 may include one or more laser emitters that emit light having different wavelengths. For example, the first emitter 1902 may emit a wavelength that is consistent with a blue laser, the second emitter 1904 may emit a wavelength that is consistent with a green laser, and the third emitter 1906 may emit a wavelength that is consistent with a red laser. For example, the first emitter 1902 may include one or more blue lasers, the second emitter 1904 may include one or more green lasers, and the third emitter 1906 may include one or more red lasers. The emitters 1902, 1904, 1906 emit laser beams toward a collection region 1908, which may be the location of a waveguide, lens, or other optical component for collecting and/or providing light to a waveguide, such as the jumper waveguide 206 or lumen waveguide 210 of FIG. 2.

In an implementation, the emitters 1902, 1904, and 1906 emit hyperspectral wavelengths of electromagnetic radiation. Certain hyperspectral wavelengths may pierce through tissue and enable a medical practitioner to "see through" tissues in the foreground to identify chemical processes, structures, compounds, biological processes, and so forth that are located behind the tissues in the foreground. The hyperspectral wavelengths may be specifically selected to identify a specific disease, tissue condition, biological process, chemical process, type of tissue, and so forth that is known to have a certain spectral response.

In an implementation where a patient has been administered a reagent or dye to aid in the identification of certain tissues, structures, chemical reactions, biological processes, and so forth, the emitters 1902, 1904, and 1906 may emit wavelength(s) for fluorescing the reagents or dyes. Such wavelength(s) may be determined based on the reagents or dyes administered to the patient. In such an embodiment, the emitters may need to be highly precise for emitting desired wavelength(s) to fluoresce or activate certain reagents or dyes.

In an implementation, the emitters 1902, 1904, and 1906 emit a laser mapping pattern for mapping a topology of a scene and/or for calculating dimensions and distances between objects in the scene. In an embodiment, the endoscopic imaging system is used in conjunction with multiple tools such as scalpels, retractors, forceps, and so forth. In such an embodiment, each of the emitters 1902, 1904, and 1906 may emit a laser mapping pattern such that a laser mapping pattern is projected on to each tool individually. In such an embodiment, the laser mapping data for each of the tools can be analyzed to identify distances between the tools and other objects in the scene.

In the embodiment of FIG. 19B, the emitters 1902, 1904, 1906 each deliver laser light to the collection region 1908 at different angles. The variation in angle can lead to variations where electromagnetic energy is located in an output waveguide. For example, if the light passes immediately into a fiber bundle (glass or plastic) at the collection region 1908, the varying angles may cause different amounts of light to enter different fibers. For example, the angle may result in intensity variations across the collection region 1908. Furthermore, light from the different emitters may not be homogenously mixed so some fibers may receive different amounts of light of different colors. Variation in the color or intensity of light in different fibers can lead to non-optimal illumination of a scene. For example, variations in delivered light or light intensities may result at the scene and captured images.

In one embodiment, an intervening optical element may be placed between a fiber bundle and the emitters 1902, 1904, 1906 to mix the different colors (wavelengths) of light before entry into the fibers or other waveguide. Example intervening optical elements include a diffuser, mixing rod, one or more lenses, or other optical components that mix the light so that a given fiber receive a same amount of each color (wavelength). For example, each fiber in the fiber bundle may have a same color. This mixing may lead to the same color in each fiber but may, in some embodiments, still result in different total brightness delivered to different fibers. In one embodiment, the intervening optical element may also spread out or even out the light over the collection region so that each fiber carries the same total amount of light (e.g., the light may be spread out in a top hat profile). A diffuser or mixing rod may lead to loss of light.

Although the collection region 1908 is represented as a physical component in FIG. 19A, the collection region 1908 may simply be a region where light from the emitters 1902, 1904, and 1906 is delivered. In some cases, the collection region 1908 may include an optical component such as a diffuser, mixing rod, lens, or any other intervening optical component between the emitters 1902, 1904, 1906 and an output waveguide.

FIG. 19C illustrates an embodiment of a light source 1900 with emitters 1902, 1904, 1906 that provide light to the collection region 1908 at the same or substantially same angle. The light is provided at an angle substantially perpendicular to the collection region 1908. The light source 1900 includes a plurality of dichroic mirrors including a first dichroic mirror 1910, a second dichroic mirror 1912, and a third dichroic mirror 1914. The dichroic mirrors 1910, 1912, 1914 include mirrors that reflect a first wavelength of light but transmit (or are transparent to) a second wavelength of light. For example, the third dichroic mirror 1914 may reflect blue laser light provided by the third emitter, while being transparent to the red and green light provided by the first emitter 1902 and the second emitter 1904, respectively. The second dichroic mirror 1912 may be transparent to red light from the first emitter 1902, but reflective to green light from the second emitter 1904. If other colors or wavelengths are included dichroic mirrors may be selected to reflect light corresponding to at least one emitter and be transparent to other emitters. For example, the third dichroic mirror 1914 reflect the light form the third emitter 1906 but is to emitters "behind" it, such as the first emitter 1902 and the second emitter 1904. In embodiments where tens or hundreds of emitters are present, each dichroic mirror may be reflective to a corresponding emitter and emitters in front of it while being transparent to emitters behind it. This may allow for tens or hundreds of emitters to emit electromagnetic energy to the collection region 1908 at a substantially same angle.

Because the dichroic mirrors allow other wavelengths to transmit or pass through, each of the wavelengths may arrive at the collection region 1908 from a same angle and/or with the same center or focal point. Providing light from the same angle and/or same focal/center point can significantly improve reception and color mixing at the collection region 1908. For example, a specific fiber may receive the different colors in the same proportions they were transmitted/reflected by the emitters 1902, 1904, 1906 and mirrors 1910, 1912, 1914. Light mixing may be significantly improved at the collection region compared to the embodiment of FIG. 19B. In one embodiment, any optical components discussed herein may be used at the collection region 1908 to collect light prior to providing it to a fiber or fiber bundle.

FIG. 19C illustrates an embodiment of a light source 1900 with emitters 1902, 1904, 1906 that also provide light to the collection region 1908 at the same or substantially same angle. However, the light incident on the collection region 1908 is offset from being perpendicular. Angle 1916 indicates the angle offset from perpendicular. In one embodiment, the laser emitters 1902, 1904, 1906 may have cross sectional intensity profiles that are Gaussian. As discussed previously, improved distribution of light energy between fibers may be accomplished by creating a more flat or top-hat shaped intensity profile. In one embodiment, as the angle 1916 is increased, the intensity across the collection region 1908 approaches a top hat profile. For example, a top-hat profile may be approximated even with a non-flat output beam by increasing the angle 1916 until the profile is sufficiently flat. The top hat profile may also be accomplished using one or more lenses, diffusers, mixing rods, or any other intervening optical component between the emitters 1902, 1904, 1906 and an output waveguide, fiber, or fiber optic bundle.

Figure 20:
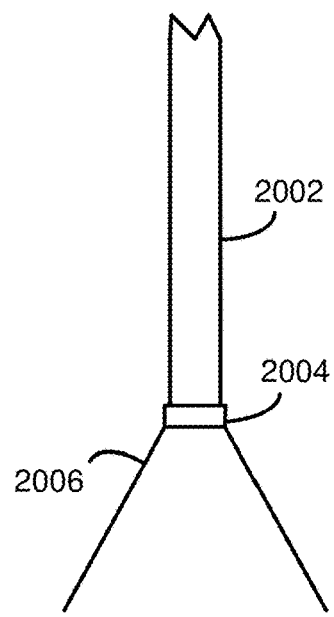
FIG. 20 illustrates a single optical fiber outputting via a diffuser at an output to illuminate a scene in a light deficient environment.

FIG. 20 is a schematic diagram illustrating a single optical fiber 2002 outputting via a diffuser 2004 at an output. In one embodiment, the optical fiber 2002 has a diameter of 500 microns, a numerical aperture of 0.65, and emits a light cone 2006 of about 70 or 80 degrees without a diffuser 2004. With the diffuser 2004, the light cone 2006 may have an angle of about 110 or 120 degrees. The light cone 2006 may be a majority of where all light goes and is evenly distributed. The diffuser 2004 may allow for more even distribution of electromagnetic energy of a scene observed by an image sensor.

In one embodiment, the lumen waveguide 210 includes a single plastic or glass optical fiber of about 500 microns. The plastic fiber may be low cost, but the width may allow the fiber to carry a sufficient amount of light to a scene, with coupling, diffusion, or other losses. For example, smaller fibers may not be able to carry as much light or power as a larger fiber. The lumen waveguide 210 may include a single or a plurality of optical fibers. The lumen waveguide 210 may receive light directly from the light source or via a jumper waveguide. A diffuser may be used to broaden the light output 206 for a desired field of view of the image sensor 214 or other optical components.

Although three emitters are shown in FIGS. 19A-19C, emitters numbering from one into the hundreds or more may be used in some embodiments. The emitters may have different wavelengths or spectrums of light that they emit, and which may be used to contiguously cover a desired portion of the electromagnetic spectrum (e.g., the visible spectrum as well as infrared and ultraviolet spectrums). The emitters may be configured to emit visible light such as red light, green light, and blue light, and may further be configured to emit hyperspectral emissions of electromagnetic radiation, fluorescence excitation wavelengths for fluorescing a reagent, and/or laser mapping patterns for calculating parameters and distances between objects in a scene.

Figure 21:
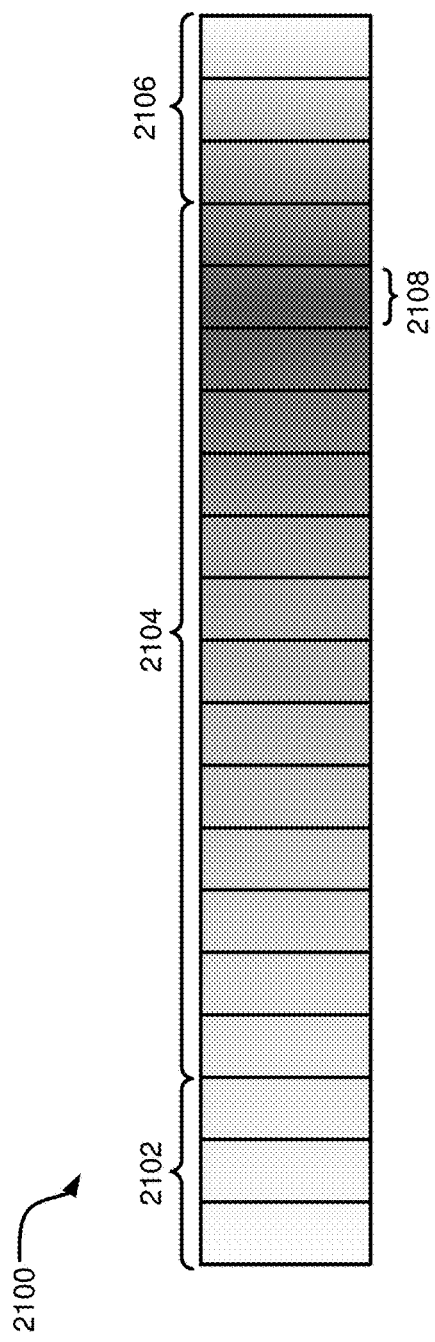
FIG. 21 illustrates a portion of the electromagnetic spectrum divided into a plurality of different sub-spectrums which may be emitted by emitters of a light source in accordance with the principles and teachings of the disclosure.

FIG. 21 illustrates a portion of the electromagnetic spectrum 2100 divided into twenty different sub-spectrums. The number of sub-spectrums is illustrative only. In at least one embodiment, the spectrum 2100 may be divided into hundreds of sub-spectrums, each with a small waveband. The spectrum may extend from the infrared spectrum 2102, through the visible spectrum 2104, and into the ultraviolet spectrum 2106. The sub-spectrums each have a waveband 2108 that covers a portion of the spectrum 2100. Each waveband may be defined by an upper wavelength and a lower wavelength.

Hyperspectral imaging includes imaging information from across the electromagnetic spectrum 2100. A hyperspectral pulse of electromagnetic radiation may include a plurality of sub-pulses spanning one or more portions of the electromagnetic spectrum 2100 or the entirety of the electromagnetic spectrum 2100. A hyperspectral pulse of electromagnetic radiation may include a single partition of wavelengths of electromagnetic radiation. A resulting hyperspectral exposure frame includes information sensed by the pixel array subsequent to a hyperspectral pulse of electromagnetic radiation. Therefore, a hyperspectral exposure frame may include data for any suitable partition of the electromagnetic spectrum 2100 and may include multiple exposure frames for multiple partitions of the electromagnetic spectrum 2100. In an embodiment, a hyperspectral exposure frame includes multiple hyperspectral exposure frames such that the combined hyperspectral exposure frame comprises data for the entirety of the electromagnetic spectrum 2100.

In one embodiment, at least one emitter (such as a laser emitter) is included in a light source (such as the light sources 202, 1900) for each sub-spectrum to provide complete and contiguous coverage of the whole spectrum 2100. For example, a light source for providing coverage of the illustrated sub-spectrums may include at least 20 different emitters, at least one for each sub-spectrum. In one embodiment, each emitter covers a spectrum covering 40 nanometers. For example, one emitter may emit light within a waveband from 500 nm to 540 nm while another emitter may emit light within a waveband from 540 nm to 580 nm. In another embodiment, emitters may cover other sizes of wavebands, depending on the types of emitters available or the imaging needs. For example, a plurality of emitters may include a first emitter that covers a waveband from 500 to 540 nm, a second emitter that covers a waveband from 540 nm to 640 nm, and a third emitter that covers a waveband from 640 nm to 650 nm. Each emitter may cover a different slice of the electromagnetic spectrum ranging from far infrared, mid infrared, near infrared, visible light, near ultraviolet and/or extreme ultraviolet. In some cases, a plurality of emitters of the same type or wavelength may be included to provide sufficient output power for imaging. The number of emitters needed for a specific waveband may depend on the sensitivity of a monochrome sensor to the waveband and/or the power output capability of emitters in that waveband.

The waveband widths and coverage provided by the emitters may be selected to provide any desired combination of spectrums. For example, contiguous coverage of a spectrum using very small waveband widths (e.g., 10 nm or less) may allow for highly selective hyperspectral and/or fluorescence imaging. The waveband widths may allow for selectively emitting the excitation wavelength(s) for one or more particular fluorescent reagents. Additionally, the waveband widths may allow for selectively emitting certain partitions of hyperspectral electromagnetic radiation for identifying specific structures, chemical processes, tissues, biological processes, and so forth. Because the wavelengths come from emitters which can be selectively activated, extreme flexibility for fluorescing one or more specific fluorescent reagents during an examination can be achieved. Additionally, extreme flexibility for identifying one or more objects or processes by way of hyperspectral imaging can be achieved. Thus, much more fluorescence and/or hyperspectral information may be achieved in less time and within a single examination which would have required multiple examinations, delays because of the administration of dyes or stains, or the like.

Figure 22:
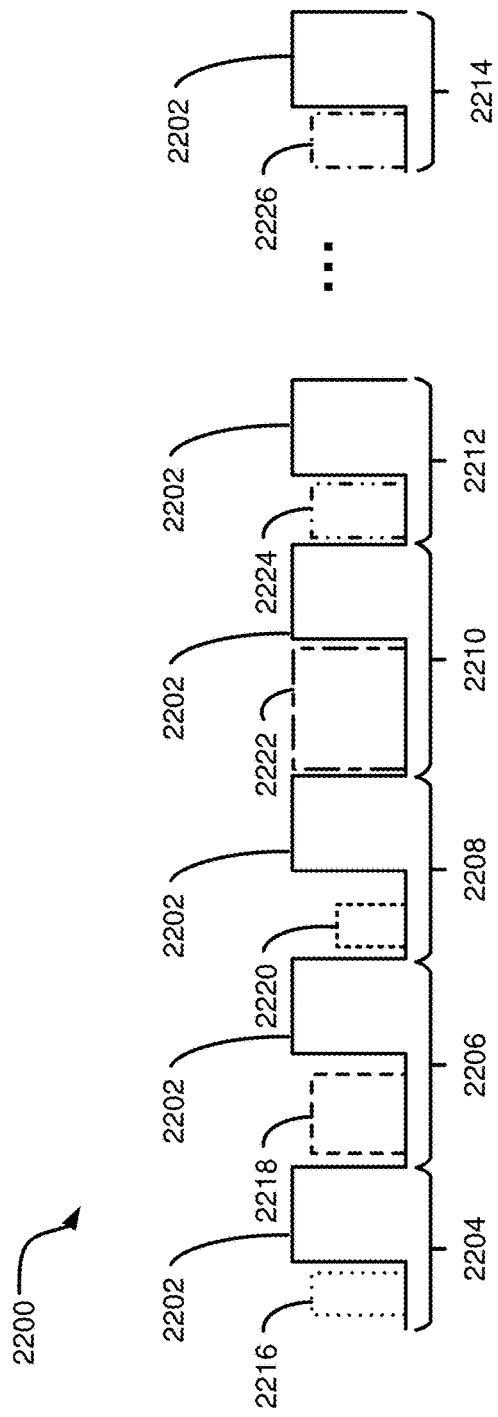
FIG. 22 is a schematic diagram illustrating a timing sequence for emission and readout for generating an image frame comprising a plurality of exposure frames resulting from differing partitions of pulsed light.

FIG. 22 is a schematic diagram illustrating a timing diagram 2200 for emission and readout for generating an image. The solid line represents readout (peaks 2202) and blanking periods (valleys) for capturing a series of exposure frames 2204-2214. The series of exposure frames 2204-2214 may include a repeating series of exposure frames which may be used for generating laser mapping, hyperspectral, and/or fluorescence data that may be overlaid on an RGB video stream. In an embodiment, a single image frame comprises information from multiple exposure frames, wherein one exposure frame includes red image data, another exposure frame includes green image data, and another exposure frame includes blue image data. Additionally, the single image frame may include one or more of hyperspectral image data, fluorescence image data, and laser mapping data. The multiple exposure frames are combined to produce the single image frame. The single image frame is an RGB image with hyperspectral imaging data. The series of exposure frames include a first exposure frame 2204, a second exposure frame 2206, a third exposure frame 2208, a fourth exposure frame 2210, a fifth exposure frame 2212, and an Nth exposure frame 2226.

Additionally, the hyperspectral image data, the fluorescence image data, and the laser mapping data can be used in combination to identify critical tissues or structures and further to measure the dimensions of those critical tissues or structures. For example, the hyperspectral image data may be provided to a corresponding system to identify certain critical structures in a body such as a nerve, ureter, blood vessel, cancerous tissue, and so forth. The location and identification of the critical structures may be received from the corresponding system and may further be used to generate topology of the critical structures using the laser mapping data. For example, a corresponding system determines the location of a cancerous tumor based on hyperspectral imaging data. Because the location of the cancerous tumor is known based on the hyperspectral imaging data, the topology and distances of the cancerous tumor may then be calculated based on laser mapping data. This example may also apply when a cancerous tumor or other structure is identified based on fluorescence imaging data.

In one embodiment, each exposure frame is generated based on at least one pulse of electromagnetic energy. The pulse of electromagnetic energy is reflected and detected by an image sensor and then read out in a subsequent readout (2202). Thus, each blanking period and readout results in an exposure frame for a specific spectrum of electromagnetic energy. For example, the first exposure frame 2204 may be generated based on a spectrum of a first one or more pulses 2216, a second exposure frame 2206 may be generated based on a spectrum of a second one or more pulses 2218, a third exposure frame 2208 may be generated based on a spectrum of a third one or more pulses 2220, a fourth exposure frame 2210 may be generated based on a spectrum of a fourth one or more pulses 2222, a fifth exposure frame 2212 may be generated based on a spectrum of a fifth one or more pulses 2424, and an Nth exposure frame 2226 may be generated based on a spectrum of an Nth one or more pulses 2226.

The pulses 2216-2226 may include energy from a single emitter or from a combination of two or more emitters. For example, the spectrum included in a single readout period or within the plurality of exposure frames 2204-2214 may be selected for a desired examination or detection of a specific tissue or condition. According to one embodiment, one or more pulses may include visible spectrum light for generating an RGB or black and white image while one or more additional pulses are emitted to sense a spectral response to a hyperspectral wavelength of electromagnetic radiation. For example, pulse 2216 may include red light, pulse 2218 may include blue light, and pulse 2220 may include green light while the remaining pulses 2222-2226 may include wavelengths and spectrums for detecting a specific tissue type, fluorescing a reagent, and/or mapping the topology of the scene. As a further example, pulses for a single readout period include a spectrum generated from multiple different emitters (e.g., different slices of the electromagnetic spectrum) that can be used to detect a specific tissue type. For example, if the combination of wavelengths results in a pixel having a value exceeding or falling below a threshold, that pixel may be classified as corresponding to a specific type of tissue. Each frame may be used to further narrow the type of tissue that is present at that pixel (e.g., and each pixel in the image) to provide a very specific classification of the tissue and/or a state of the tissue (diseased/healthy) based on a spectral response of the tissue and/or whether a fluorescent reagent is present at the tissue.

The plurality of frames 2204-2214 is shown having varying lengths in readout periods and pulses having different lengths or intensities. The blanking period, pulse length or intensity, or the like may be selected based on the sensitivity of a monochromatic sensor to the specific wavelength, the power output capability of the emitter(s), and/or the carrying capacity of the waveguide.

In one embodiment, dual image sensors may be used to obtain three-dimensional images or video feeds. A three-dimensional examination may allow for improved understanding of a three-dimensional structure of the examined region as well as a mapping of the different tissue or material types within the region.

In an example implementation, a fluorescent reagent is provided to a patient, and the fluorescent reagent is configured to adhere to cancerous cells. The fluorescent reagent is known to fluoresce when radiated with a specific partition of electromagnetic radiation. The relaxation wavelength of the fluorescent reagent is also known. In the example implementation, the patient is imaged with an endoscopic imaging system as discussed herein. The endoscopic imaging system pulses partitions of red, green, and blue wavelengths of light to generate an RGB video stream of the interior of the patient's body. Additionally, the endoscopic imaging system pulses the excitation wavelength of electromagnetic radiation for the fluorescent reagent that was administered to the patient. In the example, the patient has cancerous cells and the fluorescent reagent has adhered to the cancerous cells. When the endoscopic imaging system pulses the excitation wavelength for the fluorescent reagent, the fluorescent reagent will fluoresce and emit a relaxation wavelength. If the cancerous cells are present in the scene being imaged by the endoscopic imaging system, then the fluorescent reagent will also be present in the scene and will emit its relaxation wavelength after fluorescing due to the emission of the excitation wavelength. The endoscopic imaging system senses the relaxation wavelength of the fluorescent reagent and thereby senses the presence of the fluorescent reagent in the scene. Because the fluorescent reagent is known to adhere to cancerous cells, the presence of the fluorescent reagent further indicates the presence of cancerous cells within the scene. The endoscopic imaging system thereby identifies the location of cancerous cells within the scene. The endoscopic imaging system may further emit a laser mapping pulsing scheme for generating a topology of the scene and calculating dimensions for objects within the scene. The location of the cancerous cells (as identified by the fluorescence imaging data) may be combined with the topology and dimensions information calculated based on the laser mapping data. Therefore, the precise location, size, dimensions, and topology of the cancerous cells may be identified. This information may be provided to a medical practitioner to aid in excising the cancerous cells. Additionally, this information may be provided to a robotic surgical system to enable the surgical system to excise the cancerous cells.

In a further example implementation, a patient is imaged with an endoscopic imaging system to identify quantitative diagnostic information about the patient's tissue pathology. In the example, the patient is suspected or known to suffer from a disease that can be tracked with hyperspectral imaging to observe the progression of the disease in the patient's tissue. The endoscopic imaging system pulses partitions of red, green, and blue wavelengths of light to generate an RGB video stream of the interior of the patient's body. Additionally, the endoscopic imaging system pulses one or more hyperspectral wavelengths of light that permit the system to "see through" some tissues and generate imaging of the tissue that is affected by the disease. The endoscopic imaging system senses the reflected hyperspectral electromagnetic radiation to generate hyperspectral imaging data of the diseased tissue, and thereby identifies the location of the diseased tissue within the patient's body. The endoscopic imaging system may further emit a laser mapping pulsing scheme for generating a topology of the scene and calculating dimensions of objects within the scene. The location of the diseased tissue (as identified by the hyperspectral imaging data) may be combined with the topology and dimensions information that is calculated with the laser mapping data. Therefore, the precise location, size, dimensions, and topology of the diseased tissue can be identified. This information may be provided to a medical practitioner to aid in excising, imaging, or studying the diseased tissue. Additionally, this information may be provided to a robotic surgical system to enable the surgical system to excise the diseased tissue.

FIGS. 23A and 23B illustrate a perspective view and a side view, respectively, of an implementation of a monolithic sensor 2300 having a plurality of pixel arrays for producing a three-dimensional image in accordance with the teachings and principles of the disclosure. Such an implementation may be desirable for three-dimensional image capture, wherein the two-pixel arrays 2302 and 2304 may be offset during use. In another implementation, a first pixel array 2302 and a second pixel array 2304 may be dedicated to receiving a predetermined range of wave lengths of electromagnetic radiation, wherein the first pixel array is dedicated to a different range of wavelength electromagnetic radiation than the second pixel array.

Figure 24A:
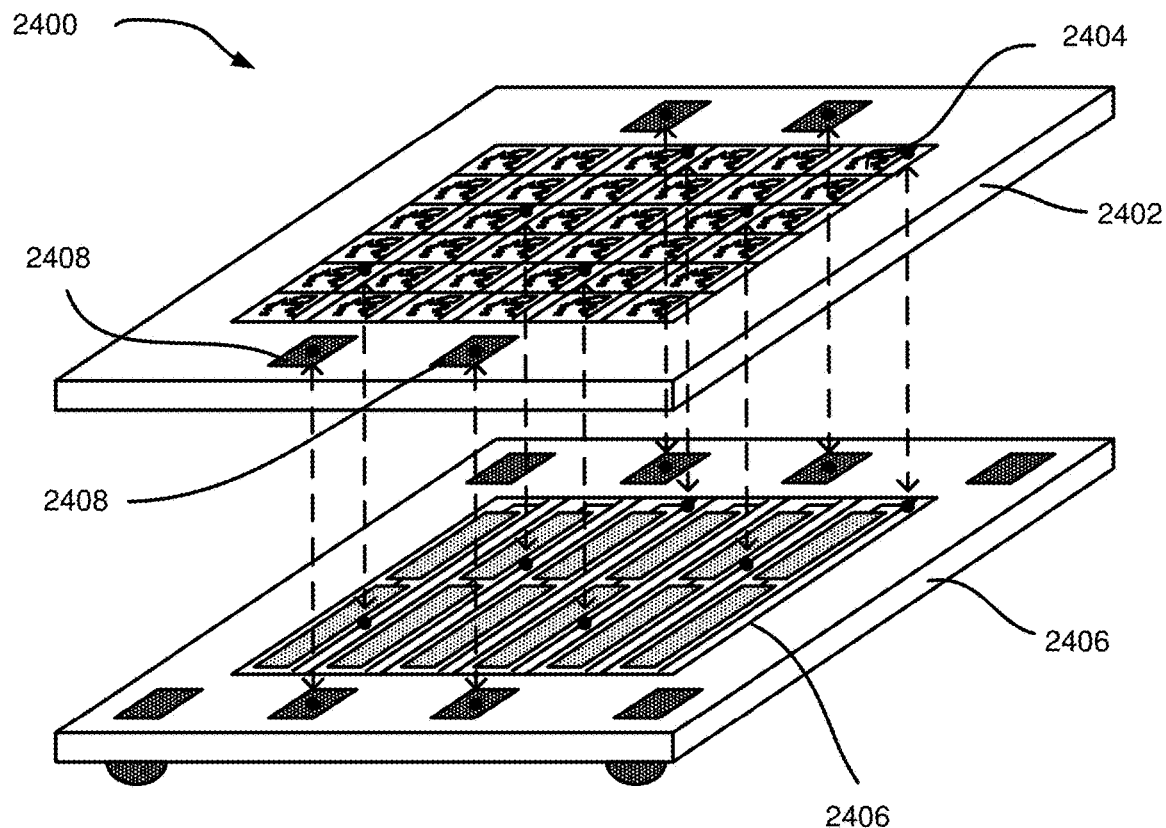
FIGS. 24A and 24B illustrate a perspective view and a side view, respectively, of an implementation of an imaging sensor built on a plurality of substrates, wherein a plurality of pixel columns forming the pixel array are located on the first substrate and a plurality of circuit columns are located on a second substrate and showing an electrical connection and communication between one column of pixels to its associated or corresponding column of circuitry.
Figure 24B:
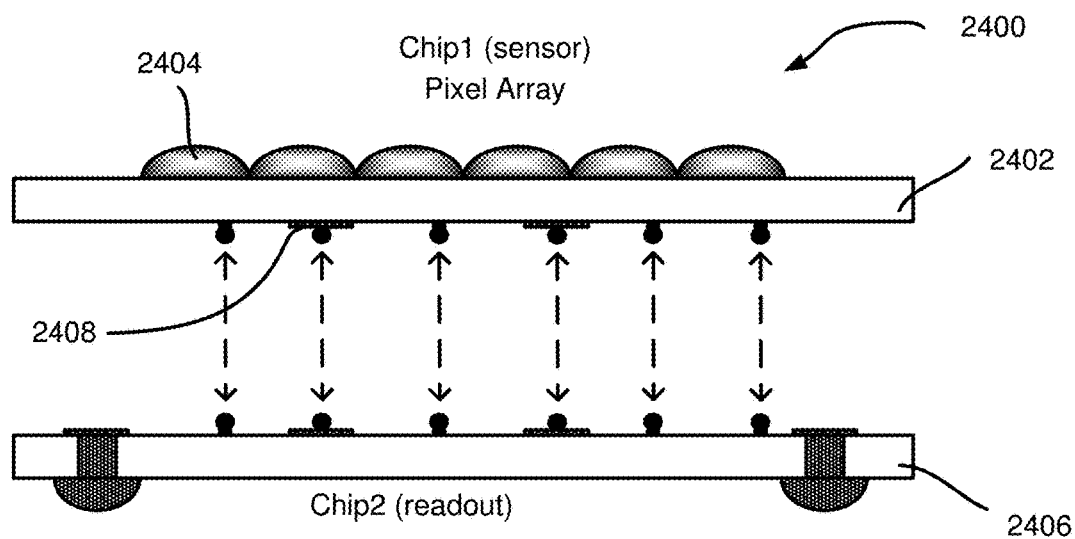

FIGS. 24A and 24B illustrate a perspective view and a side view, respectively, of an implementation of an imaging sensor 2400 built on a plurality of substrates. As illustrated, a plurality of pixel columns 2404 forming the pixel array are located on the first substrate 2402 and a plurality of circuit columns 2408 are located on a second substrate 1906. Also illustrated in the figure are the electrical connection and communication between one column of pixels to its associated or corresponding column of circuitry. In one implementation, an image sensor, which might otherwise be manufactured with its pixel array and supporting circuitry on a single, monolithic substrate/chip, may have the pixel array separated from all or a majority of the supporting circuitry. The disclosure may use at least two substrates/chips, which will be stacked together using three-dimensional stacking technology. The first 2402 of the two substrates/chips may be processed using an image CMOS process. The first substrate/chip 2402 may be comprised either of a pixel array exclusively or a pixel array surrounded by limited circuitry. The second or subsequent substrate/chip 1906 may be processed using any process and does not have to be from an image CMOS process. The second substrate/chip 1906 may be, but is not limited to, a highly dense digital process to integrate a variety and number of functions in a very limited space or area on the substrate/chip, or a mixed-mode or analog process to integrate for example precise analog functions, or a RF process to implement wireless capability, or MEMS (Micro-Electro-Mechanical Systems) to integrate MEMS devices. The image CMOS substrate/chip 2402 may be stacked with the second or subsequent substrate/chip 1906 using any three-dimensional technique. The second substrate/chip 1906 may support most, or a majority, of the circuitry that would have otherwise been implemented in the first image CMOS chip 2402 (if implemented on a monolithic substrate/chip) as peripheral circuits and therefore have increased the overall system area while keeping the pixel array size constant and optimized to the fullest extent possible. The electrical connection between the two substrates/chips may be done through interconnects, which may be wire bonds, bump and/or TSV (Through Silicon Via).

FIGS. 25A and 25B illustrate a perspective view and a side view, respectively, of an implementation of an imaging sensor 2500 having a plurality of pixel arrays for producing a three-dimensional image. The three-dimensional image sensor may be built on a plurality of substrates and may comprise the plurality of pixel arrays and other associated circuitry, wherein a plurality of pixel columns 2504a forming the first pixel array and a plurality of pixel columns 2504b forming a second pixel array are located on respective substrates 2502a and 2502b, respectively, and a plurality of circuit columns 2508a and 2508b are located on a separate substrate 2506. Also illustrated are the electrical connections and communications between columns of pixels to associated or corresponding column of circuitry.

The plurality of pixel arrays may sense information simultaneously and the information from the plurality of pixel arrays may be combined to generate a three-dimensional image. In an embodiment, an endoscopic imaging system includes two or more pixel arrays that can be deployed to generate three-dimensional imaging. The endoscopic imaging system may include an emitter for emitting pulses of electromagnetic radiation during a blanking period of the pixel arrays. The pixel arrays may be synced such that the optical black pixels are read (i.e., the blanking period occurs) at the same time for the two or more pixel arrays. The emitter may emit pulses of electromagnetic radiation for charging each of the two or more pixel arrays. The two or more pixel arrays may read their respective charged pixels at the same time such that the readout periods for the two or more pixel arrays occur at the same time or at approximately the same time. In an embodiment, the endoscopic imaging system includes multiple emitters that are each individual synced with one or more pixel arrays of a plurality of pixel arrays. Information from a plurality of pixel arrays may be combined to generate three-dimensional image frames and video streams.

It will be appreciated that the teachings and principles of the disclosure may be used in a reusable device platform, a limited use device platform, a re-posable use device platform, or a single use/disposable device platform without departing from the scope of the disclosure. It will be appreciated that in a re-usable device platform an end-user is responsible for cleaning and sterilization of the device. In a limited use device platform, the device can be used for some specified amount of times before becoming inoperable. Typical new device is delivered sterile with additional uses requiring the end-user to clean and sterilize before additional uses. In a re-posable use device platform, a third-party may reprocess the device (e.g., cleans, packages and sterilizes) a single-use device for additional uses at a lower cost than a new unit. In a single use/disposable device platform a device is provided sterile to the operating room and used only once before being disposed of.

EXAMPLES

The following examples pertain to preferred features of further embodiments:

Example 1 is a system. The system includes an emitter for emitting pulses of electromagnetic radiation and an image sensor comprising a pixel array for sensing reflected electromagnetic radiation. The system includes a plurality of bidirectional pads in communication with the image sensor, wherein each of the plurality of bidirectional pads comprises an output state for issuing data and an input state for receiving data. The system includes a controller in electronic communication with the image sensor and the emitter configured to synchronize timing of the emitter and the image sensor to generate a plurality of exposure frames. The system is such that at least a portion of the pulses of electromagnetic radiation emitted by the emitter comprises one or more of: electromagnetic radiation having a wavelength from about 513 nm to about 545 nm; electromagnetic radiation having a wavelength from about 565 nm to about 585 nm; or electromagnetic radiation having a wavelength from about 900 nm to about 1000 nm.

Example 2 is a system as in Example 1, wherein the image sensor controls the plurality of bidirectional pads to be configured in the output state or the input state, and wherein the image sensor automatically switches between the output state and the input state for the plurality of bidirectional pads.

Example 3 is a system as in any of Examples 1-2, wherein the plurality of bidirectional pads are in: the output state when pixel data is output from the image sensor, wherein the pixel data is generated by exposing the pixel array; and the input state when receiving control commands for the operation of the image sensor.

Example 4 is a system as in any of Examples 1-3, further comprising a state identifier for identifying when the plurality of bidirectional pads are in the output state or the input state.

Example 5 is a system as in any of Examples 1-4, wherein the image sensor does not receive slow-control commands via the plurality of bidirectional pads when the plurality of bidirectional pads are in the output state.

Example 6 is a system as in any of Examples 1-5, wherein the controller is configured to synchronize timing of the emitter and the image sensor by causing the emitter to emit a pulse of electromagnetic radiation when the plurality of bidirectional pads are in the output state.

Example 7 is a system as in any of Examples 1-6, wherein the controller is configured to synchronize timing of the emitter and the image sensor by causing the emitter to emit a pulse of electromagnetic radiation when the plurality of bidirectional pads are in the input state.

Example 8 is a system as in any of Examples 1-7, wherein the image sensor is configured to generate a plurality of exposure frames, wherein each of the plurality of exposure frames corresponds to a pulse of electromagnetic radiation emitted by the emitter.

Example 9 is a system as in any of Examples 1-8, wherein the pixel array of the image sensor senses reflected electromagnetic radiation to generate the plurality of exposure frames during a readout period of the pixel array, wherein the readout period is a duration of time when active pixels in the pixel array are read.

Example 10 is a system as in any of Examples 1-9, wherein at least a portion of the pulses of electromagnetic radiation emitted by the emitter is a hyperspectral wavelength for eliciting a spectral response, wherein the hyperspectral wavelength comprises one or more of: the electromagnetic radiation having the wavelength from about 513 nm to about 545 nm and the electromagnetic radiation having the wavelength from about 900 nm to about 1000 nm; or the electromagnetic radiation having the wavelength from about 565 nm to about 585 nm and the electromagnetic radiation having the wavelength from about 900 nm to about 1000 nm.

Example 11 is a system as in any of Examples 1-10, wherein the emitter is configured to emit, during a pulse duration, a plurality of sub-pulses of electromagnetic radiation having a sub-duration shorter than the pulse duration.

Example 12 is a system as in any of Examples 1-11, wherein one or more of the pulses of electromagnetic radiation emitted by the emitter comprises electromagnetic radiation emitted at two or more wavelengths simultaneously as a single pulse or a single sub-pulse.

Example 13 is a system as in any of Examples 1-12, wherein at least a portion of the pulses of electromagnetic radiation emitted by the emitter is a hyperspectral emission that results in a hyperspectral exposure frame created by the image sensor, and wherein the controller is configured to provide the hyperspectral exposure frame to a corresponding system that determines a location of a critical tissue structure within a scene based on the hyperspectral exposure frame.\

Example 14 is a system as in any of Examples 1-13, wherein the hyperspectral emission comprises: the electromagnetic radiation having the wavelength from about 513 nm to about 545 nm and the electromagnetic radiation having the wavelength from about 900 nm to about 1000 nm; or the electromagnetic radiation having the wavelength from about 565 nm to about 585 nm and the electromagnetic radiation having the wavelength from about 900 nm to about 1000 nm.

Example 15 is a system as in any of Examples 1-14, wherein the controller is further configured to: receive the location of the critical tissue structure from the corresponding system; generate an overlay frame comprising the location of the critical tissue structure; and combine the overlay frame with a color image frame depicting the scene to indicate the location of the critical tissue structure within the scene.

Example 16 is a system as in any of Examples 1-15, wherein the critical structure comprises one or more of a nerve, a ureter, a blood vessel, an artery, a blood flow, or a tumor.

Example 17 is a system as in any of Examples 1-16, wherein the controller is configured to synchronize timing of the pulses of electromagnetic radiation during a blanking period of the image sensor, wherein the blanking period corresponds to a time between a readout of a last row of active pixels in the pixel array and a beginning of a next subsequent readout of active pixels in the pixel array.

Example 18 is a system as in any of Examples 1-17, wherein two or more pulses of electromagnetic radiation emitted by the emitter result in two or more instances of reflected electromagnetic radiation that are sensed by the pixel array to generate two or more exposure frames that are combined to form an image frame.

Example 19 is a system as in any of Examples 1-18, wherein the image sensor comprises a first image sensor and a second image sensor such that the image sensor can generate a three-dimensional image.

Example 20 is a system as in any of Examples 1-19, wherein the emitter is configured to emit a sequence of pulses of electromagnetic radiation repeatedly sufficient for generating a video stream comprising a plurality of image frames, wherein each image frame in the video stream comprises data from a plurality of exposure frames, and wherein each of the exposure frames corresponds to a pulse of electromagnetic radiation.

Example 21 is a system as in any of Examples 1-20, wherein the pulses of electromagnetic radiation are emitted in a pattern of varying wavelengths of electromagnetic radiation, and wherein the emitter repeats the pattern of varying wavelengths of electromagnetic radiation.

Example 22 is a system as in any of Examples 1-21, wherein at least a portion of the pulses of electromagnetic radiation comprise a red wavelength, a green wavelength, a blue wavelength, and a hyperspectral wavelength such that reflected electromagnetic radiation sensed by the pixel array corresponding to each of the red wavelength, the green wavelength, the blue wavelength, and the hyperspectral wavelength can be processed to generate a Red-Green-Blue (RGB) image frame comprising an overlay of hyperspectral imaging data, wherein the hyperspectral wavelength of electromagnetic radiation comprises: the electromagnetic radiation having the wavelength from about 513 nm to about 545 nm and the electromagnetic radiation having the wavelength from about 900 nm to about 1000 nm; or the electromagnetic radiation having the wavelength from about 565 nm to about 585 nm and the electromagnetic radiation having the wavelength from about 900 nm to about 1000 nm.

Example 23 is a system as in any of Examples 1-22, wherein at least a portion of the pulses of electromagnetic radiation comprise a luminance emission, a red chrominance emission, a blue chrominance emission, and a hyperspectral emission such that reflected electromagnetic radiation sensed by the pixel array corresponding to each of the luminance emission, the red chrominance emission, the blue chrominance emission, and the hyperspectral emission can be processed to generate a YCbCr image frame comprising an overlay of hyperspectral imaging data, wherein the hyperspectral emission of electromagnetic radiation comprises: the electromagnetic radiation having the wavelength from about 513 nm to about 545 nm and the electromagnetic radiation having the wavelength from about 900 nm to about 1000 nm; or the electromagnetic radiation having the wavelength from about 565 nm to about 585 nm and the electromagnetic radiation having the wavelength from about 900 nm to about 1000 nm.

It will be appreciated that various features disclosed herein provide significant advantages and advancements in the art. The following claims are exemplary of some of those features.

In the foregoing Detailed Description of the Disclosure, various features of the disclosure are grouped together in a single embodiment for the purpose of streamlining the disclosure. This method of disclosure is not to be interpreted as reflecting an intention that the claimed disclosure requires more features than are expressly recited in each claim. Rather, inventive aspects lie in less than all features of a single foregoing disclosed embodiment.

It is to be understood that any features of the above-described arrangements, examples, and embodiments may be combined in a single embodiment comprising a combination of features taken from any of the disclosed arrangements, examples, and embodiments.

It is to be understood that the above-described arrangements are only illustrative of the application of the principles of the disclosure. Numerous modifications and alternative arrangements may be devised by those skilled in the art without departing from the spirit and scope of the disclosure and the appended claims are intended to cover such modifications and arrangements.

Thus, while the disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

Further, where appropriate, functions described herein can be performed in one or more of: hardware, software, firmware, digital components, or analog components. For example, one or more application specific integrated circuits (ASICs) or field programmable gate arrays (FPGAs) can be programmed to carry out one or more of the systems and procedures described herein. Certain terms are used throughout the following description and claims to refer to particular system components. As one skilled in the art will appreciate, components may be referred to by different names. This document does not intend to distinguish between components that differ in name, but not function.

The foregoing description has been presented for the purposes of illustration and description. It is not intended to be exhaustive or to limit the disclosure to the precise form disclosed. Many modifications and variations are possible in light of the above teaching. Further, it should be noted that any or all the aforementioned alternate implementations may be used in any combination desired to form additional hybrid implementations of the disclosure.

Further, although specific implementations of the disclosure have been described and illustrated, the disclosure is not to be limited to the specific forms or arrangements of parts so described and illustrated. The scope of the disclosure is to be defined by the claims appended hereto, any future claims submitted here and in different applications, and their equivalents.

What is claimed is:

1. A system comprising:
    an emitter for emitting pulses of electromagnetic radiation;
    an image sensor comprising a pixel array for sensing reflected electromagnetic radiation;
    a plurality of bidirectional pads in communication with the image sensor, wherein each of the plurality of bidirectional pads comprises an output state for issuing data and an input state for receiving data; and
    a controller in electronic communication with the image sensor and the emitter configured to synchronize timing of the emitter and the image sensor to generate a plurality of exposure frames;
    wherein at least a portion of the pulses of electromagnetic radiation emitted by the emitter comprises a visible wavelength of electromagnetic radiation and a hyperspectral emission for eliciting a spectral response, wherein the hyperspectral emission comprises one or more of:
        electromagnetic radiation having a wavelength from about 513 nm to about 545 nm;
        electromagnetic radiation having a wavelength from about 565 nm to about 585 nm; or
        electromagnetic radiation having a wavelength from about 900 nm to about 1000 nm.

2. The system of claim 1, wherein the image sensor controls the plurality of bidirectional pads to be configured in the output state or the input state, and wherein the image sensor automatically switches between the output state and the input state for the plurality of bidirectional pads.

3. The system of claim 1, wherein the plurality of bidirectional pads are in:
    the output state when pixel data is output from the image sensor, wherein the pixel data is generated by exposing the pixel array; and
    the input state when receiving control commands for the operation of the image sensor.

4. The system of claim 1, further comprising a state identifier for identifying when the plurality of bidirectional pads are in the output state or the input state.

5. The system of claim 1, wherein the image sensor does not receive slow-control commands via the plurality of bidirectional pads when the plurality of bidirectional pads are in the output state.

6. The system of claim 1, wherein the controller is configured to synchronize timing of the emitter and the image sensor by causing the emitter to emit a pulse of electromagnetic radiation when the plurality of bidirectional pads are in the output state.

7. The system of claim 1, wherein the controller is configured to synchronize timing of the emitter and the image sensor by causing the emitter to emit a pulse of electromagnetic radiation when the plurality of bidirectional pads are in the input state.

8. The system of claim 1, wherein the image sensor is configured to generate a plurality of exposure frames, wherein each of the plurality of exposure frames corresponds to a pulse of electromagnetic radiation emitted by the emitter.

9. The system of claim 8, wherein the pixel array of the image sensor senses reflected electromagnetic radiation to generate the plurality of exposure frames during a readout period of the pixel array, wherein the readout period is a duration of time when active pixels in the pixel array are read.

10. The system of claim 1, wherein the hyperspectral wavelength comprises one or more of:
    the electromagnetic radiation having the wavelength from about 513 nm to about 545 nm and the electromagnetic radiation having the wavelength from about 900 nm to about 1000 nm; or
    the electromagnetic radiation having the wavelength from about 565 nm to about 585 nm and the electromagnetic radiation having the wavelength from about 900 nm to about 1000 nm.

11. The system of claim 1, wherein the emitter is configured to emit, during a pulse duration, a plurality of sub-pulses of electromagnetic radiation having a sub-duration shorter than the pulse duration.

12. The system of claim 1, wherein one or more of the pulses of electromagnetic radiation emitted by the emitter comprises electromagnetic radiation emitted at two or more wavelengths simultaneously as a single pulse or a single sub-pulse.

13. The system of claim 1, wherein the hyperspectral emission results in a hyperspectral exposure frame sensed by the image sensor, and wherein the controller is configured to provide the hyperspectral exposure frame to a corresponding system that determines a location of a tissue structure within a scene based on the hyperspectral exposure frame.

14. The system of claim 13, wherein the hyperspectral emission comprises:
    the electromagnetic radiation having the wavelength from about 513 nm to about 545 nm and the electromagnetic radiation having the wavelength from about 900 nm to about 1000 nm; or the electromagnetic radiation having the wavelength from about 565 nm to about 585 nm and the electromagnetic radiation having the wavelength from about 900 nm to about 1000 nm.

15. The system of claim 14, wherein the controller is further configured to:
receive the location of the critical tissue structure from the corresponding system;
generate an overlay frame comprising the location of the tissue structure; and
combine the overlay frame with a color image frame depicting the scene to indicate the location of the tissue structure within the scene.

16. The system of claim 15, wherein the tissue structure comprises one or more of a nerve, a ureter, a blood vessel, an artery, a blood flow, or a tumor.

17. The system of claim 1, wherein the controller is configured to synchronize timing of the pulses of electromagnetic radiation during a blanking period of the image sensor, wherein the blanking period corresponds to a time between a readout of a last row of active pixels in the pixel array and a beginning of a next subsequent readout of active pixels in the pixel array.

18. The system of claim 1, wherein two or more pulses of electromagnetic radiation emitted by the emitter result in two or more instances of reflected electromagnetic radiation that are sensed by the pixel array to generate two or more exposure frames that are combined to form an image frame.

19. The system of claim 1, wherein the image sensor comprises a first image sensor and a second image sensor such that the image sensor can generate a three-dimensional image.

20. The system of claim 1, wherein the emitter is configured to emit a sequence of pulses of electromagnetic radiation repeatedly sufficient for generating a video stream comprising a plurality of image frames, wherein each image frame in the video stream comprises data from a plurality of exposure frames, and wherein each of the plurality of exposure frames corresponds to a pulse of electromagnetic radiation.

21. The system of claim 1, wherein the pulses of electromagnetic radiation are emitted in a pattern of varying wavelengths of electromagnetic radiation, and wherein the emitter repeats the pattern of varying wavelengths of electromagnetic radiation.

22. The system of claim 1, wherein reflected electromagnetic radiation sensed by the pixel array corresponding to each of the visible wavelength and the hyperspectral emission can be processed to generate a Red-Green-Blue (RGB) image frame comprising an overlay of hyperspectral imaging data, wherein the hyperspectral emission comprises:
the electromagnetic radiation having the wavelength from about 513 nm to about 545 nm and the electromagnetic radiation having the wavelength from about 900 nm to about 1000 nm; or
the electromagnetic radiation having the wavelength from about 565 nm to about 585 nm and the electromagnetic radiation having the wavelength from about 900 nm to about 1000 nm.

23. The system of claim 1, wherein the reflected electromagnetic radiation sensed by the pixel array corresponding to each of the visible wavelength and the hyperspectral emission can be processed to generate a YCbCr image frame comprising an overlay of hyperspectral imaging data, wherein the hyperspectral emission comprises:
the electromagnetic radiation having the wavelength from about 513 nm to about 545 nm and the electromagnetic radiation having the wavelength from about 900 nm to about 1000 nm; or
the electromagnetic radiation having the wavelength from about 565 nm to about 585 nm and the electromagnetic radiation having the wavelength from about 900 nm to about 1000 nm.

\* \* \* \* \*